US012735399B2

(12) United States Patent
Krauss et al.

(10) Patent No.: US 12,735,399 B2
(45) **Date of Patent: *Sep. 15, 2026**

(54) TRIAZOLE DERIVATIVES AND THEIR USE AS TANKYRASE INHIBITORS

(71) Applicants: OSLO UNIVERSITETSSYKEHUS HF, Oslo (NO); UNIVERSITY OF OULU, Oulu (FI)

(72) Inventors: Stefan Krauss, Eidsvoll Verk (NO); Jo Waaler, Oslo (NO); Anita Wegert, Aldenhoven (DE); Ruben Gerardus George Leenders, Nijmegen (NL); Lari Lehtio, Oulu (FI)

(73) Assignees: Oslo Universitetssykehus HF, Oslo (NO); University of Oulu, Oulu (FI)

( * ) Notice: Subject to any disclaimer, the term of this patent is extended or adjusted under 35 U.S.C. 154(b) by 695 days.

This patent is subject to a terminal disclaimer.

(21) Appl. No.: 18/014,840

(22) PCT Filed: Jul. 6, 2021

(86) PCT No.: PCT/GB2021/051714

§ 371 (c)(1),
(2) Date: Jan. 6, 2023

(87) PCT Pub. No.: WO2022/008896

PCT Pub. Date: Jan. 13, 2022

(65) Prior Publication Data

US 2023/0322721 A1 Oct. 12, 2023

(30) Foreign Application Priority Data

Jul. 6, 2020 (GB) ..................................... 2010359

(51) Int. Cl.
*C07D 401/14* (2006.01)
*C07D 401/04* (2006.01)
*C07D 471/04* (2006.01)

(52) U.S. Cl.
CPC ......... *C07D 401/14* (2013.01); *C07D 401/04* (2013.01); *C07D 471/04* (2013.01)

(58) Field of Classification Search
CPC ... C07D 401/14; C07D 401/04; C07D 471/04
See application file for complete search history.

(56) References Cited

U.S. PATENT DOCUMENTS 11,926,614 B2 * 3/2024 Krauss et al.
2005/0154024 A1 * 7/2005 Bryans et al.

FOREIGN PATENT DOCUMENTS

JP 2018-520992 A 8/2018
WO 2010/139966 A1 12/2010

(Continued)

OTHER PUBLICATIONS

Search Report issued for Application No. GB2010359.4, dated Jan. 7, 2021.

(Continued)

*Primary Examiner* — Sarah Pihonak
*Assistant Examiner* — Jackson J Hernandez
(74) *Attorney, Agent, or Firm* — Meunier Carlin & Curfman LLC

(57) ABSTRACT

The present invention relates to compounds of general formula (I), tautomers, stereoisomers, N-oxides, pharmaceutically acceptable salts and pro-drug thereof, to processes for their preparation, to pharmaceutical compositions containing such compounds and to their use in therapy: wherein: a dashed line indicates an optional bond; X represents: a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl); a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); Y represents: an aryl or heteroaryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); a 5- or 6-membered, saturated heterocyclic group optionally substituted by one or more (e.g. 1, 2 or 3) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and Z represents: an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or C1-3 alkyl), —$SO_2N(R_3)2$ (where each $R^3$ is independently H or $C_{1-6}$ alkyl, e.g. H or $C_{1-3}$ alkyl), and —C(O)N(R4)2 (where each R4 is independently H or $C_{1-6}$ alkyl, e.g. H or $C_{1-3}$ alkyl, or wherein both R4 groups, together with the intervening nitrogen atom, form a 3 to 6 membered saturated heterocyclic ring); or an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ (Continued)

alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); with the proviso: that when the compound is other than an N-oxide of formula (I), Z must be substituted by at least one substituent selected from —OH, —$N(R^3)_2$, —$SO_2N(R^3)_2$ and —$C(O)N(R^4)_2$, preferably by at least one substituent selected from —OH, —$SO_2N(R^3)_2$ and —$C(O)N(R^4)_2$. These compounds find particular use in the treatment and/or prevention of a disease or disorder responsive to inhibition of tankyrase 1 and/or 2, for example a disorder which is mediated by tankyrase 1 and/or 2 such as cancer.

(I)

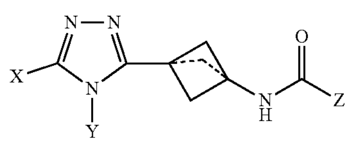

24 Claims, No Drawings

(56) References Cited

FOREIGN PATENT DOCUMENTS

| | | | |
|---|---|---|---|
| WO | 2012/076898 | A1 | 6/2012 |
| WO | 2016177658 | A1 | 11/2016 |
| WO | 2018045182 | A1 | 3/2018 |
| WO | 2018/118868 | A1 | 6/2018 |
| WO | 2019/243822 | A1 | 12/2019 |

OTHER PUBLICATIONS

International Search Report and Written Opinion issued for Application No. PCT/GB2021/051714, dated Aug. 30, 2021.

International Preliminary Report on Patentability issued for Application No. PCT/GB2021/051714, dated Jan. 19, 2023.

Jo Waaler et al., "Pharmaceutical Lead Optimization of a 1,2,4-Triazole Based Tankyrase Inhibitor", Journal of Medicinal Chemistry, vol. 63, No. 13, Jun. 8, 2020, pp. 6834-6846.

Anumala, Upendra Rao, et al. "Discovery of a novel series of tankyrase inhibitors by a hybridization approach." Journal of Medicinal Chemistry 60.24 (2017): 10013-10025.

Office Action mailed on May 27, 2025, in Japanese Application No. 2023-500398.

* cited by examiner

TRIAZOLE DERIVATIVES AND THEIR USE AS TANKYRASE INHIBITORS

FIELD OF THE INVENTION

The present invention relates to novel compounds, to pharmaceutical formulations containing them and to their use in therapy, in particular as tankyrase (TNKS) inhibitors and, more specifically, as inhibitors of the WNT/β-catenin and hippo signalling pathways. The invention further relates to processes for the preparation of such compounds.

The compounds of the invention find particular use in the treatment of conditions mediated by tankyrase, including disorders associated with aberrant signalling in the WNT/β-catenin signalling pathway such as WNT/β-catenin signalling-related cancers, and disorders associated with aberrant signalling in the hippo signalling pathway such as hippo signalling-related cancers. They also find use in the treatment of other signalling disorders that are impacted by tankyrase such as proliferative diseases, fibrosis, osteoarthritis, metabolic conditions (e.g. aberrant systemic glucose metabolism) and viral infections (e.g. influenza and herpes simplex virus infections).

BACKGROUND OF THE INVENTION

WNT/β-catenin signalling is altered in a variety of tumors including tumors emerging from colorectal tissue, uterus, pancreas, skin, liver, thyroid, prostate, ovary, stomach, lung, lymphoid, bladder, brain, breast and kidney. Increased β-catenin levels have been identified as a central factor in T-cell infiltration in melanoma specimens (Spranger et al., Nature. 2015 Jul. 9; 523 (7559): 231-5) and a correlation between WNT/β-catenin pathway activation and immune exclusion has been observed across numerous human cancers (Luke et al., J. Clin. Oncol. 2016; 34 (suppl; abstract 3004)). The key effector in the hippo pathway, YAP, has also been identified as an oncoprotein whose expression is elevated in various human cancers (Wang et al., Cell Rep. 2015 Oct. 20; 13(3): 524-532).

Tankyrase 1 and 2 (TNKS1 and TNKS2) (PARP-5a, PARP-5b) are members of the poly-ADP-ribose polymerase (PARP) family of enzymes. Tankyrase 1/2 have been identified as regulators of the WNT/β-catenin signalling pathway via interactions with AXIN1/2 proteins and a regulator of the hippo-signalling pathway via interactions with members of the AMOT family of proteins (Wang et al., Cell Rep. 2015 Oct. 20; 13(3):524-532). The inhibition of tankyrase 1/2 produces elevated AXIN protein levels and reduced levels of cellular β-catenin even in the absence of a dysfunctional and truncated form of APC protein. The inhibition of tankyrase 1/2 also stabilizes the AMOT family proteins, thereby suppressing YAP oncogenic functions. TNKS1/2 also affects directly other biotargets including PGC-1α, TRF1, PTEN, SOX9, TBP-43 and SH3BP2 (see, for example, Int. J. Obes. (Lond). 2020 Apr. 21. doi: 10.1038/s41366-020-0573-z; Mukai et al., Cells. 2019, 8(2), 195; Kim, Oncol. Lett. 2018, 16(6), 6895-6902; Haikarainen et al., Curr. Pharm. Des. 2014, 20(41), 6472-6488; Peters et al., Anticancer Agents Med. Chem. 2019, 19(16), 1920-1934; and Kim et al., Nat. Comm., Volume 10, Article number: 4898 (2019)).

Several groups of chemical substances (XAV939, MN-64, CMP8, CMP18, CMP11, CMP30, IWR-1, CMP40, CMP4, MSC2504877, ZYTP1, WIKI4, JW74, JW55, G007-LK, CMP24, CMP4b, MVP-TNKS656, AZ0108, E7449, 3-arylisoquinolin-1-one and 1,2,4-triazole based inhibitors) have been identified which inhibit tankyrase 1 and 2 (Chen et al., Nat. Chem. Biol. 5: 100-107, 2009; Huang et al., Nature: 461: 614-620, 2009; Waaler et al., Cancer Res. 2011 Jan. 1; 71(1):197-205; Voronkov et al., J. Med. Chem. 2013 Apr. 11; 56(7): 3012-23; Bregman et al., J Med Chem. 2013 Feb. 14; 56(3): 1341-5; Bregman et al., J Med Chem. 2013 Jun. 13; 56(11): 4320-42; Haikarainen et al., Curr. Pharm. Des. 20(41): 6472-88, 2014; McGonigle et al., Oncotarget 6(38): 41307-23, 2015; Paine et al., Bioorg. Med. Chem. 23(17): 5891-908, 2015; Nkizinkiko et al., Bioorg. Med. Chem. 23(15): 4139-49, 2015; Haikarainen et al., Bioorg. Med. Chem. Lett. 26(2): 328-332016, 2016; Anumala et al., J Med Chem. 2017 Dec. 28; 60(24): 10013-10025; Ferri et al., Eur J Med Chem. 2017 Dec. 15; 142: 506-522; Waaler et al., J Med Chem 2020 Jun. 23. doi: 10.1021/acs.jmedchem.0c00208; Tomassi et al., ACS Med Chem Lett. 2020 11(5), 862-868; Shirai et al., J Med Chem. 2020, 63(8), 4183-4204; Abdelrehim et al., Curr Org Synth. 2020, 17(3), 211-223; Buchstaller et al., J Med Chem. 2019, 62(17), 7897-7909; Shirai et al, J Med Chem. 2019, 62(7), 3407-3427; Menon et al., Sci Rep. 2019, 9(1):201; Mizutani et al., Cancer Sci. 2018, 109, 4003-4014; Jain et al., Cancer Chemother. Pharmacol. 2018, 82(4), 635-647; and Nkizinkiko et al., Sci Rep. 2018 8(1):1680).

Compounds which exhibit activity in blocking tankyrase 1 and 2 are described in WO 2010/139966, WO 2012/076898 and WO 2018/118868. Other compounds which display a high target affinity towards tankyrase 1 and 2 and which have been shown to be effective in a tumor xenograft model are described by Anumala et al. in J. Med. Chem. 60(24): 10013-10025, 2017. More recently, the inventors identified other compounds which are highly effective in blocking tankyrase 1 and 2. These are described in WO 2019/243822.

The inventors have now identified further compounds which are effective tankyrase 1 and 2 inhibitors. These compounds represent at least an alternative and, in some cases, an improvement over those disclosed in WO 2019/243822. In particular, some of these compounds exhibit one or more ADME parameters (adsorption/distribution/metabolism/excretion) which are improved compared to the earlier compounds, such as an improved metabolic stability.

Given the central importance of WNT/β-catenin signalling and hippo signalling in a wide range of cancers, the novel compounds described herein are expected to be suitable for inhibiting tumor cells in general and, in particular, those associated with colorectal cancers, gastrointestinal tumors, non-small cell lung cancer, breast cancer, CNS cancers, endocrine and neuroendocrine tumors, ovary cancer, testicular cancer, liver cancer, renal cancer, melanoma, soft tissue cancer, bone cancer and pancreatic adenocarcinoma. The compounds are also suitable for cancer immunotherapy, for example when used in combination with checkpoint inhibitors such as PD-1 and PD-L1.

The compounds described herein also find use in the treatment of other disorders associated with tankyrase 1 and 2 activity, for example in treating fibrotic diseases, osteoarthritis, metabolic conditions (e.g. aberrant systemic glucose metabolism and type 2 diabetes), influenza and herpes simplex virus (HSV) infections.

SUMMARY OF THE INVENTION

In one aspect the invention relates to compounds of general formula (I), their tautomers, stereoisomers, N-oxides, pharmaceutically acceptable salts and pro-drugs:

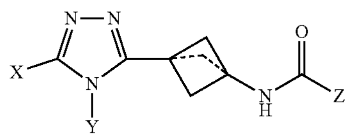

(I)

wherein:

a dashed line indicates an optional bond;

X represents:

a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl);

a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);

Y represents:

an aryl or heteroaryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);

a 5- or 6-membered, saturated heterocyclic group optionally substituted by one or more (e.g. 1, 2 or 3) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and Z represents:

an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); or an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring);

with the proviso:

that when the compound is other than an N-oxide of formula (I), Z must be substituted by at least one substituent selected from —OH, —$N(R^1)_2$, —$SO_2N(R^3)_2$ and —$C(O)N(R^4)_2$, preferably by at least one substituent selected from —OH, —$SO_2N(R^3)_2$ and —$C(O)N(R^4)_2$.

In another aspect the invention relates to a pharmaceutical composition comprising a compound of formula (I), a tautomer, a stereoisomer, an N-oxide, a pharmaceutically acceptable salt, or a pro-drug thereof as herein described, together with one or more pharmaceutically acceptable carriers, excipients or diluents.

In a further aspect the invention relates to a compound of formula (I), a tautomer, a stereoisomer, an N-oxide, a pharmaceutically acceptable salt, or a pro-drug thereof as herein described for use in therapy or for use as a medicament.

In a yet further aspect the invention relates to a compound of formula (I), a tautomer, a stereoisomer, an N-oxide, a pharmaceutically acceptable salt, or a pro-drug thereof as herein described for use in the inhibition of tankyrase 1 and/or 2.

In a further aspect the invention relates to a compound of formula (I), a tautomer, a stereoisomer, an N-oxide, a pharmaceutically acceptable salt, or a pro-drug thereof as herein described for use in the treatment or prevention of a disease or disorder responsive to inhibition of tankyrase 1 and/or 2, for example a disorder which is mediated by tankyrase 1 and/or 2, preferably for use in the treatment or prevention of a disorder such as cancer.

In a further aspect the invention relates to the use of a compound of formula (I), a tautomer, a stereoisomer, an N-oxide, a pharmaceutically acceptable salt, or a pro-drug thereof as herein described in the manufacture of a medicament for use in the treatment or prevention of a disease or disorder responsive to inhibition of tankyrase 1 and/or 2, for example a disorder which is mediated by tankyrase 1 and/or 2, preferably a disorder such as cancer.

A yet further aspect of the invention relates to a method of treatment or prevention of a disease or disorder responsive to inhibition of tankyrase 1 and/or 2, for example a disorder which is mediated by tankyrase 1 and/or 2, preferably a method of treatment or prevention of a disorder such as cancer, said method comprising the step of administering to a patient in need thereof (e.g. a human patient) a pharmaceutically effective amount of a compound of formula (I), a tautomer, a stereoisomer, an N-oxide, a pharmaceutically acceptable salt, or a pro-drug thereof as herein described.

DETAILED DESCRIPTION OF THE INVENTION

Definitions

As used herein, the term "alkyl" refers to a saturated hydrocarbon group and is intended to cover both straightchained and branched alkyl groups. Examples of such groups include methyl, ethyl, n-propyl, iso-propyl, n-butyl, tert-butyl, sec-butyl, n-pentyl, iso-pentyl, neo-pentyl, n-hexyl, 2-methylbutyl, 2-methylpentyl, 2-ethylbutyl, 3-methylpentyl, and 4-methylpentyl. An alkyl group preferably contains from 1-6 carbon atoms, more preferably 1-4 carbon atoms, e.g. 1-3 carbon atoms. The term "alkyl" group also includes any saturated hydrocarbon group in which one or more (e.g. all) hydrogen atoms are replaced with deuterium. Examples of such groups include $—CD_3$, $—CD_2CD_3$, $—CD_2CD_2CD_3$, $—CD(CD_3)CD_3$, etc. Unless otherwise specified, any "alkyl" group may be substituted by one or more groups, which may be identical or different. Suitable substituents include hydroxyl, $C_{1-6}$ alkoxy, amino, cyano, or nitro groups, and halogen atoms (e.g. F, Cl or Br). For example, any alkyl group may be substituted by one or more hydroxyl groups, e.g. by one or two hydroxyl groups. Examples of such groups include $—CH(OH)CH_3$ and $—C(OH)(CH_3)(CH_3)$. In an embodiment, any alkyl group herein described may be unsubstituted.

The term "alkoxy" as used herein refers to an —O-alkyl or —O-cycloalkyl group, wherein alkyl and cycloalkyl are as defined herein and alkyl includes deuterated groups in which one or more (e.g. all) hydrogen atoms are replaced with deuterium. Examples of alkoxy groups include, but are not limited to, methoxy, ethoxy, propyloxy, cyclopropyloxy, etc. Unless otherwise specified, any alkoxy group may be substituted in one or more positions with a suitable substituent.

Where more than one substituent group is present, these may be the same or different. Suitable substituents include hydroxy, $C_{1-6}$ alkoxy, amino, cyano, or nitro groups, and halogen atoms (e.g. F, Cl or Br).

The term "cycloalkyl" refers to a monovalent, saturated cyclic carbon system. Examples of cycloalkyl groups include, but are not limited to, cyclopropyl, cyclobutyl, cyclopentyl, and cyclohexyl. Unless otherwise specified, any cycloalkyl group may be substituted in one or more positions with a suitable substituent. Where more than one substituent group is present, these may be the same or different.

The term "halogen" or "halogen atom" refers to —F, —Cl, —Br or —I.

The term "haloalkyl" refers to an alkyl group as defined herein in which at least one of the hydrogen atoms of the alkyl group is replaced by a halogen atom, preferably F, Cl or Br. Examples of such groups include, but are not limited to, $—CH_2F$, $—CHF_2$, $—CF_3$, $—CCl_3$, $—CHCl_2$, $—CH_2CF_3$, etc.

As used herein, the term "unsaturated heterocyclic group" is intended to cover any unsaturated heterocyclic ring which contains at least one heteroatom selected from nitrogen, oxygen and sulphur. Such groups may be monocyclic or polycyclic, preferably mono- or bi-cyclic. Where these contain bicyclic rings, these may be fused. Where such rings are bicyclic these may contain up to 10 ring atoms in which at least one ring contains at least one heteroatom selected from nitrogen, oxygen and sulphur. The heterocyclic ring structure (whether mono- or bicyclic) may be linked to the remainder of the molecule through a carbon atom or, if present, through a nitrogen atom. Typically it will be linked to the remainder of the molecule through a carbon atom. In one embodiment the unsaturated heterocyclic group may contain one or two nitrogen atoms, e.g. two nitrogen atoms. In other embodiments, it may contain one sulphur atom, or one sulphur atom and one nitrogen atom. The unsaturated heterocyclic group may be aromatic or non-aromatic. In one embodiment it may be aromatic, i.e. it may be a "heteroaryl group". Unless otherwise stated, any unsaturated heterocyclic group mentioned herein may optionally be substituted by one or more groups as herein defined, which may be identical or different. Examples of "unsaturated heterocyclic groups" are the heterocycles pyrrole, 2H-pyrrole, pyrroline, pyrazole, imidazole, oxazole, isoxazole, pyrazoline, imidazoline, thiazole, isothiazole, thiadiazole, pyridine, pyridazine, pyrimidine, pyrazine, and triazole. Of these, pyrazole, imidazole, pyrazoline, imidazoline, pyridine, pyridazine, pyrimidine and pyrazine are preferred. Most preferred are pyrimidine and pyridine.

As used herein, the term "saturated heterocyclic group" is intended to cover any heterocyclic ring which contains at least one heteroatom selected from nitrogen, oxygen and sulphur. The ring may be linked to the remainder of the molecule through a carbon atom or through a nitrogen atom. Typically, it will be linked via a carbon atom. Unless otherwise stated, any saturated heterocyclic group mentioned herein may optionally be substituted by one or more groups as herein defined, which may be identical or different.

The term "aryl" as used herein refers to aromatic ring systems. Such ring systems may be monocyclic or bicyclic and contain at least one unsaturated aromatic ring. Where these contain bicyclic rings, these may be fused. Preferably such systems contain from 6-20 carbon atoms, e.g. either 6 or 10 carbon atoms. Examples of such groups include phenyl, 1-napthyl and 2-napthyl. A preferred aryl group is phenyl. Unless stated otherwise, any aryl group may be substituted by one or more substituents as described herein. Where more than one substituent group is present, these may be the same or different.

As used herein, the term "heteroaryl" refers to heterocyclic aromatic groups. Such groups may be monocyclic or bicyclic and contain at least one unsaturated heteroaromatic ring system. Where these are monocyclic, these comprise 5- or 6-membered rings which contain at least one heteroatom selected from nitrogen, oxygen and sulfur and contain sufficient conjugated bonds to form an aromatic system. Where these are bicyclic, these may contain from 9-11 ring atoms. Examples of "heteroaryl groups" include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless otherwise stated, any heteroaryl ring mentioned herein may optionally be substituted by one or more groups as described herein. Where more than one substituent group is present, these may be the same or different.

Where reference is made herein to one or more substituents, this refers to substitution by substituents that can be independently selected from the groups defined herein. In one embodiment, 1, 2, 3, 4, 5 or 6 substituents may be present, preferably 1, 2, or 3, more preferably 1 or 2, e.g. 1.

The compounds of the invention may contain one or more chiral centers and may therefore exist in different stereoisomeric forms. The term "stereoisomer" refers to compounds which have identical chemical constitution but which differ in respect of the spatial arrangement of the atoms or groups. Examples of stereoisomers are enantiomers and diastereomers. The term "enantiomers" refers to two stereoisomers of a compound which are non-superimposable mirror images of one another. The term "diastereoisomers"

refers to stereoisomers with two or more chiral centres which are not mirror images of one another. The invention is considered to extend to diastereomers and enantiomers, as well as racemic mixtures.

The compounds herein described may be resolved into their enantiomers and/or diastereomers. For example, where these contain only one chiral center, these may be provided in the form of a racemate or racemic mixture (a 50:50 mixture of enantiomers) or may be provided as pure enantiomers, i.e. in the R- or S-form. Any of the compounds which occur as racemates may be separated into their enantiomers by methods known in the art, such as column separation on chiral phases or by recrystallization from an optically active solvent. Those compounds with at least two asymmetric carbon atoms may be resolved into their diastereomers on the basis of their physical-chemical differences using methods known per se, e.g. by chromatography and/or fractional crystallization, and where these compounds are obtained in racemic form, they may subsequently be resolved into their enantiomers.

The term "tautomer" as used herein refers to structural isomers which readily interconvert by way of a chemical reaction which may involve the migration of a proton accompanied by a switch of a single bond and adjacent double bond. It includes, in particular, keto-enol and amide-imidic acid tautomers, as well as tautomeric forms of any heterocyclic compounds which contain two or more ring nitrogen atoms (e.g. imidazoles, pyrazoles, tetrazoles, etc.). Examples of amide-imidic acid tautomers include unsaturated, nitrogen-containing heterocycles which have a hydroxyl ring substituent adjacent to the nitrogen atom. Dependent on the conditions, the compounds may predominantly exist in one of the tautomeric forms and the invention is not intended to be limited to the particular form shown in any of the structural formulae given herein.

The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilizes the charge on the parent compound. If the compound of the invention is a base, a suitable pharmaceutically acceptable salt may be prepared by reaction of the free base with an organic or inorganic acid. If the compound of the invention is an acid, a suitable pharmaceutically acceptable salt may be prepared by reaction of the free acid with an organic or inorganic base. Non-limiting examples of suitable salts are described herein.

The term "pharmaceutically acceptable" means that the compound or composition is chemically and/or toxicologically compatible with other components of the formulation or with the patient (e.g. human) to be treated.

By "a pharmaceutical composition" is meant a composition in any form suitable to be used for a medical purpose.

The "N-oxide" form of any compound herein described refers to a compound in which at least one tertiary nitrogen atom is oxidized to the N-oxide. In such compounds, a tertiary nitrogen forms an N—O coordinate covalent bond which may be represented as "$N^+$—O—".

The term "pro-drug" refers to a derivative of an active compound which undergoes a transformation under the conditions of use, for example within the body, to release an active drug. A pro-drug may, but need not necessarily, be pharmacologically inactive until converted into the active drug. As used herein, the term "pro-drug" extends to any compound which under physiological conditions is converted into any of the active compounds herein described. Suitable pro-drugs include compounds which are hydrolysed under physiological conditions to the desired molecule.

Pro-drugs may typically be obtained by masking one or more functional groups in the parent molecule which are considered to be, at least in part, required for activity using a pro-group. By "pro-group" as used herein is meant a group which is used to mask a functional group within an active drug and which undergoes a transformation, such as cleavage, under the specified conditions of use (e.g. administration to the body) to release a functional group and hence provide the active drug. Pro-groups are typically linked to the functional group of the active drug via a bond or bonds that are cleavable under the conditions of use, e.g. in vivo. Cleavage of the pro-group may occur spontaneously under the conditions of use, for example by way of hydrolysis, or it may be catalyzed or induced by other physical or chemical means, e.g. by an enzyme, by exposure to light, by exposure to a change in temperature, or to a change in pH, etc. Where cleavage is induced by other physical or chemical means, these may be endogenous to the conditions of use, for example pH conditions at a target tumor site, or these may be supplied exogenously.

As used herein, "treatment" includes any therapeutic application that can benefit a human or non-human animal (e.g. a non-human mammal). Both human and veterinary treatments are within the scope of the present invention, although primarily the invention is aimed at the treatment of humans. Treatment may be in respect of an existing disease or condition or it may be prophylactic.

As used herein, a "pharmaceutically effective amount" relates to an amount that will lead to the desired pharmacological and/or therapeutic effect, i.e. an amount of the agent which is effective to achieve its intended purpose. While individual patient needs may vary, determination of optimal ranges for effective amounts of the active agent is within the capability of one skilled in the art. Generally, the dosage regimen for treating a disease or condition with any of the compounds described herein is selected in accordance with a variety of factors including the nature of the medical condition and its severity.

Any reference herein to "tankyrase inhibition" with respect to a compound of the invention means a compound that can inhibit tankyrase activity, e.g. reduce and/or eliminate and/or mask and/or prevent the detrimental action of a tankyrase, e.g. tankyrase 1 and/or tankyrase 2. Any reduction in the action of a tankyrase need not be complete but will typically be a reduction of at least about 10%, 20%, 30%, 40%, 50%, 60%, 70%, 80%, or may be as high as at least 90% or at least 95%. Reference to a "tankyrase inhibitor" or "inhibition of tankyrase" should be construed accordingly.

The term "WNT signalling pathway" is used to refer to the chain of events normally mediated by WNT, LRP (LDL-receptor related protein), frizzled, AXIN and β-catenin, among others, and resulting in changes in gene expression and other phenotypic changes typical of WNT activity.

The term "hippo signalling pathway" is used to refer to the chain of events normally mediated by the YAP/TAZ proteins, resulting in changes in gene expression and other phenotypic changes typical of hippo signalling pathway activity.

The invention is based, at least in part, on the finding that the compounds herein disclosed are tankyrase inhibitors, e.g. inhibitors of tankyrase 1 and/or 2. This discovery leads to the use of the compounds to treat conditions or diseases in subjects, e.g. in humans, which are mediated by tankyrase, including WNT signalling related disorders, hippo signalling related disorders and other tankyrase 1 and/or 2 (TNKS1/TNKS2) signalling related disorders.

In one aspect the invention relates to compounds of general formula (I), their tautomers, stereoisomers, N-oxides, pharmaceutically acceptable salts and pro-drugs:

(I)

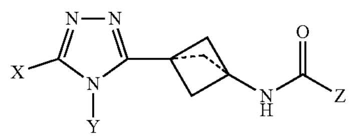

wherein:

a dashed line indicates an optional bond;

X represents:

- a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl);
- a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or
- an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);

Y represents:

- an aryl or heteroaryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);
- a 5- or 6-membered, saturated heterocyclic group optionally substituted by one or more (e.g. 1, 2 or 3) substituents independently selected from $C_{1-6}$ alkyl (preferably $C_1$-3 alkyl), $C_{1-6}$ haloalkyl (e.g. $C_{1-3}$ haloalkyl), and $C_{1-6}$ alkoxy (e.g. $C_{1-3}$ alkoxy); or
- a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and Z represents:

- an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); or
- an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring);

with the proviso:

- that when the compound is other than an N-oxide of formula (I), Z must be substituted by at least one substituent selected from —OH, —$N(R^1)_2$, —$SO_2N(R^3)_2$ and —$C(O)N(R^4)_2$, preferably by at least one substituent selected from —OH, —$SO_2N(R^3)_2$ and —$C(O)N(R^4)_2$.

As will be understood, in formula (I) the group:

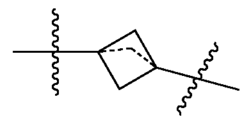

can be either one of the following groups:

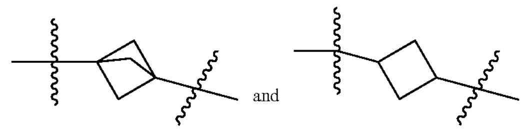 [SMILES: *C12CC(*)(C1)C2 ; *C1CC(*)C1]

In one embodiment the compounds according to the invention are those of formula (I) in which at least one tertiary nitrogen is present in the form of its corresponding N-oxide. In these compounds, group Z may be selected from any of the Z groups herein defined. Thus, in one embodiment, the invention provides an N-oxide of a compound of formula (Ia):

(Ia)

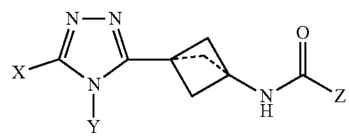

wherein:

a dashed line indicates an optional bond;

X and Y are as herein defined; and

Z is selected from the following:

- an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); and an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring).

In one embodiment the compounds according to the invention are those of general formula (I), or a tautomer, stereoisomer, N-oxide, pharmaceutically acceptable salt or pro-drug thereof, in which Z is substituted by at least one substituent selected from —OH, —$N(R^1)_2$, —$SO_2N(R^3)_2$ and —$C(O)N(R^4)_2$, preferably by at least one substituent selected from —OH, —$SO_2N(R^3)_2$ and —$C(O)N(R^4)_2$. In these compounds, group Z may additionally be substituted by one or more substituent groups selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$ and —$SO_2R^2$ (where $R^2$ is H or $C_{1-6}$ alkyl, e.g. H or $C_{1-3}$ alkyl). Thus, in another embodiment, the invention provides compounds of formula (Ib), their tautomers, stereoisomers, N-oxides, pharmaceutically acceptable salts and pro-drugs:

(Ib)

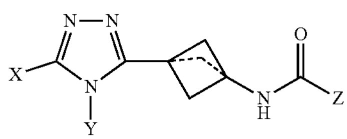

wherein:

a dashed line indicates an optional bond;

X and Y are as herein defined; and

Z is selected from the following:

an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); and an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring);

with the proviso:

that Z is substituted by at least one substituent (e.g. one or two substituents) selected from —OH, —$N(R^1)_2$, —$SO_2N(R^3)_2$ and —$C(O)N(R^4)_2$, preferably by at least one substituent (e.g. one or two substituents) selected from —OH, —$SO_2N(R^3)_2$ and —$C(O)N(R^4)_2$.

In one embodiment, the compounds according to the invention are those of formula (Ib) in which Z is substituted by 1 or 2 substituents selected from —OH, —$N(R^1)_2$, —$SO_2N(R^3)_2$ and —$C(O)N(R^4)_2$. In another embodiment, the compounds according to the invention are those of formula (Ib) in which Z is substituted by 1 or 2 substituents selected from —OH, —$SO_2N(R^3)_2$ and —$C(O)N(R^4)_2$.

In one embodiment the compounds of the invention are those of general formula (I), (Ia) or (Ib), wherein X represents:

a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl); or a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy).

In one embodiment, X is an optionally substituted, 5- or 6-membered, unsaturated heterocyclic group. Such groups will typically contain either at least one nitrogen atom, e.g. one or two nitrogen atoms, or one nitrogen atom and one sulphur atom. In an embodiment, X may be an optionally substituted heteroaryl group. Any substituent groups may be present either on a ring nitrogen or ring carbon atom. In another embodiment, X may be an unsubstituted.

X may, for example, be selected from any of the following groups: pyridinyl (e.g. 2-pyridinyl), pyrimidinyl (e.g. 2- or 4-pyrimidinyl), pyrrolyl (e.g. 2- or 3-pyrrolyl), pyrazinyl (e.g. 2-pyrazinyl), thiazolyl (e.g. 2- or 5-thiazolyl), pyrazolyl (e.g. 4-pyrazolyl), imidazolyl (e.g. 2-, 4- or 5-imidazoyle) and thiophenyl (e.g. 2-thiophenyl). Any of these groups may optionally be substituted by one or more of the substituent groups herein disclosed. In one embodiment, these groups may be unsubstituted.

Preferably, X is an optionally substituted pyridinyl or pyrimidinyl group, for example an optionally substituted 2-pyridinyl, 2-pyrimidinyl group or 4-pyrimidinyl group. In one embodiment, these groups may be unsubstituted.

In one embodiment, X may represent an optionally substituted $C_{3-5}$ cycloalkyl group, e.g. an unsubstituted $C_{3-5}$ cycloalkyl group. Examples of such groups include cyclopropyl and cyclopentyl.

In one embodiment, X may represent an optionally substituted aryl group, e.g. an optionally substituted phenyl group. For example, X may be an unsubstituted phenyl group.

Any of the X groups herein described may be substituted by one or more ring substituents. Where the groups X are substituted it is generally preferred that these are substituted by one or two substituent groups, e.g. by one substituent. Suitable substituents are as herein described and include, for example $C_{1-3}$ alkyl, $C_{1-3}$ alkoxy and $—SO_2R$ (where R is H or $C_{1-6}$ alkyl, preferably H or $C_{1-3}$ alkyl, e.g. methyl). Examples of suitable substitutents include $—OCH_2CH_3$ (and deuterated analogs), $—CH_3$ and $—SO_2CH_3$.

In one embodiment, X is unsubstituted.

Specific examples of group X include the following:

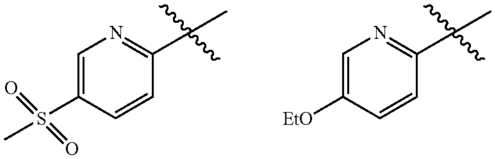
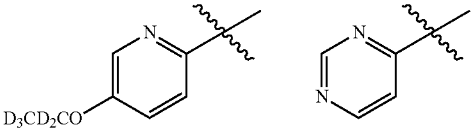
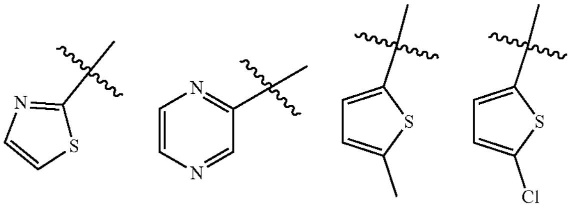
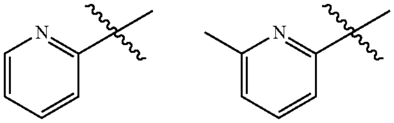
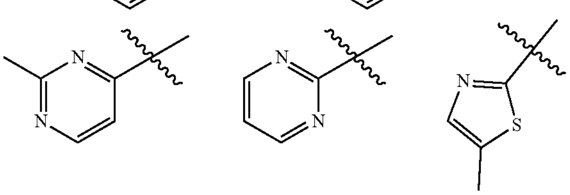
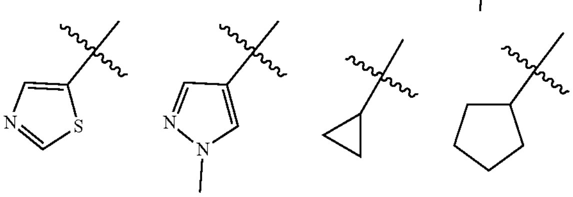
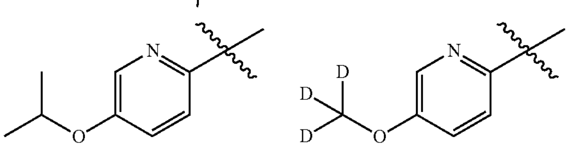

-continued

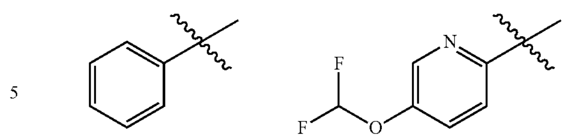

In one set of embodiments, group X may represent any of the following:

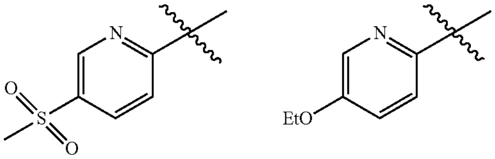
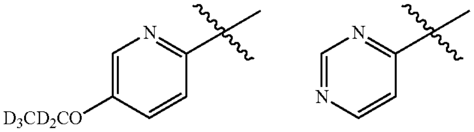
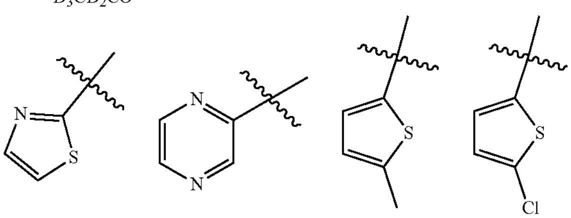
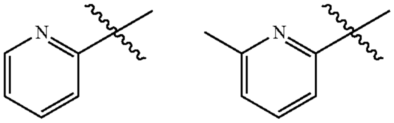
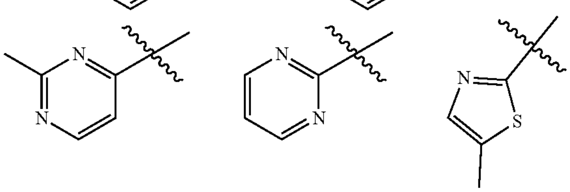
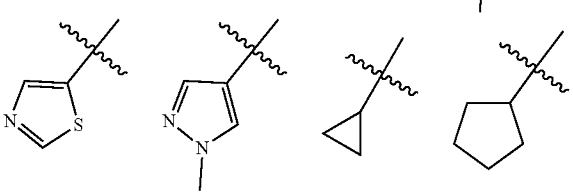
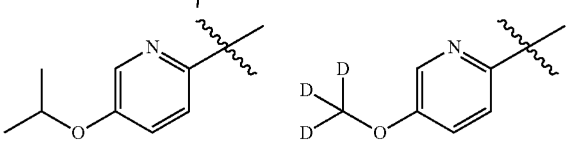

In certain embodiments, group X may be selected from any of the following:

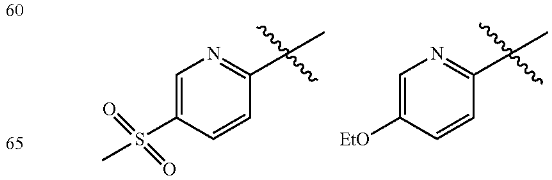

-continued

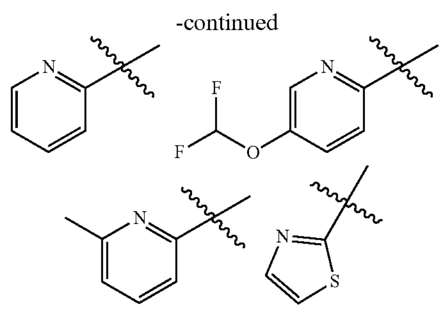

In one embodiment the compounds of the invention are those of general formula (I), (Ia) or (Ib), wherein Y is an optionally substituted aryl or heteroaryl group.

Where Y is an aryl group, this may be an optionally substituted phenyl group. When substituted, the ring substituents on the phenyl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. $—CF_3$), and halogen (e.g. F or Cl). One or more of such groups may be present on the ring in any ring positions. However, it is preferred that one or two groups will be present. In one embodiment, the phenyl ring will be substituted by a single halogen atom (e.g. F or Cl) either in the ortho-, meta- or para-position, e.g. in the ortho-position.

In another embodiment, Y represents an optionally substituted heteroaryl group. Such groups will typically contain one or two heteroatoms, e.g. one heteroatom. Preferably, the heteroatom is either nitrogen or sulphur, e.g. nitrogen. Where the ring is 6-membered the heteroatom is preferably nitrogen. Where the ring is 5-membered the heteroatom is preferably sulphur. In one embodiment, Y represents pyridinyl, e.g. 2-pyridinyl. In a further embodiment, Y can be thiophenyl (e.g. 2-thiophenyl). When substituted, the ring substituents on the heteroaryl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. $—CF_3$), and halogen (e.g. F or Cl). One or more of such groups may be present on the ring in any ring positions. In one embodiment, a single substituent may be present.

Preferably Y may be an optionally substituted phenyl, pyridinyl (e.g. 2-pyridinyl) or thiophenyl (e.g. 2-thiophenyl) group.

In one embodiment, Y may represent a 5- or 6-membered, saturated heterocyclic group. This group may be substituted or unsubstituted, preferably it will be unsubstituted. Such groups will typically contain one or two heteroatoms, e.g. one heteroatom. Preferably the heteroatom is oxygen. An example of such a group is tetrahydropyranyl.

In another embodiment, Y may represent an optionally substituted $C_{3-6}$ cycloalkyl group. When substituted, suitable substituent groups include $C_{1-6}$ alkyl (e.g. $C_{1-3}$ alkyl). In one embodiment, the cycloalkyl ring may be unsubstituted. Examples of such groups include cyclopentyl and cyclohexyl.

Any of the Y groups herein described may be substituted by one or more ring substituents. Where these are substituted it is generally preferred that these are substituted by one or two substituent groups, e.g. by one substituent. Suitable substituents are as herein described and include, for example $C_{1-3}$ alkyl, $C_{1-3}$ alkoxy, $C_{1-3}$ haloalkyl, and halogen atoms. Examples of suitable substitutents include F, Cl, $C_{1-3}$ alkyl, and $—CF_3$.

In one embodiment, Y is unsubstituted.

Specific examples of group Y include the following:

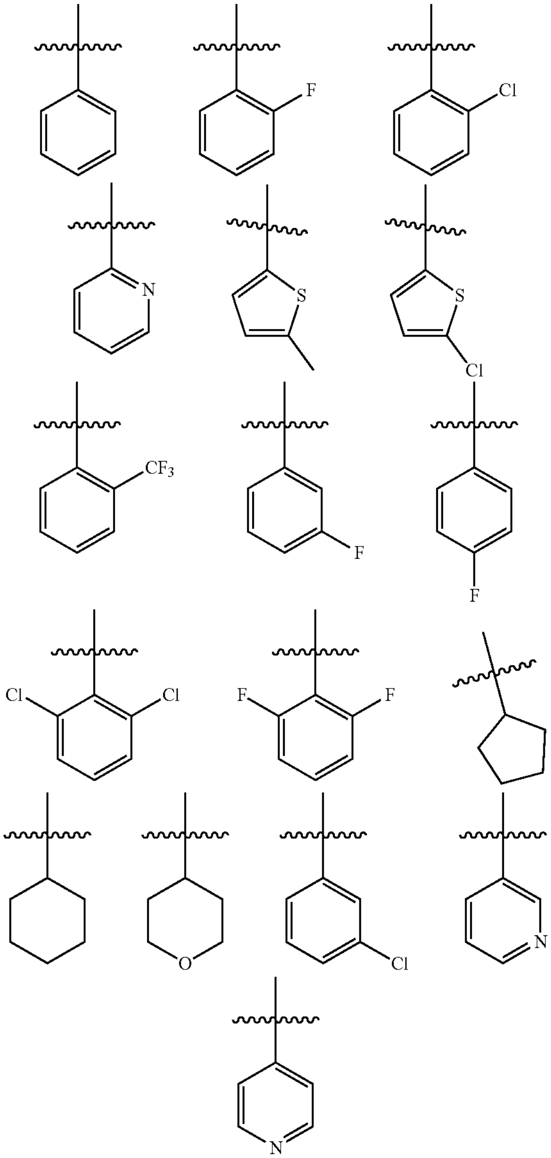

In certain embodiments, group Y may be selected from any of the following:

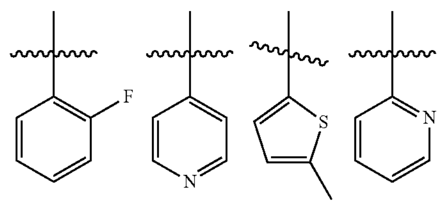

In one embodiment the compounds of the invention are those of general formula (I), (Ia) or (Ib), wherein Z represents an aryl group optionally substituted by one or more (e.g. 1, 2 or 3) substituents.

In one embodiment, Z is an optionally substituted phenyl or naphthyl group. When substituted, the ring substituents on the phenyl or naphthyl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. —$CF_3$), halogen (e.g. F or Cl), —OH, —$NH_2$, —NH($C_{1-3}$ alkyl) (e.g. —$NHCH_3$ or —NH($C_2H_5$)), —N($C_{1-3}$ alkyl)$_2$ (e.g. —N($CH_3$)$_2$ or —N($C_2H_5$)$_2$), —$SO_2NH_2$, —$SO_2$NH($C_{1-3}$ alkyl) (e.g. —$SO_2$NH($CH_3$) or —$SO_2$NH($C_2H_5$)), —$SO_2$N($C_{1-3}$ alkyl)$_2$ (e.g. —$SO_2$N($CH_3$)$_2$ or —$SO_2$N($C_2H_5$)$_2$), —C(O)$NH_2$, —C(O)NH($C_{1-3}$ alkyl) (e.g. —C(O)$NHCH_3$ or —C(O)NH($C_2H_5$)), —C(O)N($C_{1-3}$ alkyl)$_2$ (e.g. —C(O)N($CH_3$)$_2$ or —C(O)N($C_2H_5$)$_2$), or —C(O)N($R^4$)$_2$ wherein both $R^4$ groups, together with the intervening nitrogen atom, form a 3 to 6 membered saturated heterocyclic ring (e.g. a 3 or 4 membered saturated heterocyclic ring). One or more of such groups may be present on the ring in any ring positions. However, it is preferred that one or two groups will be present.

In one embodiment, the phenyl or naphthyl ring will be substituted by a single halogen atom (e.g. F or Cl) either in the ortho-, meta- or para-position. In another embodiment, the phenyl or naphthyl ring may be unsubstituted.

In one embodiment, the phenyl or naphthyl ring will be substituted by one or more groups (e.g. by one or two groups) selected from —OH, —$NH_2$, —NH($C_{1-3}$ alkyl) (e.g. —$NHCH_3$ or —NH($C_2H_5$)), —N($C_{1-3}$ alkyl)$_2$ (e.g. —N($CH_3$)$_2$ or —N($C_2H_5$)$_2$), —$SO_2NH_2$, —$SO_2$NH($C_{1-3}$ alkyl) (e.g. —$SO_2$NH($CH_3$) or —$SO_2$NH($C_2H_5$)), —$SO_2$N($C_{1-3}$ alkyl)$_2$ (e.g. —$SO_2$N($CH_3$)$_2$ or —$SO_2$N($C_2H_5$)$_2$), —C(O)$NH_2$, —C(O)NH($C_{1-3}$ alkyl) (e.g. —C(O)$NHCH_3$ or —C(O)NH($C_2H_5$)), —C(O)N($C_{1-3}$ alkyl)$_2$ (e.g. —C(O)N($CH_3$)$_2$ or —C(O)N($C_2H_5$)$_2$), and —C(O)N($R^4$)$_2$ wherein both $R^4$ groups, together with the intervening nitrogen atom, form a 3 to 6 membered saturated heterocyclic ring (e.g. a 3 or 4 membered saturated heterocyclic ring).

In one embodiment, the ring substituents on the phenyl or naphthyl ring are independently selected from —OH, —$SO_2$N($R^3$)$_2$ and —C(O)N($R^4$)$_2$ (where $R^3$ and $R^4$ are as herein defined). In one embodiment, the ring substituents are independently selected from —OH, —$SO_2NH_2$, —$SO_2$NH($C_{1-3}$ alkyl) (e.g. —$SO_2$NH($CH_3$) or —$SO_2$NH($C_2H_5$)), —$SO_2$N($C_{1-3}$ alkyl)$_2$ (e.g. —$SO_2$N($CH_3$)$_2$ or —$SO_2$N($C_2H_5$)$_2$), —C(O)$NH_2$, —C(O)NH($C_{1-3}$ alkyl) (e.g. —C(O)$NHCH_3$ or —C(O)NH($C_2H_5$)), —C(O)N($C_{1-3}$ alkyl)$_2$ (e.g. —C(O)N($CH_3$)$_2$ or —C(O)N($C_2H_5$)$_2$), or —C(O)N($R^4$)$_2$ wherein both $R^4$ groups, together with the intervening nitrogen atom, form a 3 to 6 membered saturated heterocyclic ring (e.g. a 3 or 4 membered saturated heterocyclic ring).

In one embodiment, Z is a phenyl or naphthyl ring substituted by one or more —OH groups, e.g. by 1 or 2 —OH groups. In one embodiment, Z is a phenyl or naphthyl ring substituted by a single —OH group.

In one embodiment the compounds of the invention are those of general formula (I), (Ia) or (Ib), wherein Z represents an optionally substituted, unsaturated, 5- to 10-membered mono- or bicyclic heterocyclic group. Such groups containing one or more nitrogen atoms, e.g. one or two nitrogen atoms, are preferred. For example, Z may represent a 6-membered, 5-5 fused, 5-6 fused, or 6-6 fused unsaturated heterocyclic ring containing one, two or three heteroatoms, e.g. one, two, or three nitrogen atoms, preferably one or two nitrogen atoms. When substituted, the substituents may independently be selected from $C_{1-3}$ alkyl (e.g. methyl or ethyl), $C_{1-3}$ alkoxy (e.g. methoxy or ethoxy), $C_{1-3}$ haloalkyl (e.g. —$CF_3$), halogen (e.g. F or Cl), —OH, —$NH_2$, —NH($C_{1-3}$ alkyl) (e.g. —$NHCH_3$ or —NH($C_2H_5$)), —N($C_{1-3}$ alkyl)$_2$ (e.g. —N($CH_3$)$_2$ or —N($C_2H_5$)$_2$), —$SO_2NH_2$, —$SO_2$NH($C_{1-3}$ alkyl) (e.g. —$SO_2$NH($CH_3$) or —$SO_2$NH($C_2H_5$)), —$SO_2$N($C_{1-3}$ alkyl)$_2$ (e.g. —$SO_2$N($CH_3$)$_2$ or —$SO_2$N($C_2H_5$)$_2$), —C(O)$NH_2$, —C(O)NH($C_{1-3}$ alkyl) (e.g. —C(O)$NHCH_3$ or —C(O)NH($C_2H_5$)), —C(O)N($C_{1-3}$ alkyl)$_2$ (e.g. —C(O)N($CH_3$)$_2$ or —C(O)N($C_2H_5$)$_2$), or —C(O)N($R^4$)$_2$ wherein both $R^4$ groups, together with the intervening nitrogen atom, form a 3 to 6 membered saturated heterocyclic ring (e.g. a 3 or 4 membered saturated heterocyclic ring). One or more of such groups may be present in any ring positions. However, it is preferred that one or two groups will be present.

Z may, for example, be selected from any of the following groups:

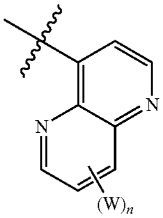
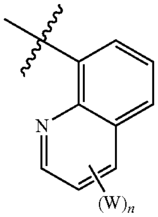
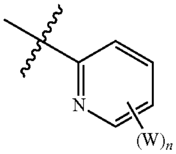
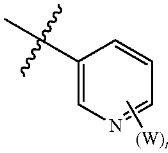
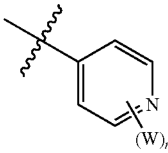
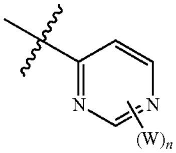
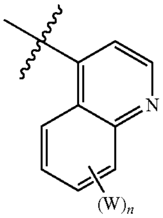
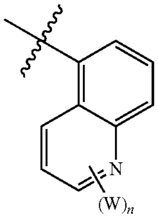
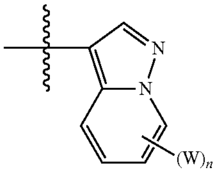
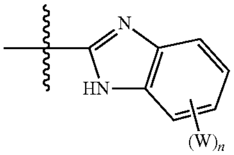
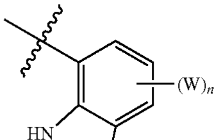
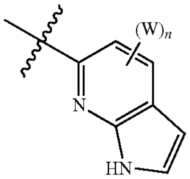
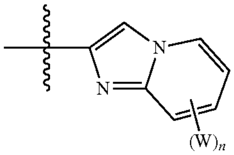
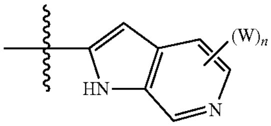
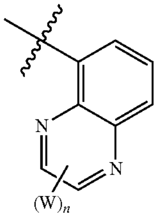

-continued

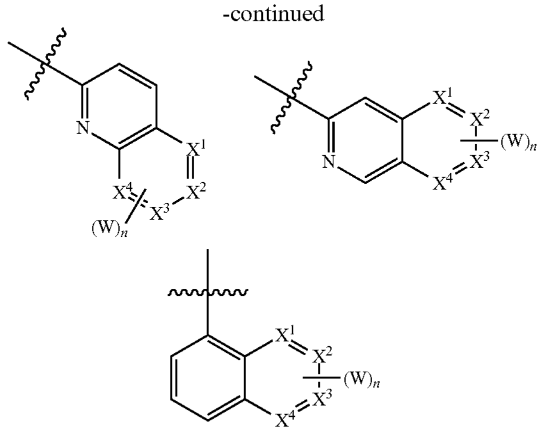

wherein n is 0, 1, or 2, preferably 0 or 1;

W is a substituent group selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH; or two of $X^1$, $X^2$, $X^3$ and $X^4$ (e.g. $X^1$ and $X^4$) are N and the remaining two of $X^1$, $X^2$, $X^3$ and $X^4$ (e.g. $X^2$ and $X^3$) are CH.

In one set of embodiments, group Z may be selected from any of the following groups:

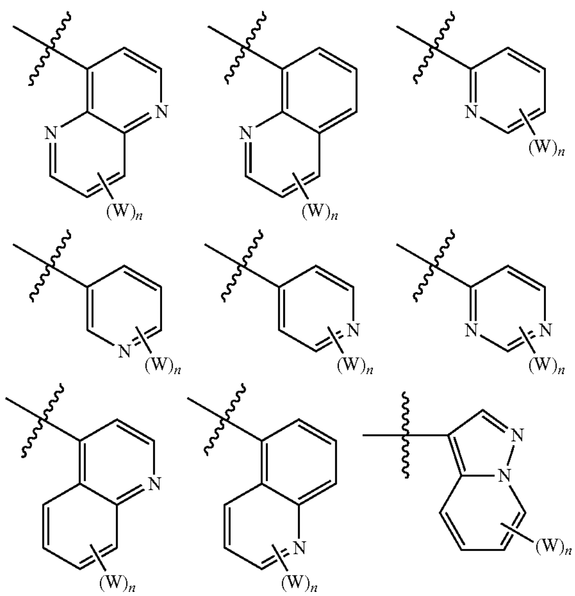

-continued

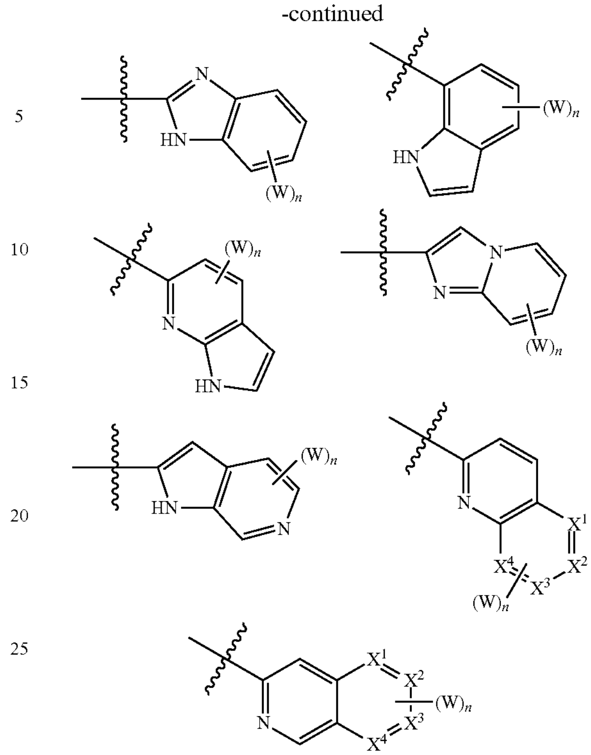

wherein n is 0, 1 or 2, preferably 0 or 1;

W is a substituent group selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —OH, —$N(R^1)_2$ (where each $R^1$ is independently H or $C_{1-6}$ alkyl, e.g. H or $C_{1-3}$ alkyl), —$SO_2R^2$ (where $R^2$ is H or $C_{1-6}$ alkyl, e.g. H or $C_{1-3}$ alkyl), —$SO_2N(R^3)_2$ (where each $R^3$ is independently H or $C_{1-6}$ alkyl, e.g. H or $C_{1-3}$ alkyl), and —$C(O)N(R^4)_2$ (where each $R^4$ is independently H or $C_{1-6}$ alkyl, e.g. H or $C_{1-3}$ alkyl, or wherein both $R^4$ groups, together with the intervening nitrogen atom, form a 3 to 6 membered saturated heterocyclic ring); and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH.

In one embodiment, n is 0.

Where n is 1 or 2, each W may preferably be selected from halogen (e.g. F or Cl), $C_{1-3}$ alkyl, $C_{1-3}$ alkoxy, —CN, —OH, —$NH_2$, —$NH(C_{1-3}$ alkyl) (e.g. —$NHCH_3$ or —$NH(C_2H_5)$), —$N(C_{1-3}$ alkyl$)_2$ (e.g. —$N(CH_3)_2$ or —$N(C_2H_5)_2$), —$SO_2NH_2$, —$SO_2NH(C_{1-3}$ alkyl) (e.g. —$SO_2NH(CH_3)$ or —$SO_2NH(C_2H_5)$), —$SO_2N(C_{1-3}$ alkyl$)_2$ (e.g. —$SO_2N(CH_3)_2$ or —$SO_2N(C_2H_5)_2$), —$C(O)NH_2$, —$C(O)NH(C_{1-3}$ alkyl) (e.g. —$C(O)NHCH_3$ or —$C(O)NH(C_2H_5)$), —$C(O)N(C_{1-3}$ alkyl$)_2$ (e.g. —$C(O)N(CH_3)_2$ or —$C(O)N(C_2H_5)_2$), or —$C(O)N(R^4)_2$ wherein both $R^4$ groups, together with the intervening nitrogen atom, form a 3 to 6 membered saturated heterocyclic ring (e.g. a 3 or 4 membered saturated heterocyclic ring).

In one embodiment, Z is selected from optionally substituted phenyl, naphthyl, pyridinyl (e.g. 2-, 3- or 4-pyridinyl, preferably 2- or 3-pyridinyl), pyrimidinyl (e.g. 2- or 4-pyrimidiyl, preferably 4-pyrimidiyl), quinolinyl (e.g. 4-, 5- or 8-quinolinyl), 1,5-naphthyridinyl (e.g. 4-(1,5-naphthyridinyl)), benzimidazolyl (e.g. 2-benzimidazolyl), pyrazolo[1, 5-a]pyridinyl (e.g. 3-(pyrazolo[1,5-a]pyridinyl)), diazanaphthalenyl (e.g. a naphthyridinyl, such as a 1,8-, 1,6- and 1,4-naphthyridinyl, or a benzodiazinyl, such as a 1,4-diazanaphthalenyl), an azaindolyl (e.g. a 4-, 5- or 7-azaindolyl), 1H-indolyl, furopyrrolyl (e.g. 4H-furo[3,2-6] pyrrolyl), and thienopyrrolyl (e.g. a 4-thieno[3,2-6] pyrrolyl). In another embodiment, Z is selected from optionally substituted phenyl, naphthyl, pyridinyl, quinolinyl, 1,5-naphthyridinyl and 1,4-diazanaphthalenyl.

Z is preferably selected from optionally substituted phenyl, naphthyl, pyridinyl (e.g. 2-, 3- or 4-pyridinyl, preferably 2- or 3-pyridinyl), pyrimidinyl (e.g. 2- or 4-pyrimidinyl, preferably 4-pyrimidinyl), quinolinyl (e.g. 4-, 5- or 8-quinolinyl), 1,5-naphthyridinyl (e.g. 4-(1,5-napthyridinyl)), benzimidazolyl (e.g. 2-benzimidazolyl), pyrazolo[1,5-a] pyridinyl (e.g. 3-(pyrazolo[1,5-a]pyridinyl)) and quinoxalinyl (e.g. 5-quinoxalinyl). More preferably, Z is selected from optionally substituted phenyl, naphthyl, pyridinyl, quinolinyl and quinoxalinyl.

In a further embodiment, Z is selected from optionally substituted phenyl, naphthyl, 5-quinolinyl, 8-quinolinyl, 2-pyridinyl and 5-quinoxalinyl.

Any of the Z groups herein described may be substituted by one or more ring substituents. Where these are substituted it is generally preferred that these are substituted by one or two substituent groups, e.g. by one substituent. Suitable substituents are as herein described and include, for example $C_{1-3}$ alkyl, $C_{1-3}$ alkoxy, $C_{1-3}$ haloalkyl, —CN and halogen atoms, —OH, —$NH_2$, —$NH(C_{1-3}$ alkyl) (e.g. —$NHCH_3$ or —$NH(C_2H_5)$), —$N(C_{1-3}$ alkyl$)_2$ (e.g. —$N(CH_3)_2$) or —$N(C_2H_5)_2$), —$SO_2NH_2$, —$SO_2NH(C_{1-3}$ alkyl) (e.g. —$SO_2NH(CH_3)$ or —$SO_2NH(C_2H_5)$), —$SO_2N(C_{1-3}$ alkyl$)_2$ (e.g. —$SO_2N(CH_3)_2$ or —$SO_2N(C_2H_5)_2$), —$C(O)NH_2$, —$C(O)NH(C_{1-3}$ alkyl) (e.g. —$C(O)NHCH_3$ or —$C(O)NH(C_2H_5)$), —$C(O)N(C_{1-3}$ alkyl$)_2$ (e.g. —$C(O)N(CH_3)_2$ or —$C(O)N(C_2H_5)_2$), or —$C(O)N(R^4)_2$ wherein both $R^4$ groups, together with the intervening nitrogen atom, form a 3 to 6 membered saturated heterocyclic ring (e.g. a 3 or 4 membered saturated heterocyclic ring). Preferred examples of suitable substituents include F, CN, —$OCH_3$, —$OCH_2CH_3$, —OH, —$NH_2$, —$SO_2NH_2$, —$C(O)NH_2$, —$C(O)NHCH_3$, —$C(O)N(CH_3)_2$, and

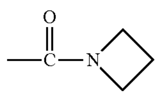

In one embodiment, Z is unsubstituted.

Specific examples of group Z include the following:

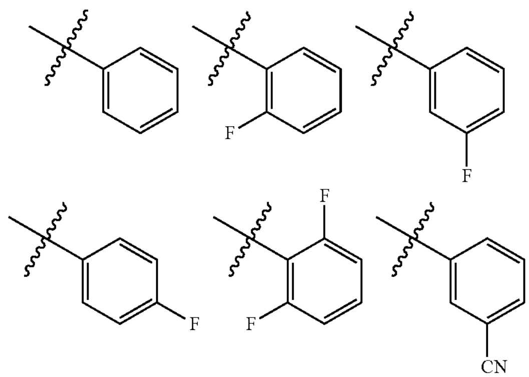

-continued

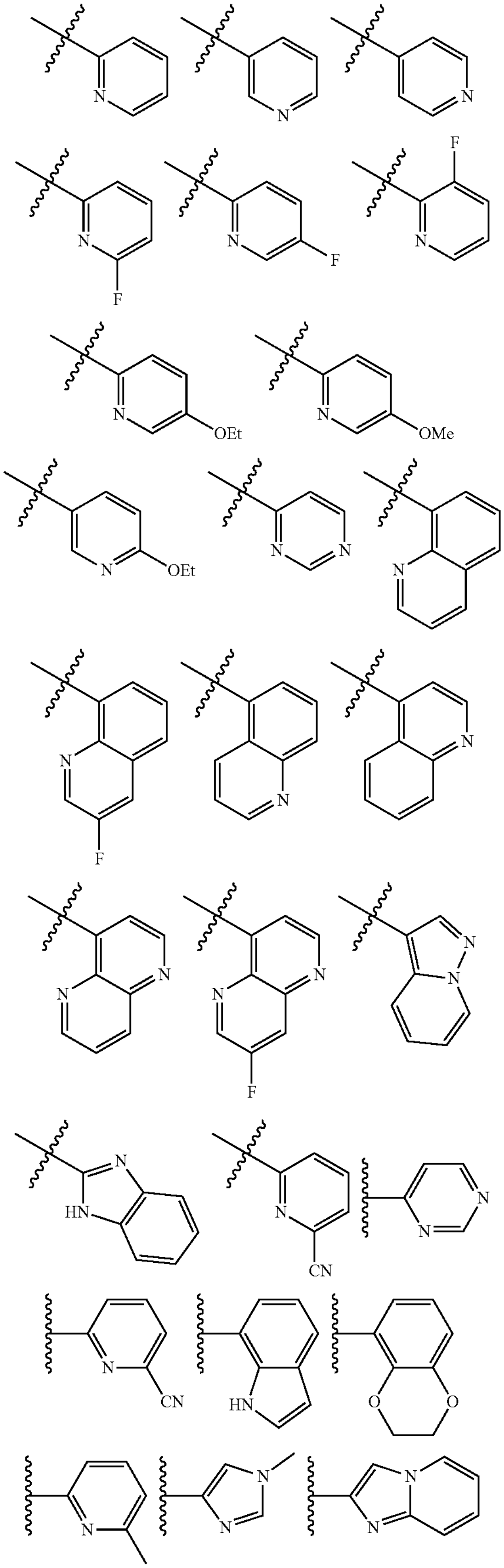

-continued
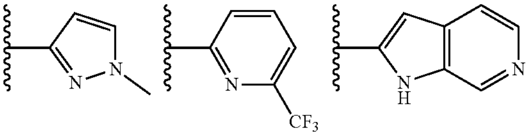
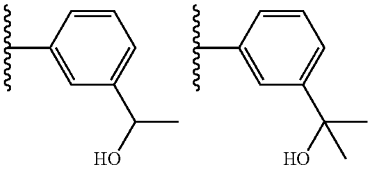
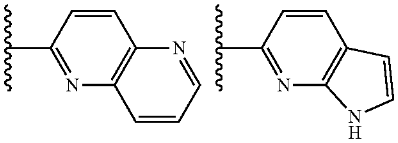
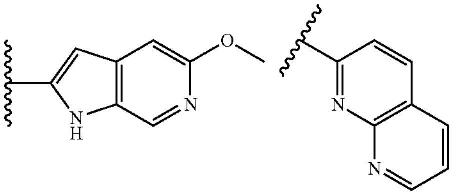
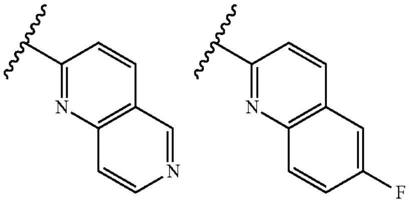
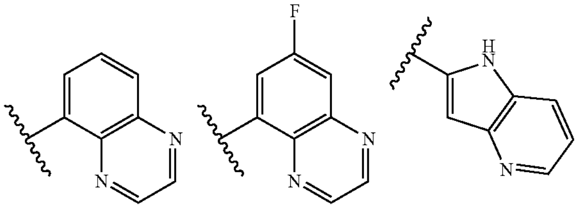
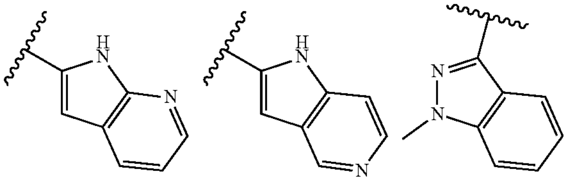
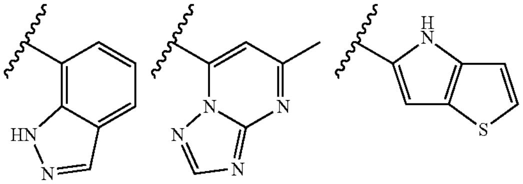
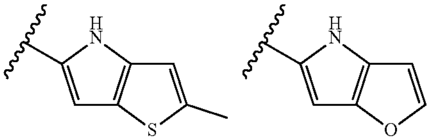
-continued
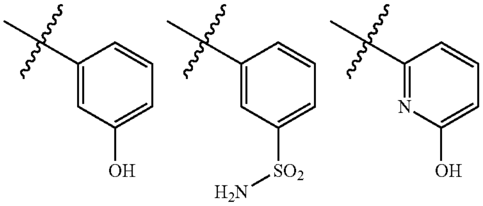
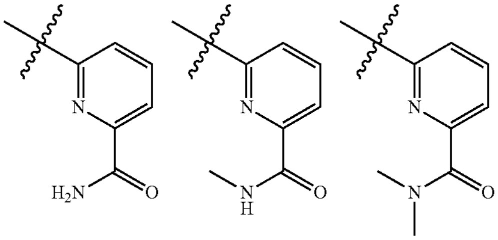
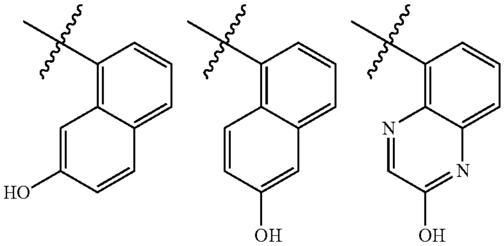
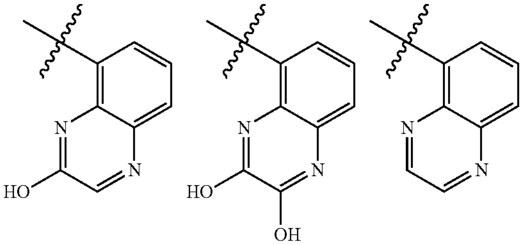
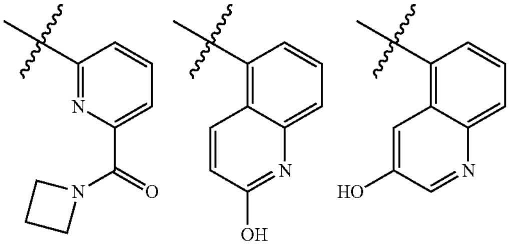
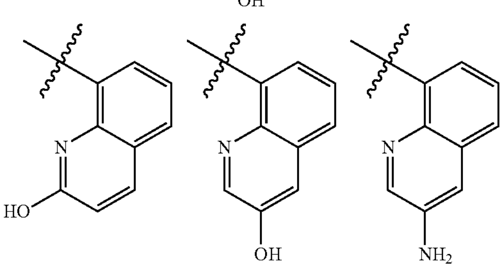
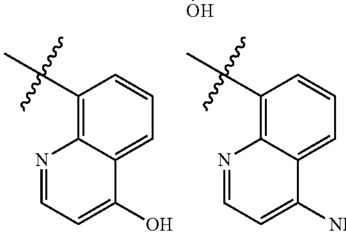

In certain embodiments, examples of group Z include the following:
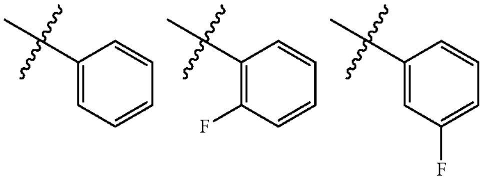
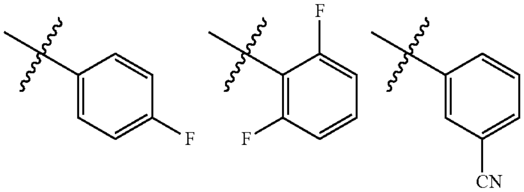
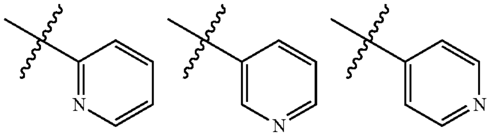
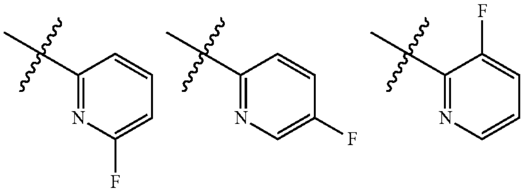
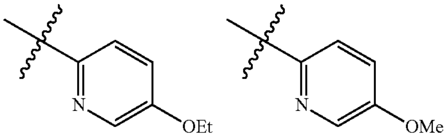
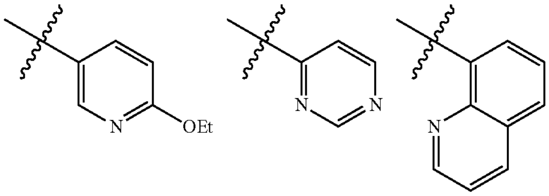
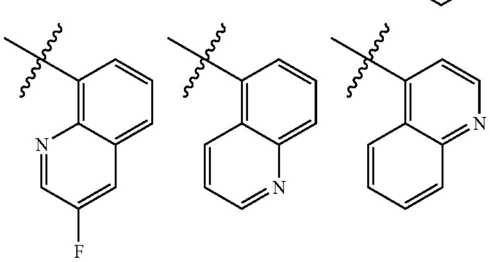
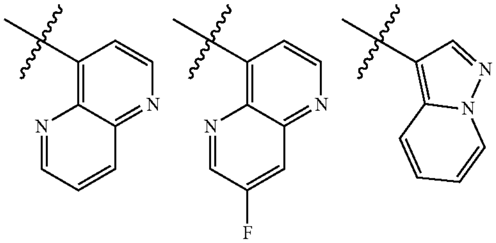
-continued
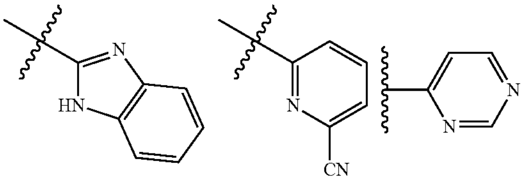
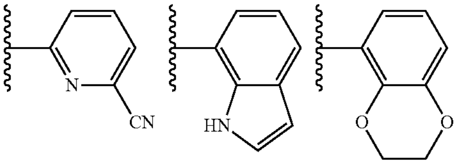
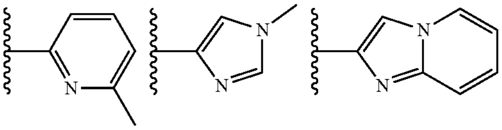
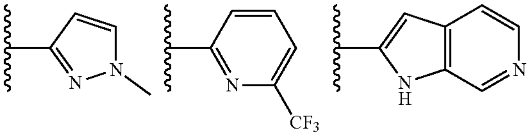
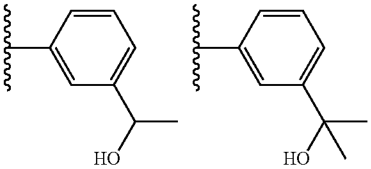
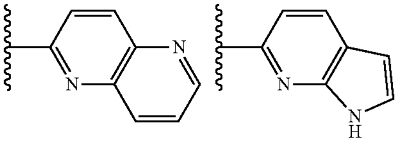
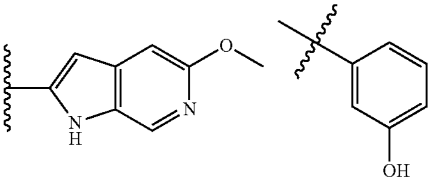
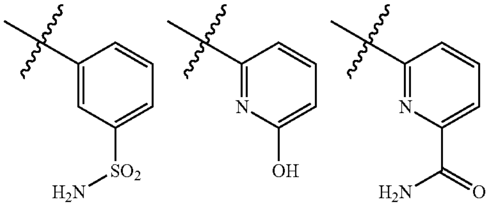
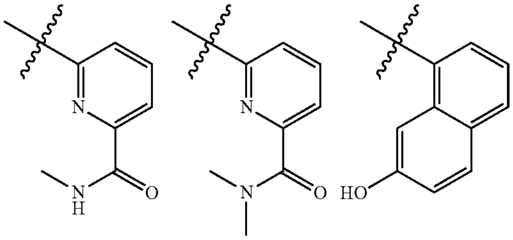

-continued

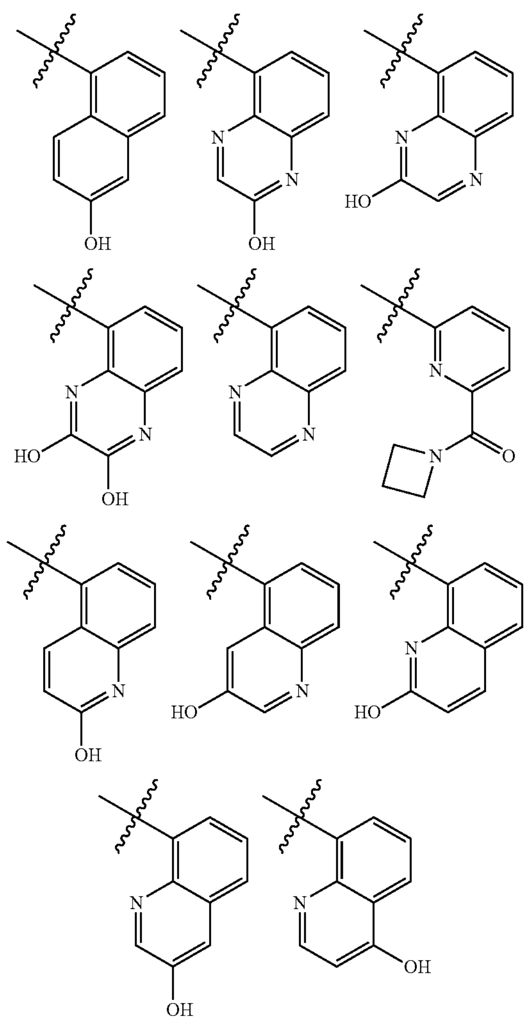

In another embodiment, examples of group Z include the following:

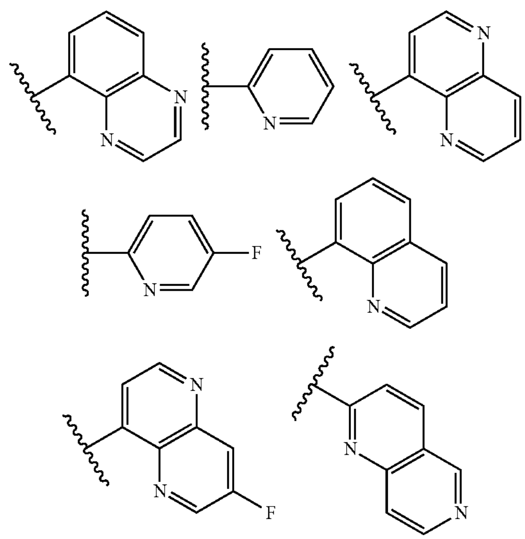

-continued

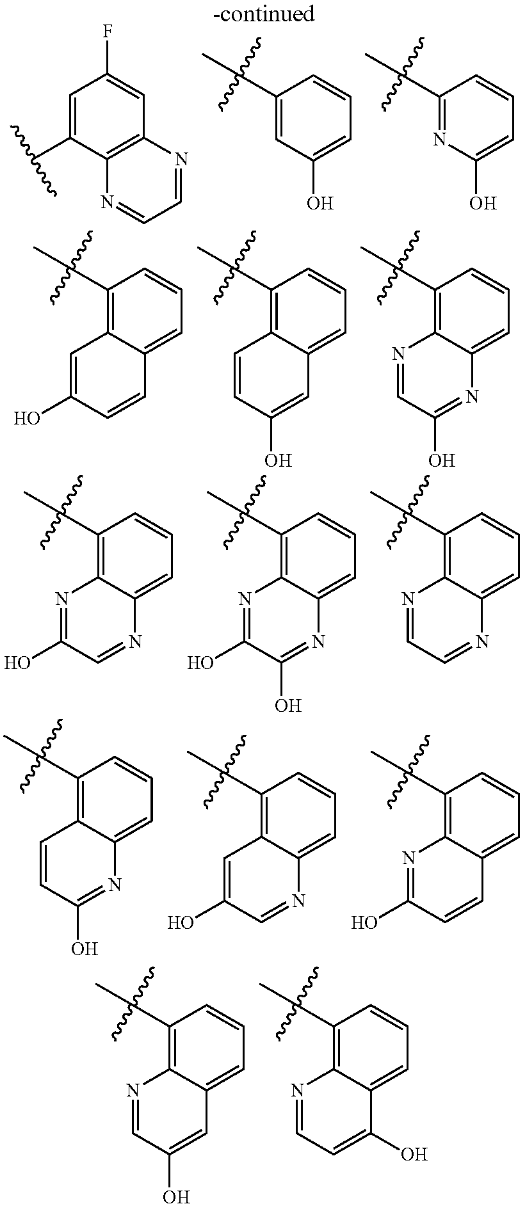

In one embodiment the compounds according to the invention are provided in the form of an N-oxide. In this aspect of the invention, at least one of the tertiary ring nitrogen atoms present in any of the nitrogen-containing heterocyclic groups herein described for groups X and Z may be present in the form of an N-oxide.

In one embodiment, at least one (e.g. one) of the tertiary ring nitrogen atoms present in group X may be provided in the form of an N-oxide. For example, group X may be an optionally substituted pyridinyl (e.g. an optionally substituted 2-pyridinyl) in which the ring nitrogen is present as an N-oxide.

In one embodiment, at least one (e.g. one) of the ring nitrogen atoms present in group Z may be provided in the form of an N-oxide. For example, group Z may be an optionally substituted 6-membered, 5-5 fused, 5-6 fused, or 6-6 fused unsaturated heterocyclic ring containing one, two, or three nitrogen atoms, preferably one or two nitrogen atoms, in which at least one of the tertiary ring nitrogen atoms is provided in the form of an N-oxide. In one embodiment, the heterocyclic ring is unsubstituted.

In one set of embodiments, group Z may be selected from any of the following groups in which one of the tertiary ring nitrogen is shown in the form of an N-oxide:

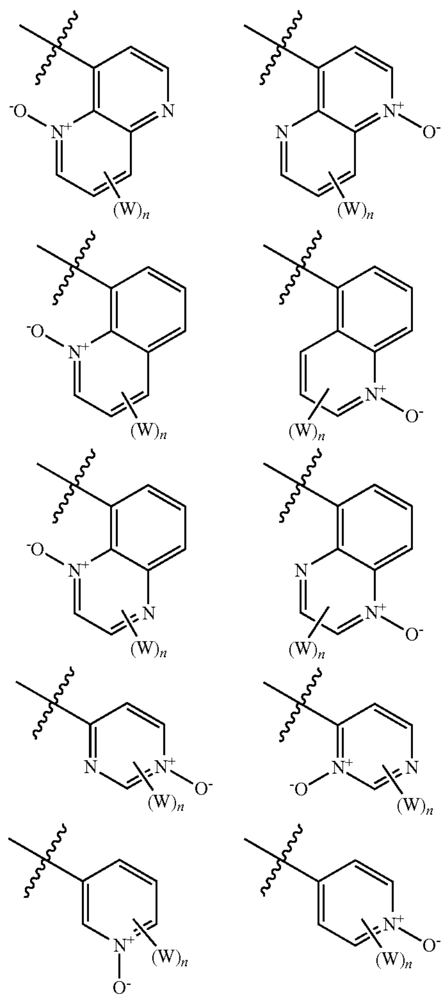

-continued

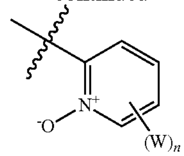

In these groups, n is 0, 1 or 2, preferably 0 or 1; and W is a substituent group selected from any of those described herein.

As will be understood, the compounds described herein may exist in various stereoisomeric forms, including enantiomers, diastereomers, and mixtures thereof. The invention encompasses all optical isomers of the compounds described herein and mixtures of optical isomers. Hence, compounds that exist as diastereomers, racemates and/or enantiomers are within the scope of the invention. In particular, the invention extends to the enantiomers, diastereomers, and mixtures of diastereomers and/or enantiomers, of any of the compounds having a chiral centre.

In particular, the invention extends to the enantiomers, diastereomers, and mixtures of diastereomers and/or enantiomers of any of the compounds herein described having a chiral centre in the cyclobutyl or bridged cyclobutyl linking moiety. In one embodiment the bonds between this linking moiety and the remainder of the molecule are in a trans-relationship. Thus, in one embodiment, the compounds of the invention may have the following general formula (I'):

(I')

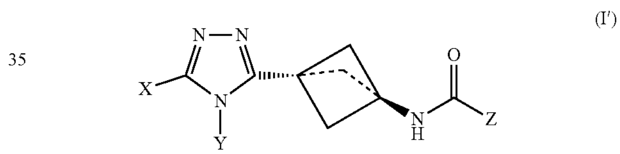

wherein X, Y and Z are as herein defined.

Examples of compounds according to the invention include the following, their tautomers, stereoisomers, N-oxides, pharmaceutically acceptable salts and pro-drugs:

| Example No. (where appropriate) | Structure |
|---|---|
| 1 | 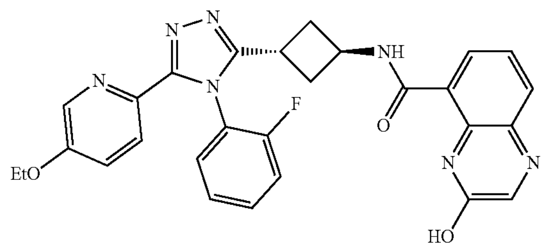 [SMILES: CCOc1ccc(-c2nnc([C@H]3C[C@H](NC(=O)c4cccc5ncc(O)nc45)C3)n2-c2ccccc2F)nc1] |

-continued
| Example No. (where appropriate) | Structure |
|---|---|
| 2 | 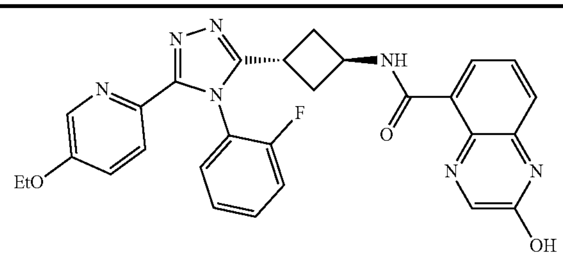 |
| 3 | 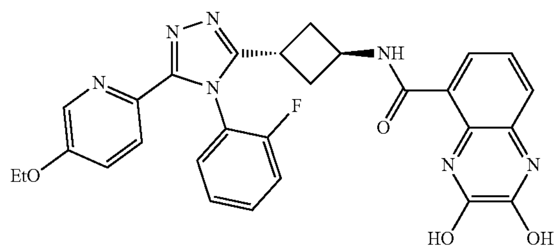 [SMILES: CCOc1ccc(-c2nnc([C@H]3C[C@H](NC(=O)c4cccc5nc(O)c(O)nc45)C3)n2-c2ccccc2F)nc1] |
| 4 | 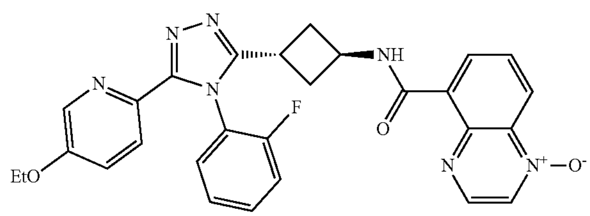 [SMILES: CCOc1ccc(-c2nnc([C@H]3C[C@H](NC(=O)c4cccc5c4ncc[n+]5[O-])C3)n2-c2ccccc2F)nc1] |
| 5 | 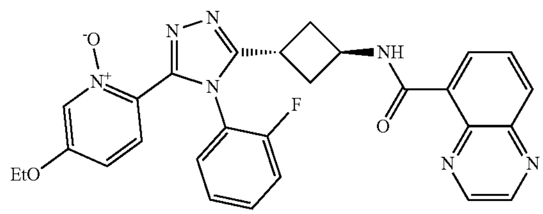 |
| 15 | 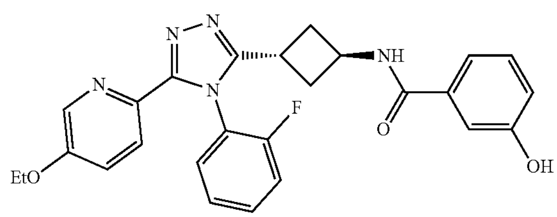 [SMILES: CCOc1ccc(-c2nnc([C@H]3C[C@H](NC(=O)c4cccc(O)c4)C3)n2-c2ccccc2F)nc1] |
| 16 | 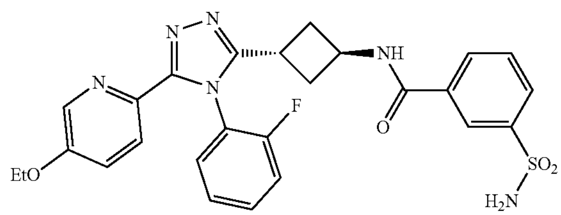 [SMILES: CCOc1ccc(-c2nnc([C@H]3C[C@H](NC(=O)c4cccc(S(N)(=O)=O)c4)C3)n2-c2ccccc2F)nc1] |
| — | 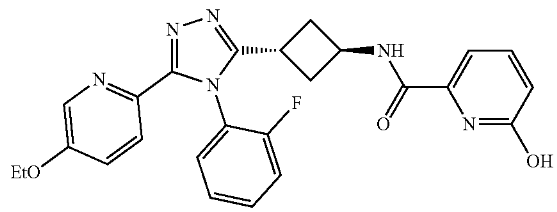 [SMILES: CCOc1ccc(-c2nnc([C@H]3C[C@H](NC(=O)c4cccc(O)n4)C3)n2-c2ccccc2F)nc1] |

-continued
| Example No. (where appropriate) | Structure |
|---|---|
| 7 | 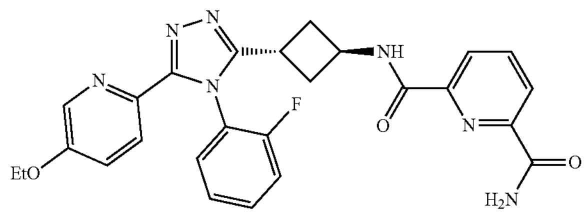 [SMILES: CCOc1ccc(-c2nnc([C@H]3C[C@H](NC(=O)c4cccc(C(N)=O)n4)C3)n2-c2ccccc2F)nc1] |
| 8 | 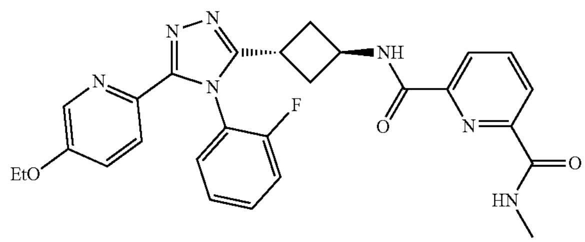 [SMILES: CCOc1ccc(-c2nnc([C@H]3C[C@H](NC(=O)c4cccc(C(=O)NC)n4)C3)n2-c2ccccc2F)nc1] |
| 9 | 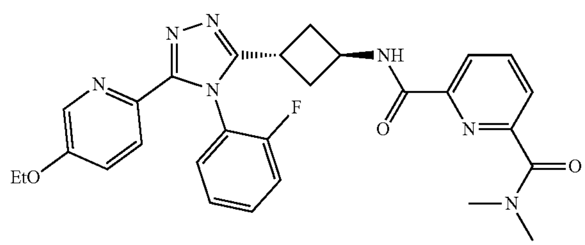 [SMILES: CCOc1ccc(-c2nnc([C@H]3C[C@H](NC(=O)c4cccc(C(=O)N(C)C)n4)C3)n2-c2ccccc2F)nc1] |
| — | 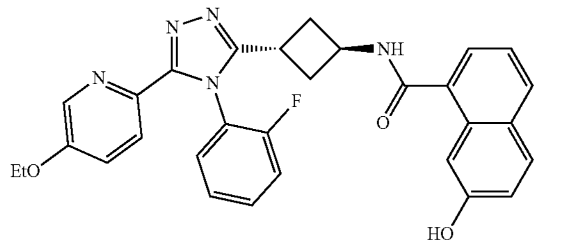 [SMILES: CCOc1ccc(-c2nnc([C@H]3C[C@H](NC(=O)c4cccc5ccc(O)cc45)C3)n2-c2ccccc2F)nc1] |
| 12 | 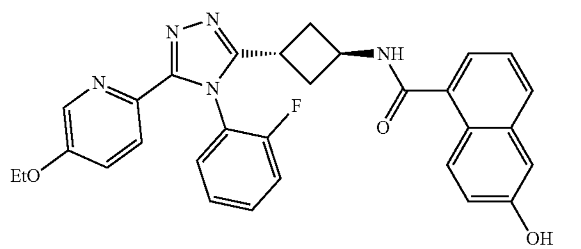 [SMILES: CCOc1ccc(-c2nnc([C@H]3C[C@H](NC(=O)c4cccc5cc(O)ccc45)C3)n2-c2ccccc2F)nc1] |
| 10 | 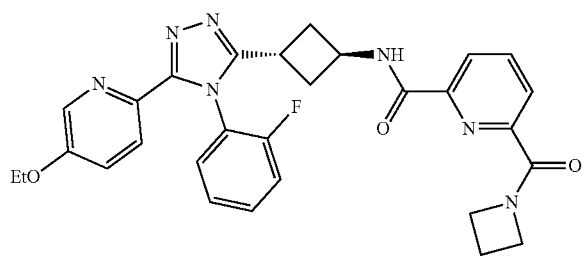 [SMILES: CCOc1ccc(-c2nnc([C@H]3C[C@H](NC(=O)c4cccc(C(=O)N5CCC5)n4)C3)n2-c2ccccc2F)nc1] |

-continued
| Example No. (where appropriate) | Structure |
| --- | --- |
| — | 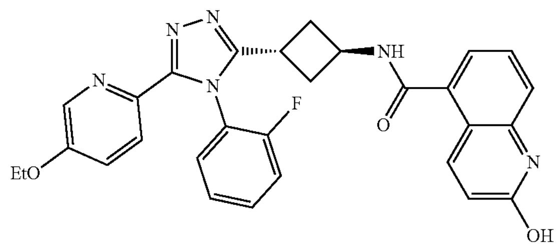 [SMILES: CCOc1ccc(-c2nnc([C@H]3C[C@H](NC(=O)c4cccc5nc(O)ccc45)C3)n2-c2ccccc2F)nc1] |
| — | 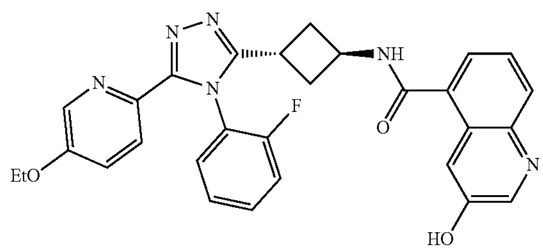 [SMILES: CCOc1ccc(-c2nnc([C@H]3C[C@H](NC(=O)c4cccc5ncc(O)cc45)C3)n2-c2ccccc2F)nc1] |
| — | 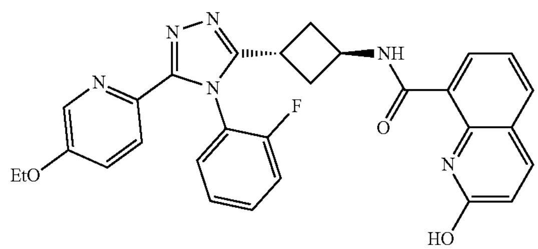 [SMILES: CCOc1ccc(-c2nnc([C@H]3C[C@H](NC(=O)c4cccc5ccc(O)nc45)C3)n2-c2ccccc2F)nc1] |
| 23 | 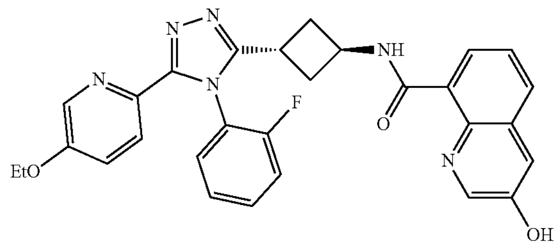 [SMILES: CCOc1ccc(-c2nnc([C@H]3C[C@H](NC(=O)c4cccc5cc(O)cnc45)C3)n2-c2ccccc2F)nc1] |
| — | 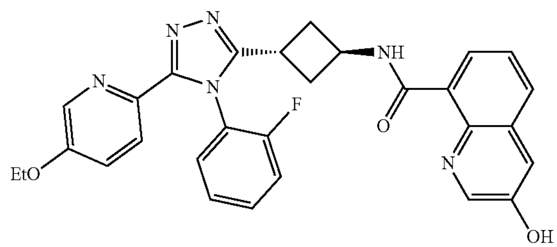 [SMILES: CCOc1ccc(-c2nnc([C@H]3C[C@H](NC(=O)c4cccc5cc(O)cnc45)C3)n2-c2ccccc2F)nc1] |
| 14 | 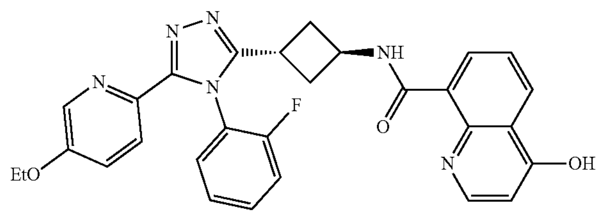 [SMILES: CCOc1ccc(-c2nnc([C@H]3C[C@H](NC(=O)c4cccc5c(O)ccnc45)C3)n2-c2ccccc2F)nc1] |

-continued
| Example No. (where appropriate) | Structure |
|---|---|
| — | 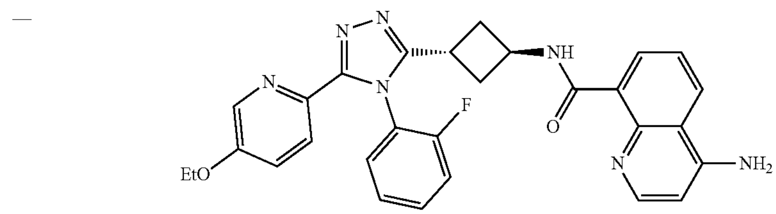 |
| 11 | 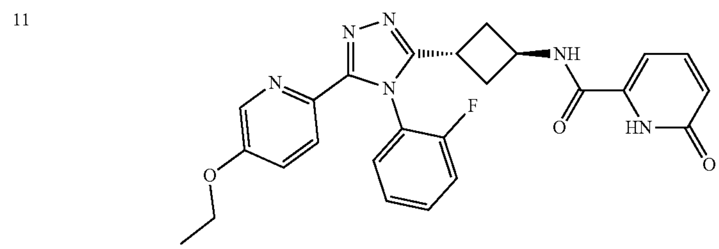 |
| 13 | 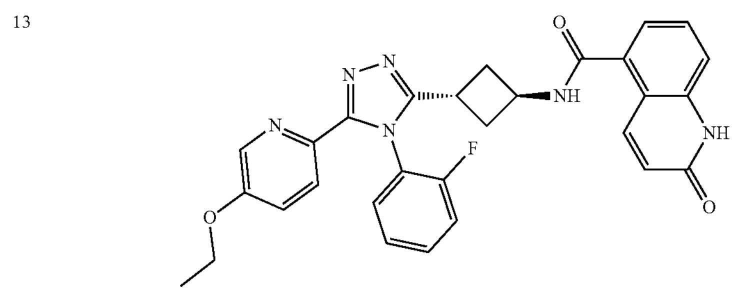 |
| 17 | 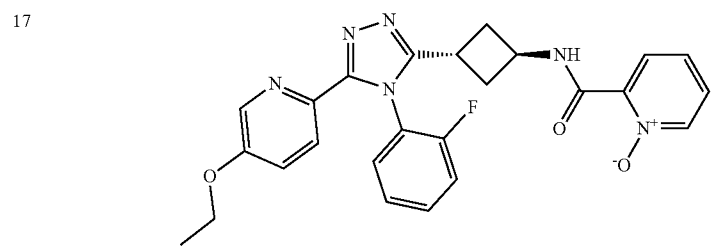 |
| 18 | 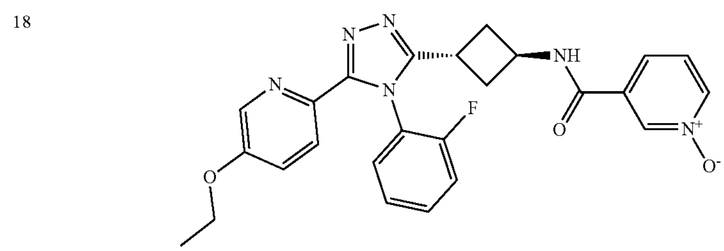 |
| 19 | 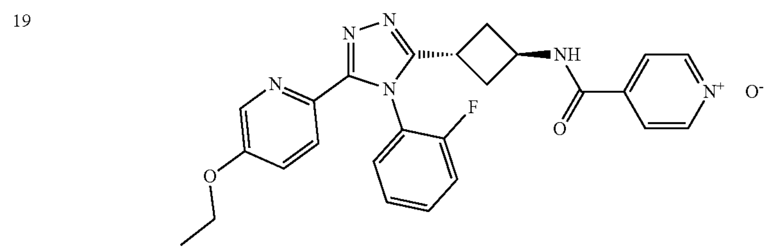 |

-continued
| Example No. (where appropriate) | Structure |
|---|---|
| 20 | 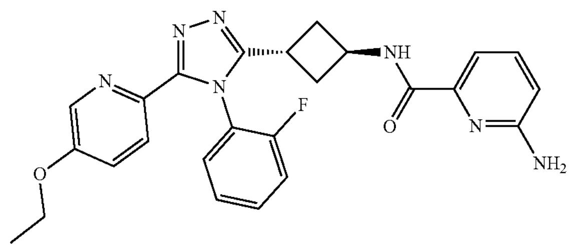 [SMILES: CCOc1ccc(-c2nnc([C@H]3C[C@H](NC(=O)c4cccc(N)n4)C3)n2-c2ccccc2F)nc1] |
| 21 | 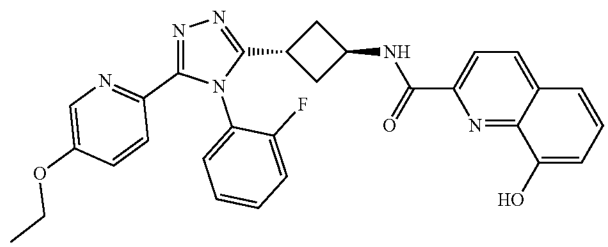 [SMILES: CCOc1ccc(-c2nnc([C@H]3C[C@H](NC(=O)c4ccc5cccc(O)c5n4)C3)n2-c2ccccc2F)nc1] |
| 22 | 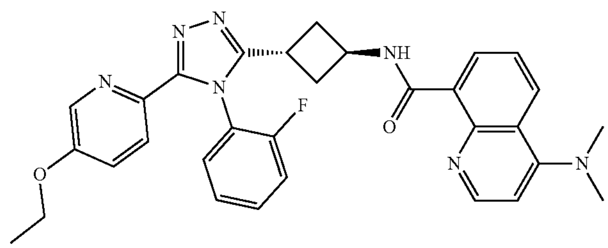 [SMILES: CCOc1ccc(-c2nnc([C@H]3C[C@H](NC(=O)c4cccc5c(N(C)C)ccnc45)C3)n2-c2ccccc2F)nc1] |
| 24 | 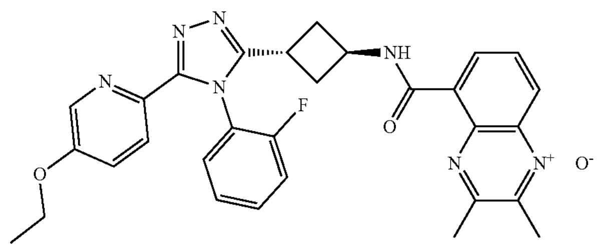 |
| 25 | 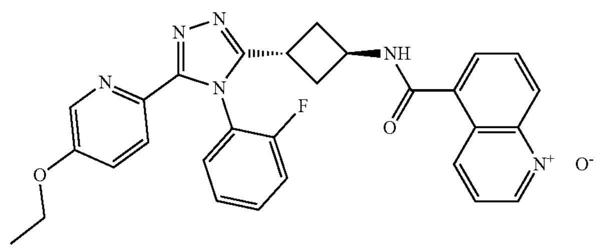 |
| 26 | 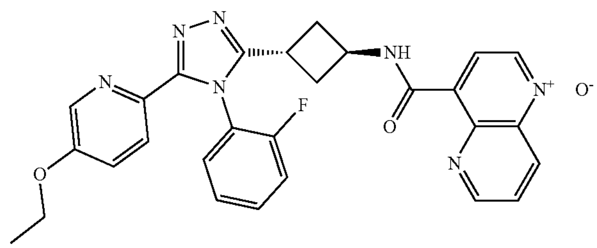 |

-continued

| Example No. (where appropriate) | Structure |
|---|---|
| 27 | 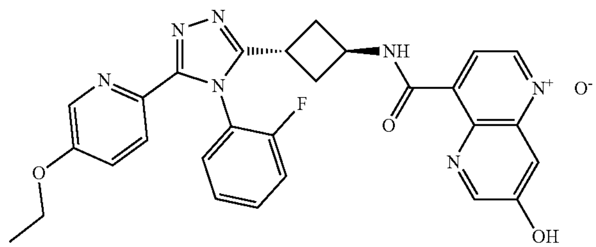 |
| 28 | 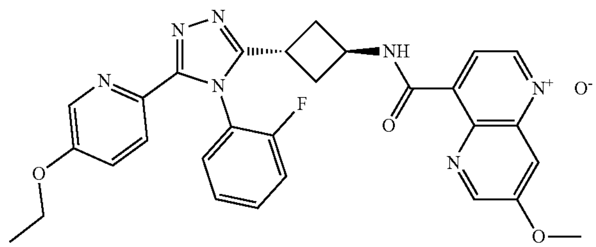 |
| 29 | 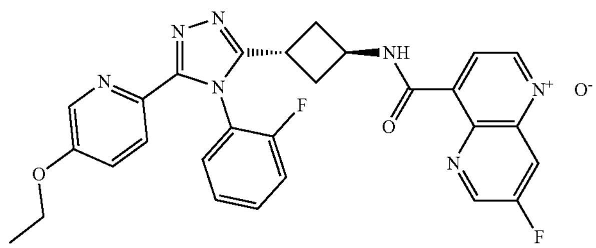 |

The compounds according to the invention may be prepared from readily available starting materials using synthetic methods known in the art. For example, these may be prepared using methods described in WO 2019/243822, the entire content of which is incorporated herein by reference.

The compounds may, for example, be obtained in accordance with the following method which forms part of the invention:

(a) reacting a compound of general formula (II):

(II)

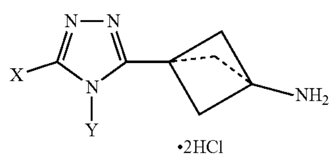

with a compound of general formula (III):

(III)

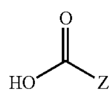

wherein in formulae (II) and (III), X, Y and Z are as herein defined;

(b) if desired, resolving a compound thus obtained into the stereoisomers thereof; and/or (c) if desired, converting a compound thus obtained into a salt thereof, particularly a pharmaceutically acceptable salt thereof; and/or (d) if desired, converting a compound thus obtained into an N-oxide thereof.

The method described above may be used to prepare any compound of formula (I) as herein described. The reaction of the compound of formula (II) with the compound of formula (III) is conveniently carried out in a solvent or mixture of solvents, such as for example a polar solvent such as acetonitrile, DMF, DCM, EtOAc, TBME, or THF or mixtures thereof. DMF is a preferred solvent. The reaction may suitably be carried out at room temperature, typically for a time from 1-5 hours (e.g. 1 hour, 2 hours or 3 hours).

In an embodiment, the compound of general formula (II) may be obtained by the following method:

(aa) reacting a compound of general formula (IV) with a compound of general formula (V) to form a compound of general formula (VI):

(IV)

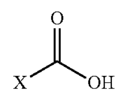

(V)

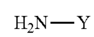

-continued (VI)

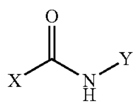

(bb) reacting the compound of general formula (VI) with a thionylating agent to form a compound of general formula (VII):

(VII)

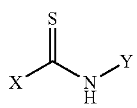

(cc) methylating the compound of general formula (VII) to form a compound of general formula (VIII):

(VIII)

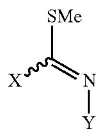

(dd) reacting the compound of general formula (VIII) with a compound of general formula (IX) to form a compound of general formula (X):

(IX)

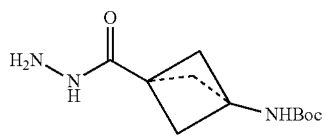

(X)

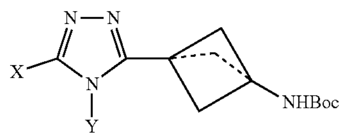

and (ee) deprotecting the Boc group of the compound of general formula (X) to form a compound of general formula (II):

(II)

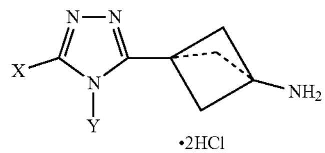

•2HCl wherein in formulae (IV) to (X), X and Y are as herein defined.

Step (aa) may suitably be performed under conventional amide formation conditions known to those skilled in the art. For example, the compounds of formulae (V) and (IV) may be reacted in the presence of HATU and DIPEA in DMF at room temperature for a period of 1 to 24 hours (e.g. 2 hours), or the compounds of formulae (V) and (IV) may be dissolved in DCM and pyridine, the reaction cooled in an ice bath and $POCl_3$ added dropwise and the resulting mixture stirred at room temperature for a period of 1 to 18 hours.

Step (bb) may be performed using a conventional thionylating agent known to those skilled in the art such as Lawesson's reagent (2,4-bis(4-methoxyphenyl)-1,3,2,4-dithiadiphosphetane-2,4-dithione) in a suitable solvent such as toluene. Suitably, about 0.5 to about 1 molar equivalent of the thionating agent may be employed. The thionation reaction may suitably be performed at a temperature of up to 100° C. (e.g. 80° C.) for a period of 2 to 24 hours (e.g. 16 hours).

Step (cc) may be performed using a conventional methylation reaction known to those skilled in the art. For example, the compound of general formula (VII) may suitably be reacted with at least one molar equivalent of methyl iodide in the presence of a base such as sodium hydroxide, sodium carbonate, potassium hydroxide or potassium carbonate.

Step (dd) may be performed using conventional triazole cyclisation conditions known to those skilled in the art. For example, compounds of formulae (VIII) and (IX) may be combined together in the presence of a suitable solvent (e.g. 1-butanol) and reacted under microwave irradiation or heated in an oil bath. This reaction may suitably be performed at a temperature of from 100 to 140° C. for a period of 1 to 24 hours (e.g. 5 to 20 hours).

Step (ee) may be performed using conventional Boc deprotection conditions known to those skilled in the art. For example, compounds of formula (X) may be dissolved in a suitable solvent (e.g. EtOH or IPA) and HCl (e.g. 5 N in IPA) added. HCl (e.g. 5 N in IPA) is typically added in 10-40 equiv, and additional portions can be added if necessary. The reaction can be performed at room temperature or elevated temperatures (e.g. 50-60° C.) for a period of 1 to 24 hours (e.g. 2 to 18 hours).

In an embodiment, the compounds of formula (I) may be obtained by the following method which forms part of the invention:

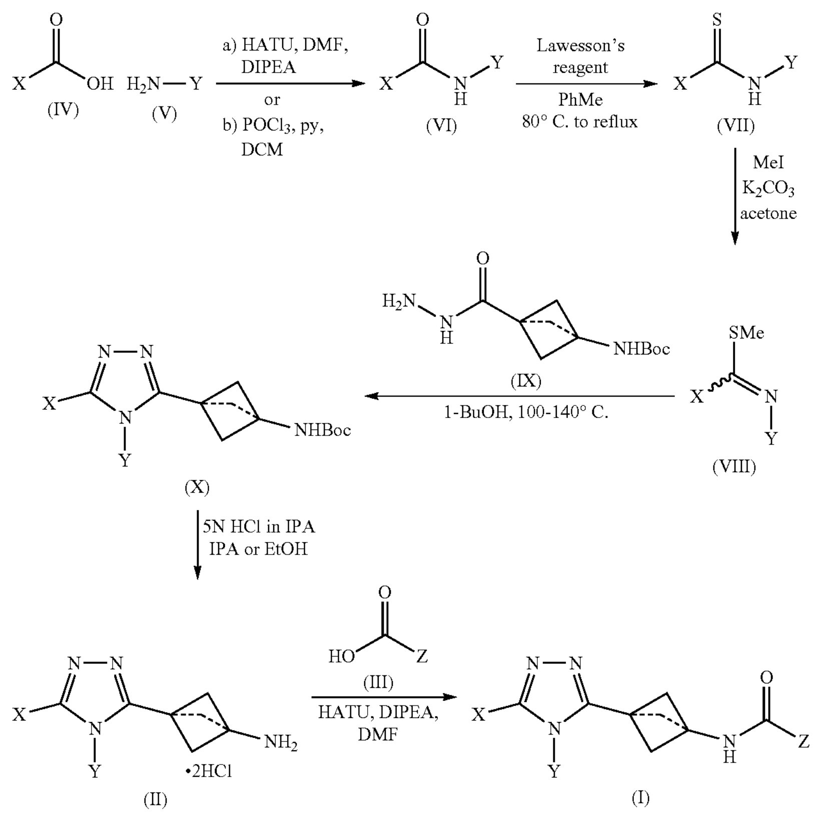

The compounds used as starting materials in the methods of preparation of compounds of formulae (I)-(X) are either known from the literature or may be commercially available. Alternatively, these may be obtained by methods known from the literature, for example methods disclosed in WO 2019/243822.

The compounds of general formulae (I) may be resolved into their enantiomers and/or diastereomers. For example, where these contain only one chiral centre or axis, these may be provided in the form of a racemate or may be provided as pure enantiomers, i.e. in the R- or S-form. Any of the compounds which occur as racemates may be separated into their enantiomers by methods known in the art, such as column separation on chiral phases or by recrystallisation from an optically active solvent. Those compounds with at least two asymmetric centres or axes may be resolved into their diastereomers on the basis of their physical-chemical differences using methods known per se, e.g. by chromatography and/or fractional crystallisation, and where these compounds are obtained in racemic form, they may subsequently be resolved into the enantiomers.

The invention further extends to tautomers of any of the compounds herein disclosed. As will be appreciated, certain compounds according to the invention may exist in tautomeric forms, i.e. in forms which readily interconvert by way of a chemical reaction which may involve the migration of a proton accompanied by a switch of a single bond and adjacent double bond. For example, the compounds may undergo amide-imidic acid tautomerism. Dependent on the conditions, the compounds may predominantly exist in the amide or imidic acid form and the invention is not intended to be limited to the particular form shown in any of the structural formulae given herein. Nitrogen-containing heterocycles having a hydroxyl substituent adjacent to the nitrogen atom may, for example, exist in the following tautomeric forms:

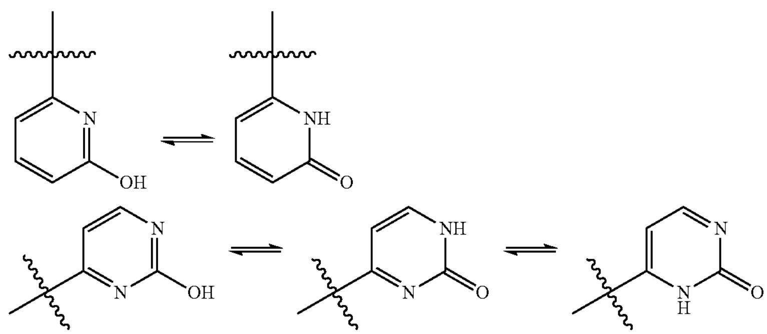

-continued

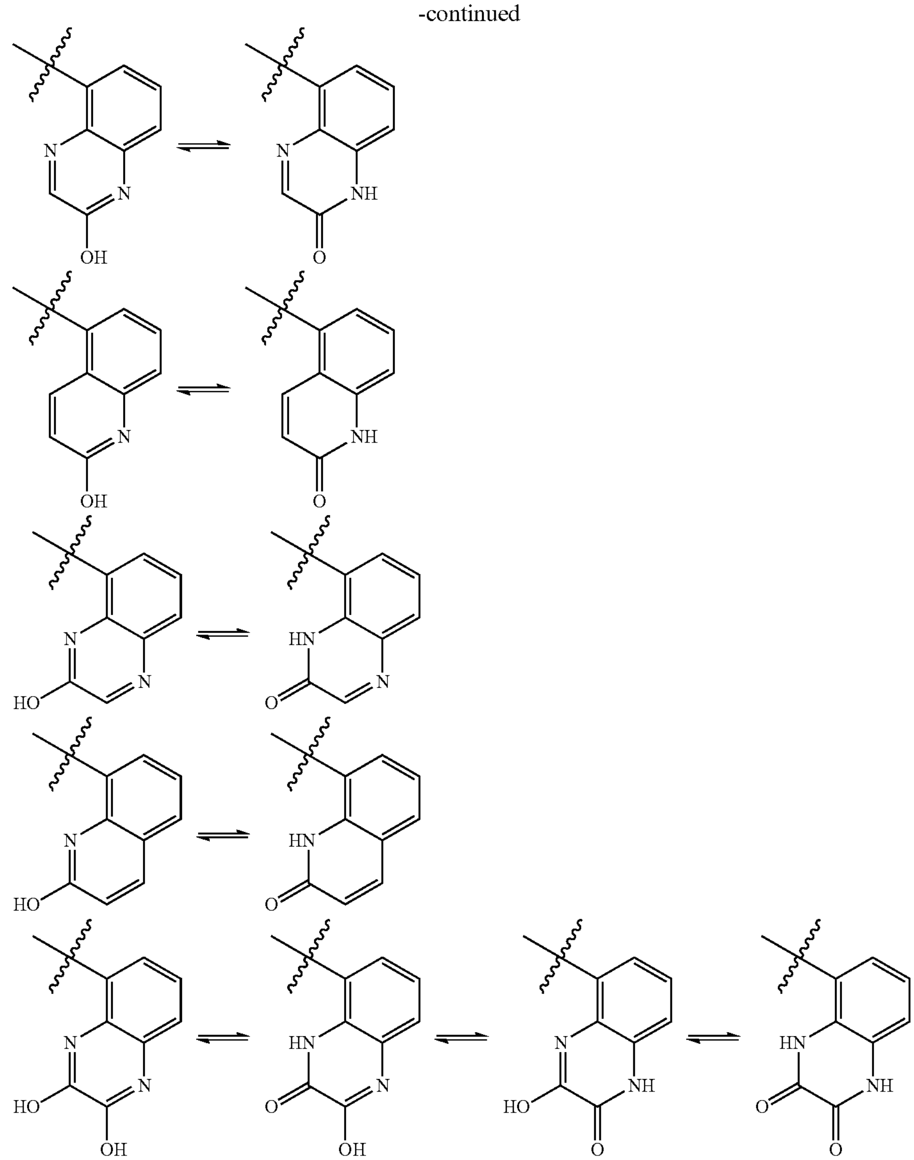

In these structures the particular point of attachment to the remainder of the molecule is merely illustrative and is not intended to be limiting. It will be understood that other points of attachment are equally possible.

The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

The compounds according to the invention may be provided in the form of an N-oxide. Such compounds can be prepared by oxidation of any compound of formula (I) which includes a tertiary nitrogen. Suitable oxidising agents may readily be selected by those skilled in the art. These include, for example, hydrogen peroxide (in the presence of the catalyst methyltrioxorhenium), peroxymonosulfuric acid, sodium percarbonate, or peracids such as mCPBA. In a further aspect the invention provides a method for the preparation of an N-oxide of a compound of formula (Ia), said method comprising the step of oxidising a compound of formula (I) as herein described.

In a further aspect there is provided pharmaceutical formulations comprising a compound of formula (I) as herein defined, or a tautomer, stereoisomer, N-oxide, pharmaceutically acceptable salt, or pro-drug thereof, together with one or more pharmaceutically acceptable carriers or excipients.

The compounds according to the invention and their pharmaceutically acceptable salts have valuable pharmacological properties, particularly an inhibitory effect on WNT/β-catenin and hippo signalling through inhibition of the adenosine binding site of the catalytic domain of tankyrase 1/2 and stabilization of the AXIN protein and AMOT proteins respectively. In view of their ability to inhibit signalling in the WNT and hippo signalling pathways, the compounds according to the invention and their pharmaceutically acceptable salts are suitable for the treatment and/or prevention of any condition or disease which may be affected by de-regulated signalling in the WNT and hippo signalling pathways, in particular those conditions or diseases which involve activation of β-catenin or altered YAP/TAZ signalling. The compounds of the invention and their pharmaceutically acceptable salts also have valuable pharmacological properties through affecting other target proteins of tankyrase 1/2.

The WNT and hippo signalling pathways play a central role in the pathology of a variety of cancers. The compounds of the invention are thus particularly suitable for preventing and/or retarding proliferation and metastasis of tumor cells, in particular carcinomas such as adenocarcinomas. More specifically, the compounds are effective in treatment and/or prevention of tumors emerging from colorectal tissue, uterus, pancreas, skin, liver, thyroid, prostate, ovary, stomach, lung, lymphoid, bladder, cervix, thyroid, head and neck, brain, breast and kidney, and in the treatment of melanoma. Particularly preferably, the compounds herein described may be used in the treatment and/or prevention of colorectal cancer, non-small cell lung cancer and melanoma.

As used herein, the term "proliferation" refers to cells undergoing mitosis. The term "retarding proliferation" indicates that the compounds inhibit proliferation of a cancer cell. In preferred embodiments, "retarding proliferation" indicates that DNA replication is at least 10% less than that observed in untreated cells, more preferably at least 25% less, yet more preferably at least 50% less, e.g. 75%, 90% or 95% less than that observed in untreated cancer cells.

The term "carcinoma" refers to any malignant growth which arises from epithelial cells. Exemplary carcinomas include basal cell carcinoma, squamous cell carcinoma and adenocarcinoma. Adenocarcinomas are malignant tumors originating in the glandular epithelium and include colorectal, pancreatic, breast and prostate cancers.

The compounds of the invention also find use in cancer immunotherapy. They may, for example, be used in a combination therapy together with known immune checkpoint inhibitors, such as PD-1 and PD-L1.

As used herein, the term "immunotherapy" refers to the beneficial therapeutic enhancement of the interplay between the immune system and a tumor, infection, or other diseases. In particular, immunotherapy is a type of therapy that uses substances to stimulate or suppress the immune system to help the body fight cancer, infection, and other diseases. Some types of immunotherapy only target certain cells of the immune system. Others affect the immune system in a general way.

The compounds according to the invention and their pharmaceutically acceptable salts have valuable pharmacological properties that may also be used for treatment or prevention of non-cancer indications that are influenced by the activity of tankyrase 1/2, dependent or independent of its impact on WNT and/or hippo signalling. These include non-regenerative wound healing, viral infections such as influenza and Herpes Simplex Virus (HSV) infections, fibrosis such as pulmonary, dermal-, renal- and liver fibrosis, myocardial fibrosis, osteoarthritis, and metabolic conditions such as aberrant systemic glucose metabolism and type 2 diabetes.

Viewed from a further aspect the invention thus provides a compound of formula (I) as herein defined, or a tautomer, stereoisomer, N-oxide, pharmaceutically acceptable salt, or pro-drug thereof, for use in therapy. Unless otherwise specified, the term "therapy" as used herein is intended to include both treatment and prevention.

In a still further aspect the invention provides a compound of formula (I) as herein defined, or a tautomer, stereoisomer, N-oxide, pharmaceutically acceptable salt, or pro-drug thereof, for use in the treatment or prevention of a tumor emerging from the gastrointestinal tract (e.g. the stomach or colorectal tissue), uterus, pancreas, bone, soft tissue, skin, liver, thyroid, prostate, ovary, testis, lung, lymphoid, bladder, cervix, endocrine organs, thyroid, head and neck, CNS, brain, breast or kidney, in the treatment of melanoma or triple-negative breast cancer, in the treatment of non-regenerative wound healing, or in the treatment or prevention of a viral infection (e.g. influenza or Herpes Simplex Virus infection), fibrosis (e.g. pulmonary-, dermal-, renal- or liver fibrosis, or myocardial fibrosis), osteoarthritis or a metabolic condition (e.g. aberrant systemic glucose metabolism or type 2 diabetes).

In another aspect the invention provides the use of a compound of formula (I) as herein defined, or a tautomer, a stereoisomer, an N-oxide, a pharmaceutically acceptable salt, or pro-drug thereof in the manufacture of a medicament for the treatment or prevention of any disease or disorder as herein described.

In a yet further aspect the invention provides a method of treatment or prevention of any disease or disorder as herein described, said method comprising the step of administering a compound of formula (I) as herein defined, or a tautomer, a stereoisomer, an N-oxide, a pharmaceutically acceptable salt, or pro-drug thereof.

Small molecules that selectively target the developmental pathways which control pattern formation during embryogenesis, including the WNT and hippo signalling pathways, are considered to be valuable for directing differentiation of pluripotent stem cells toward many desired tissue types (see Wang et al., ACS Chemical Biology, 16 Nov. 2010). As modulators of WNT signalling, the compounds herein described also have effects on the development of cellular differentiation. The compounds described herein therefore have valuable properties for use in regenerative medicine, for example in protocols for lineage specific in vitro differentiation of progenitor cells. By "progenitor cell" is meant a cell with the capacity to differentiate into another cell type, e.g. a stem cell.

According to this aspect, the present invention provides a method (e.g. an in vitro method) of promoting and/or directing cellular differentiation comprising contacting a progenitor cell with an effective amount of a compound of formula (I) as herein defined, or a tautomer, stereoisomer, N-oxide, pharmaceutically acceptable salt, or pro-drug thereof. In particular, the progenitor cell is contacted with said at least one compound under suitable conditions and for a sufficient time for the progenitor cell to differentiate into a new cell type. In a related aspect, the present invention provides the use of at least one compound as herein defined for promoting and/or directing cellular differentiation of a progenitor cell, especially in vitro.

Preferably, the progenitor cell is a totipotent or a pluripotent cell, especially a stem cell such as an embryonic stem cell. Preferred are mammalian progenitor cells such as mouse, rat and human cells, especially human cells. Such stem cells may be obtained from established cell cultures or may be derived directly from mammalian tissue by methods known in the art, including non tissue-destructive methods.

In a preferred embodiment, the progenitor cell is promoted and/or directed to differentiate into a new cell type which is a myocyte (e.g. a cardiomyocyte), a neuronal cell (e.g. a dopaminergic neuronal cell), an endocrine pancreatic cell or a hepatocyte or a cell type which may further differentiate into a myocyte, a neuronal cell, an endocrine pancreatic cell or a hepatocyte. Especially preferably, the progenitor cell is an embryonic stem cell and the new cell type is a cardiomyocyte, a dopaminergic neuronal cell, an endocrine pancreatic cell, a hepatocyte, or a cardiomyocyte.

The dosage required to achieve the desired activity of the compounds herein described will depend on the compound which is to be administered, the patient, the nature and severity of the condition, the method and frequency of administration and may be varied or adjusted according to choice. Typically, the dosage may be expected to be in the range from 1 to 100 mg, preferably 1 to 30 mg (when administered intravenously) and from 1 to 1000 mg, preferably from 1 to 200 mg (when administered orally).

The compounds of the invention may be formulated with one or more conventional carriers and/or excipients according to techniques well known in the art. Typically, the compositions will be adapted for oral or parenteral administration, for example by intradermal, subcutaneous, intraperitoneal or intravenous injection. Suitable pharmaceutical forms thus include plain or coated tablets, capsules, suspensions and solutions containing the active component optionally together with one or more conventional inert carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propylene glycol, stearylalcohol, carboxymethylcellulose or fatty substances such as hard fat or suitable mixtures of any of the above.

Alternatively, the compounds of the invention may be administered topically at or near the affected site. Topical compositions include gels, creams, ointments, sprays, lotions, salves, sticks, powders, pessaries, suppositories, aerosols, drops, solutions and any of the other conventional pharmaceutical forms in the art. Topical administration to inaccessible sites may be achieved by techniques known in the art, e.g. by use of catheters or other appropriate drug delivery systems.

The compounds may suitably be formulated in a form for parenteral administration, e.g. for intravenous injection. For this purpose, sterile solutions containing the active compounds may be employed.

The pharmacological properties of the compounds of the invention can be analysed using standard assays for functional activity. Detailed protocols for testing of the compounds of the invention are provided in the Examples.

The invention will now be described in more detail in the following non-limiting Examples:

EXAMPLES

Examples 1-5

General Procedure A: Amide Coupling

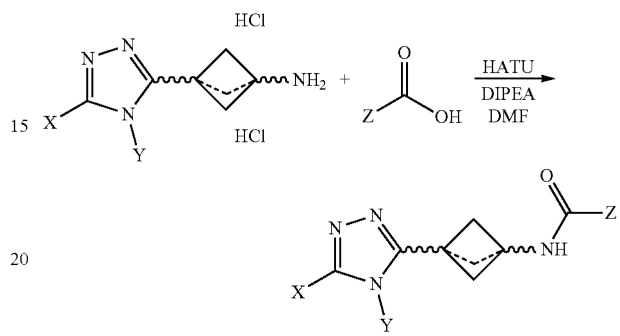

The appropriate acid (1.1 equiv.) and HATU (1.2 equiv) were dissolved in anhydrous DMF (0.10 M) and DIPEA (4.0 equiv) was added. After 30 minutes, the amine (1 equiv.) was added. The crude reaction mixture was purified on a Phenomenex Luna C18 reversed phase column eluted with water/acetonitrile 30-70% containing 0.1% formic acid. Product fractions were lyophilised.

Examples 7-29

General Procedure A: Amide Coupling

The appropriate acid (1.1 equiv.) and HATU (1.2 equiv.) were dissolved in anhydrous DMF (0.10 M) and DIPEA (4.0 equiv.) was added. After 30 minutes, amine 7 (1.0 equiv.) was added. The crude reaction mixture purified on a ReproSil-Pur C18/XSelect C18 reversed phase column eluted with water/acetonitrile 30-70% containing 0.1% formic acid/10 mM aqueous ammonium bicarbonate. Product fractions were lyophilized.

General Procedure A-1: Amide Coupling

The appropriate acid (1.1 equiv.) and HATU (1.2 equiv.) were dissolved in anhydrous DMF (0.10 M) and DIPEA (4.0 equiv.) was added. After 30 minutes, amine 7 (1.0 equiv.) was added. After 1 h, ammonia (32%) in water was added. The crude reaction mixture purified on an XSelect C18 reversed phase column eluted with water/acetonitrile 30-70% containing 10 mM aqueous ammonium bicarbonate. Product fractions were lyophilized.

Procedure B: Methyl 6-(chlorocarbonyl)picolinate (17)

Pyridine-2,6-dicarboxylic acid monomethyl ester (1.0 equiv.) was added to thionyl chloride (31.2 equiv.). After 1 h stirring at 75° C., the mixture was reduced in vacuo.

General Procedure B-1: Carboxylic Acid Synthesis

The appropriate ester (1.0 equiv.) and lithium hydroxide monohydrate (5 equiv.) were added to THE and $H_2O$. After overnight, the mixture was acidified by addition of HCl (pH 5-7), filtered and dried in vacuo.

General Procedure C: Methyl Ester Synthesis $H_2SO_4$ (conc. 2.5 equiv.) was added to the appropriate acid (1.0 equiv.) in MeOH (0.2-0.3M). After stirring at 70°

C. until completion, the reaction mixture was cooled to room temperature, concentrated, worked-up using ethyl acetate/water, washed with brine, dried over sodium sulfate and evaporated in vacuo.

General Procedure D: N-Oxide Synthesis

At 0° C., MTO (0.1 equiv.) and hydrogen peroxide (5 equiv.) were added to the appropriate ester in DCM (0.2-0.3M). After overnight under argon, the mixture was reduced in vacuo and purified on a silica column eluted with DCM/MeOH 0-10%. Product fractions were reduced in vacuo.

Example 1—Preparation of N-((1R,3r)-3-(5-(5-ethoxypyridin-2-yl)-4-(2-fluorophenyl)-4H-1,2,4-triazol-3-yl)cyclobutyl)-3-hydroxyquinoxaline-5-carboxamide Step 1: Preparation of Methyl 3-hydroxyquinoxaline-5-carboxylate (3) and methyl 2-hydroxyquinoxaline-5-carboxylate (4)

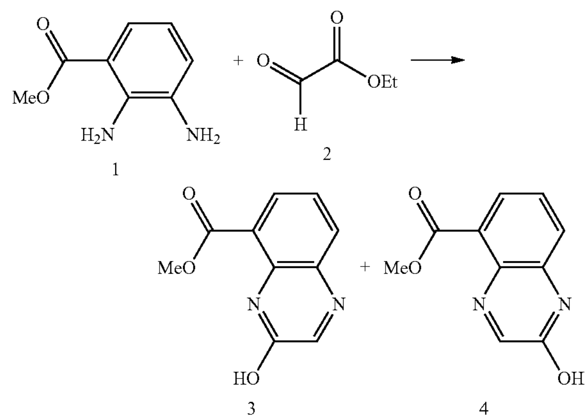

1

2

3

4

An 8 mL vial was charged with a brown solution of methyl 2,3-diaminobenzoate (50 mg, 0.301 mmol) in methanol (2 ml). The mixtures were cooled to 0° C. before addition of ethyl 2-oxoacetate (0.060 ml, 0.301 mmol) and was allowed to warm to room temperature over 4 hours. After 16 hours the solvent was removed in vacuo yielding a black solid. The crude products were isolated on a 12 g silica column, eluted with dichloromethane/MeOH 0-3%. Product fractions were evaporated in vacuo giving 3 (first eluting), 39 mg (0.191 mmol), 63.5% yield, 100% pure and 4 (second eluting), 13 mg (0.064 mmol), 21.3% yield, 100.0% pure. Product identity assigned by NMR.

Step 2: Preparation of 3-hydroxyquinoxaline-5-carboxylic Acid (5)

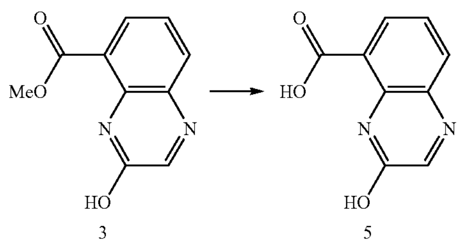 [SMILES: COC(=O)c1cccc2ncc(O)nc12 ; O=C(O)c1cccc2ncc(O)nc12]

3

5

To a solution of 3 (42.5 mg, 0.208 mmol) in water (1 ml) and tetrahydrofuran (2 ml) was added $LiOH \cdot H_2O$ (75.2 mg, 1.792 mmol). The mixture was stirred at room temperature for 66 hours. Then the reaction mixture was concentrated in vacuo and acidified by addition of HCl (aq. 1M, 4 ml). An off-white precipitate formed which was filtrated off. The residue was co-evaporated with toluene (25 ml) and dichloromethane (25 mL) and dried yielding 5, 39.6 mg (0.230 mmol), 100% pure, 100% yield as an off-white solid.

Step 3: Preparation of N-((1R,3r)-3-(5-(5-ethoxypyridin-2-yl)-4-(2-fluorophenyl)-4H-1,2,4-triazol-3-yl)cyclobutyl)-3-hydroxyquinoxaline-5-carboxamide

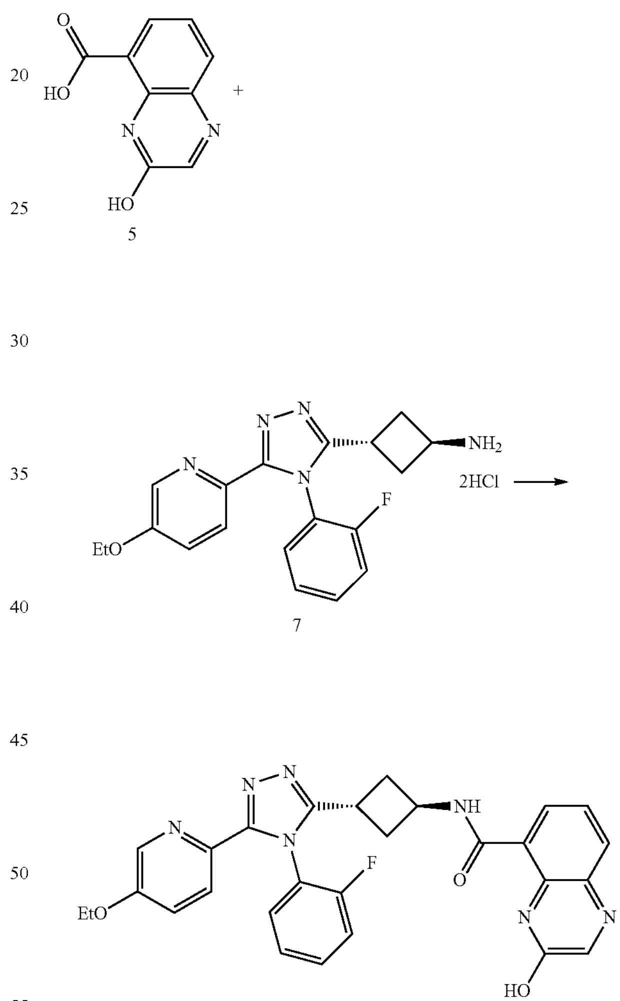

5

7

Prepared according to General Procedure A giving the title compound, 55.4 mg (0.105 mmol), 99.9% pure, 45.8% yield as an off-white solid.

$^1H$ NMR (400 MHz, DMSO) δ 12.52 (s, 1H), 9.24 (s, 1H), 8.25 (s, 1H), 8.13 (dd, J=7.9, 1.4 Hz, 1H), 8.05 (d, J=8.8 Hz, 1H), 7.98 (d, J=8.0 Hz, 1H), 7.93 (d, J=3.0 Hz, 1H), 7.61-7.47 (m, 3H), 7.46-7.36 (m, 2H), 7.33 (td, J=7.7, 1.3 Hz, 1H), 4.69 (p, J=7.2 Hz, 1H), 4.10 (q, J=7.0 Hz, 2H), 3.41-3.34 (m, 1H), 2.87-2.76 (m, 1H), 2.68-2.59 (m, 1H), 2.39 (dd, J=18.4, 9.2 Hz, 2H), 1.31 (t, J=6.9 Hz, 3H).

Example 2—Preparation of (1R,3r)-3-(5-(5-ethoxy-pyridin-2-yl)-4-(2-fluorophenyl)-4H-1,2,4-triazol-3-yl)cyclobutan-1-amine Dihydrochloride Step 1: Preparation of Methyl 2-hydroxyquinoxaline-5-carboxylate (4)

Prepared according to Step 1 of Example 1.

Step 2: Preparation of Methyl 2-hydroxyquinoxaline-5-carboxylate (6)

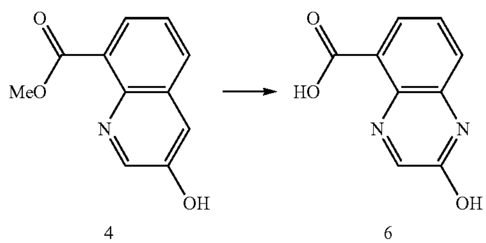 [SMILES: COC(=O)c1cccc2cc(O)cnc12 ; O=C(O)c1cccc2nc(O)cnc12]

4 6

To a solution of 4 (65.3 mg, 0.320 mmol) in water (1 ml) and tetrahydrofuran (2 ml) was added $LiOH \cdot H_2O$ (97.1 mg, 2.314 mmol). The mixture was stirred at room temperature for 66 hours. Then the reaction mixture was concentrated in vacuo and acidified by addition of HCl (aq. 1M, 4 mL). An off-white precipitate formed which was filtrated off. The residue was co-evaporated with toluene (25 ml) and dichloromethane (25 mL) and dried yielding 5, 42.2 mg (0.221 mmol), 99.5% pure, 69.0% yield as an off-white solid.

Step 3: Preparation of (1R,3r)-3-(5-(5-ethoxypyridin-2-yl)-4-(2-fluorophenyl)-4H-1,2,4-triazol-3-yl) cyclobutan-1-amine Dihydrochloride

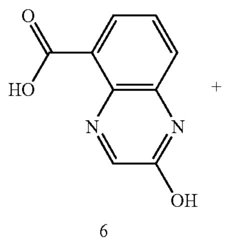

6

+

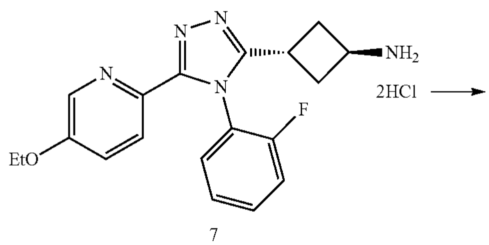

7

-continued

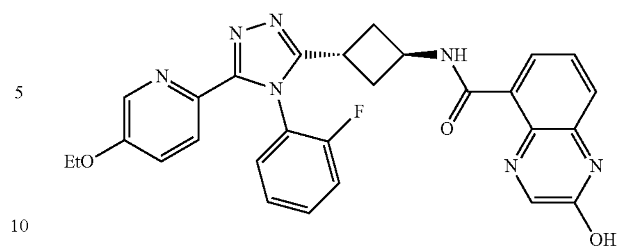

Prepared according to General Procedure A giving the title compound, 53.3 mg (0.101 mmol), 99.4% pure, 45.4% yield as an off-white solid.

$^1$H NMR (400 MHz, DMSO) δ 12.59 (s, 1H), 9.36 (d, J=7.2 Hz, 1H), 8.23 (s, 1H), 8.05 (d, J=8.7 Hz, 1H), 7.93 (d, J=2.8 Hz, 1H), 7.64-7.46 (m, 5H), 7.46-7.36 (m, 2H), 7.32 (td, J=7.7, 1.4 Hz, 1H), 4.66 (h, J=7.4 Hz, 1H), 4.10 (q, J=6.9 Hz, 2H), 3.29 (dd, J=9.6, 4.7 Hz, 1H), 2.80 (ddt, J=11.8, 8.0, 3.9 Hz, 1H), 2.61 (ddt, J=11.9, 8.0, 4.1 Hz, 1H), 2.31 (dq, J=24.9, 9.9 Hz, 2H), 1.31 (t, J=7.0 Hz, 3H).

Example 3—Preparation of N-((1R,3r)-3-(5-(5-ethoxypyridin-2-yl)-4-(2-fluorophenyl)-4H-1,2,4-triazol-3-yl)cyclobutyl)-2,3-dihydroxyquinoxaline-5-carboxamide Step 1: Preparation of Methyl 2,3-dihydroxyquinoxaline-5-carboxylate (9)

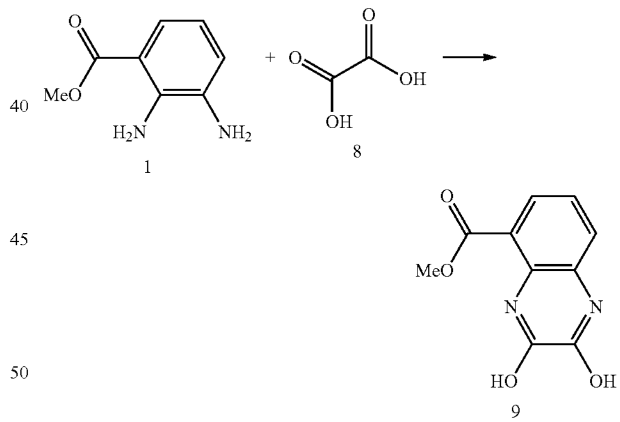

1 8 9

A 20 ml tube was charged with 1 (0.499 g, 3.0 mmol), oxalic acid (8, 0.297 g, 3.30 mmol) and silica 60 Å, 60-200 micron (1.496 g, 24.90 mmol) under a nitrogen atmosphere and toluene (anhydrous) (9.0 ml) was added. The brown mixture was refluxed for 4 hours. Then the mixture was cooled to room temperature and filtered through a plug of cotton and rinsed with toluene (discarded) and extracted with 50 ml of acetonitrile and with 50 mL of methanol giving the crude product. The solvents were evaporated in vacuo and purified on a 12 g silica column eluted with dichloromethane/methanol 0-10%. Product fractions were evaporated in vacuo giving 9, 158 mg, 0.696 mmol, 97.6% pure, 23.2% yield as a light brown solid.

Step 2: Preparation of 2,3-dihydroxyquinoxaline-5-carboxylate (10)

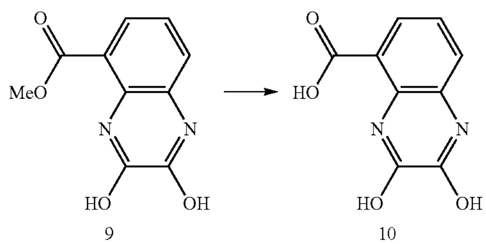 [SMILES: COC(=O)c1cccc2nc(O)c(O)nc12 ; O=C(O)c1cccc2nc(O)c(O)nc12]

To 9 (60.6 mg, 0.275 mmol) in a mixture of tetrahydrofuran (2.5 mL) and water (2.5 mL) was added $LiOH{\cdot}H_2O$ (57.4 mg, 1.368 mmol). The mixture was stirred at room temperature for 17 hours. Then the solvent was removed in vacuo yielding a black oil which was diluted with 2 mL of water and acidified with 4 mL 1M HCl giving a dark precipitate. This was filtered off and rinsed with 2 mL 1M HCl, with water and dried giving 10, 40.0 mg (0.166 mmol), 85.7% pure, 60.4% yield.

Step 3: Preparation of N-((1R,3r)-3-(5-(5-ethoxypyridin-2-yl)-4-(2-fluorophenyl)-4H-1,2,4-triazol-3-yl)cyclobutyl)-2,3-dihydroxyquinoxaline-5-carboxamide

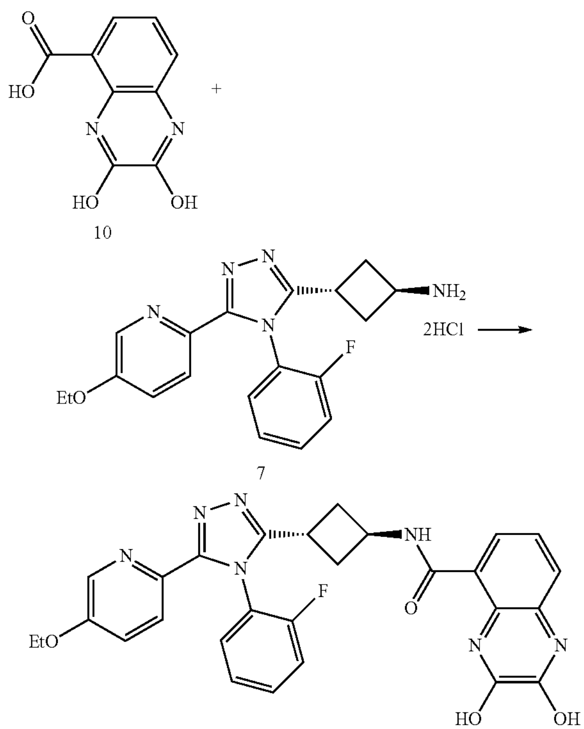

Prepared according to General Procedure A but instead of HATU, PyBOP (1.1 eq.) was used giving the title compound, 13.8 mg (0.025 mmol), 99.1% pure, 20.8% yield as a white solid.

$^1H$ NMR (400 MHz, DMSO) δ 12.20 (s, 1H), 12.08 (s, 1H), 9.13 (s, 1H), 8.05 (d, J=8.7 Hz, 1H), 7.93 (d, J=2.9 Hz, 1H), 7.66 (dd, J=8.1, 1.3 Hz, 1H), 7.61-7.47 (m, 3H), 7.42 (ddd, J=9.9, 8.3, 1.3 Hz, 1H), 7.38-7.24 (m, 2H), 7.19 (s, 1H), 4.66 (q, J=7.3 Hz, 1H), 4.10 (q, J=7.0 Hz, 2H), 2.79 (dt, J=7.9, 4.0 Hz, 1H), 2.70-2.57 (m, 1H), 2.39 (dt, J=19.9, 9.6 Hz, 2H), 1.31 (t, J=6.9 Hz, 3H).

Example 4—Preparation of 5-(((1R,3r)-3-(5-(5-ethoxypyridin-2-yl)-4-(2-fluorophenyl)-4H-1,2,4-triazol-3-yl)cyclobutyl)carbamoyl)quinoxaline 1-oxide Step 1: Preparation of 5-(methoxycarbonyl)quinoxaline 1-oxide (12)

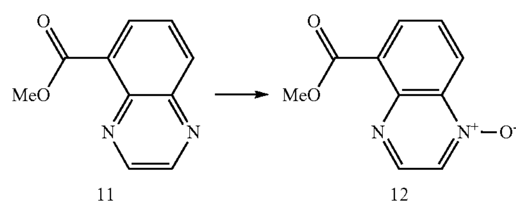 [SMILES: COC(=O)c1cccc2nccnc12 ; COC(=O)c1cccc2c1ncc[n+]2[O-]]

Methyl quinoxaline-5-carboxylate 11 (100 mg, 0.531 mmol) was dissolved in 3 mL of dichloromethane in a brown 8 mL glass vial and flushed with argon. Then hydrogen peroxide (0.271 ml, 2.66 mmol) and methyltrioxorhenium (13.24 mg, 0.053 mmol) were added. The mixture was stirred at room temperature for 24 hours. Then the crude reaction mixture was filtered and the solvent was removed in vacuo yielding a yellow oil. The crude product was purified on a 12 g silica column eluted with dichloromethane/MeOH 0-1%. Product fractions were evaporated in vacuo yielding 5-(methoxycarbonyl)quinoxaline 1-oxide 12, 16.1 mg (0.075 mmol), 95.2% pure, 14.1% yield as an off-white solid.

Step 2: Preparation of 5-carboxyquinoxaline 1-oxide (13)

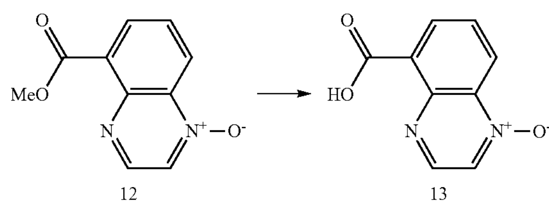 [SMILES: COC(=O)c1cccc2c1ncc[n+]2[O-] ; O=C(O)c1cccc2c1ncc[n+]2[O-]]

5-(methoxycarbonyl)quinoxaline 1-oxide 12 (40.6 mg, 0.199 mmol) was dissolved in 1 mL of tetrahydrofuran and water (0.333 ml) and LiOH·H2O (41.7 mg, 0.994 mmol) was added. The mixture was stirred at room temperature for 18 hours. Then the reaction mixture was concentrated in vacuo and acidified with 2 mL 1M HCl. The white precipitate was filtered off and dried yielding 5-carboxyquinoxaline 1-oxide 13, 37.7 mg (0.189 mmol), 95.5% pure, 95.0% yield) as an off-white solid.

Step 3: Preparation of 5-(((1R,3r)-3-(5-(5-ethoxypyridin-2-yl)-4-(2-fluorophenyl)-4H-1,2,4-triazol-3-yl)cyclobutyl)carbamoyl)quinoxaline 1-oxide

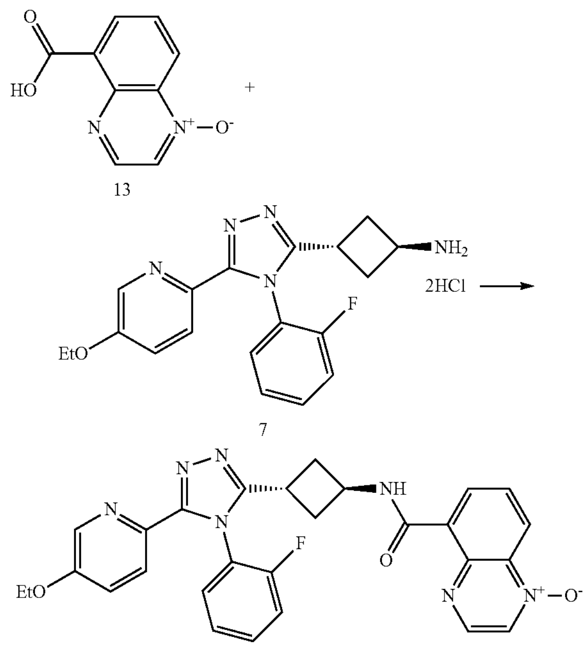

13

7

Prepared according to General Procedure A giving the title compound, 60.7 mg (0.110 mmol), 95.0% pure, 55.4% yield as a pale brown solid.

$^1$H NMR (400 MHz, CDCl3) δ 10.60 (d, J=5.9 Hz, 1H), 8.89 (dd, J=7.4, 1.6 Hz, 1H), 8.73 (dd, J=8.7, 1.6 Hz, 1H), 8.67 (d, J=3.7 Hz, 1H), 8.41 (d, J=3.6 Hz, 1H), 8.16 (d, J=8.7 Hz, 1H), 7.91-7.80 (m, 2H), 7.44 (ddt, J=9.3, 8.3, 3.7 Hz, 1H), 7.25-7.14 (m, 4H), 4.88-4.76 (m, 1H), 4.04 (q, J=7.0 Hz, 2H), 3.51 (tt, J=10.3, 5.7 Hz, 1H), 3.07 (dtt, J=11.3, 5.5, 2.6 Hz, 2H), 2.52 (dddd, J=16.2, 13.2, 9.8, 6.5 Hz, 2H), 1.40 (t, J=7.0 Hz, 3H).

Example 5—Preparation of 5-ethoxy-2-(4-(2-fluorophenyl)-5-((1r,3R)-3-(quinoxaline-5-carboxamido)cyclobutyl)-4H-1,2,4-triazol-3-yl)pyridine 1-oxide

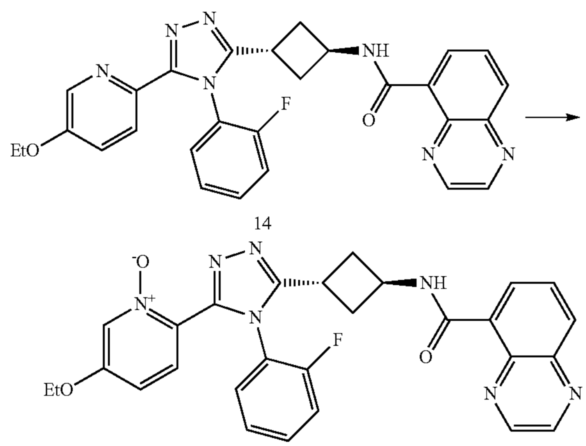

14

Compound 14 (52.2 mg, 0.102 mmol) was prepared according to Example 154 of WO 2019/243822, dissolved in 2 mL of dichloromethane and flushed with argon and hydrogen peroxide (9.42 µl, 0.092 mmol) and methyltrioxorhenium (4.9 mg, 0.020 mmol) were added. The mixture was stirred at room temperature for 24 hours. Then the crude reaction mixture was concentrated in vacuo, re-dissolved in MeOH (~1 mL), filtered and purified on a Phenomenex Luna C18 reversed phase column eluted with water/acetonitrile 30-70% containing 0.1% formic acid. Product fractions were lyophilized in vacuo yielding the title compound, 24.05 mg (0.046 mmol), 99.8% pure, 44.6% yield as an off-white solid.

$^1$H NMR (400 MHz, CDCl3) δ 10.70 (d, J=5.8 Hz, 1H), 8.97 (d, J=1.8 Hz, 1H), 8.86 (dd, J=8.3, 1.7 Hz, 2H), 8.26 (dd, J=8.4, 1.6 Hz, 1H), 7.94-7.87 (m, 1H), 7.73 (d, J=2.2 Hz, 1H), 7.65 (d, J=8.9 Hz, 1H), 7.43-7.32 (m, 2H), 7.21-7.10 (m, 2H), 6.89 (dd, J=8.9, 2.3 Hz, 1H), 4.88-4.77 (m, 1H), 4.01 (q, J=6.9 Hz, 2H), 3.61 (tt, J=10.0, 5.5 Hz, 1H), 3.06 (ddt, J=21.0, 12.6, 5.7 Hz, 2H), 2.62-2.50 (m, 2H), 1.41 (t, J=7.0 Hz, 3H).

Example 6—ADME Properties

Methods:

Cellular $IC_{50}$ and biochemical $IC_{50}$ values for the compounds of Examples 1 to 5 were determined in accordance with the following protocol (see also Anumala et al., Discovery of Novel Series of Tankyrase Inhibitors by a Hybridization Approach J. Med. Chem. 2017). The compound of Example 154 of WO 2019/243822 was used as a comparison. This has the following structure:

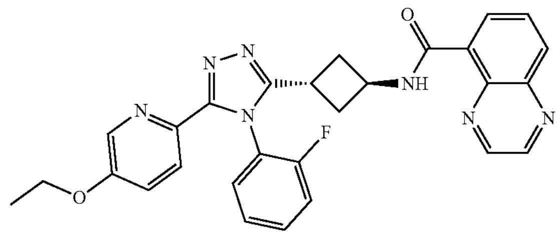 [SMILES: CCOc1ccc(-c2nnc([C@H]3C[C@H](NC(=O)c4cccc5nccnc45)C3)n2-c2ccccc2F)nc1]

$IC_{50}$ Calculations:

XLfit (idbs) was used to determine the IC50-values in inhibition experiments. The following formula was chosen to fit the data points (Langmuir Binding Isotherm): fit=((A+(B*x))+(((C−B)*(1−exp((−1*D)*x)))/D)), res=(y−fit).

Metabolic stability was investigated in mouse liver microsomes (MLM) and in human liver microsomes (HLM): Each compound was dissolved in DMSO to a concentration of 10 mM and further diluted to 100 µM using acetonitrile. Liver microsomes from selected species were incubated in duplicate with each compound at a final concentration of 1 µM in 0.1 M potassium phosphate buffer (pH 7.4) containing 3.3 mM MgCl2, 0.5 mg/ml microsomal protein, in the presence or absence of NADPH (1 mM). Incubations were performed at 37° C. Control incubations with reference substances were included for each experiment. At different time points (t=0, 5, 15, 30, 45 min), an appropriate aliquot of the incubation mixture was transferred into a quench plate containing acetonitrile and internal standard cooled to 4° C. After the last time point, the quench plates were mixed thoroughly and centrifuged for 15 minutes at 3700 rpm and 10° C. (Eppendorf 5804R). The supernatant was transferred to new 96 well plates and subjected to LCMS analysis. The disappearance of the parent compound was determined.

Results and Discussion:

Cellular $IC_{50}$ and biochemical $IC_{50}$ values are provided in table 1 together with calculated Log P. Metabolic stability data is presented in table 2.

TABLE 1

| Compound Example No. | Biochemical $IC_{50}$ TNKS2 (nM) | Cellular $IC_{50}$ HEK293 (nM) | cLogP[a] |
|---|---|---|---|
| 1 | 36 | 220 | 2.55 |
| 2 | 1.5 | 1.1 | 2.55 |
| 3 | 71 | 1248 | 1.75 |
| 4 | 1.6 | 2.5 | 2.80 |
| 5 | 1.3 | 0.75 | 2.97 |
| Example 154 of WO 2019/243822 | 1.8 | 0.53 | 3.44 |

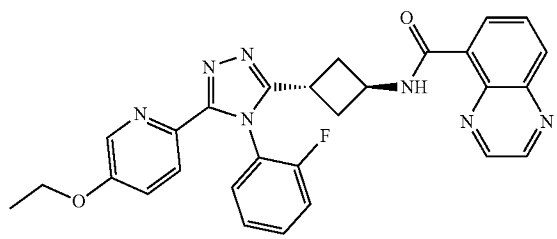 [SMILES: CCOc1ccc(-c2nnc([C@H]3C[C@H](NC(=O)c4cccc5nccnc45)C3)n2-c2ccccc2F)nc1]

[a]cLog P generated with OSIRIS Datawarrior, version 5.0.0

TABLE 2

| Compound | MLM Clint (μl/min/mg protein) | | MLM $t_{1/2}$ (min) | | HLM Clint (μl/min/mg protein) | | HLM $t_{1/2}$ (min) | |
|---|---|---|---|---|---|---|---|---|
| Example No. | average | SE | average | SE | average | SE | average | SE |
| 1 | 72 | 2 | 19 | 0.6 | 45 | 0.5 | 31 | 0.3 |
| 2 | 7 | 3 | >90 | n.a. | 17 | 0.1 | 79 | 0.6 |
| 3 | 9 | 6 | >90 | n.a. | 5 | 0.5 | >90 | n.a. |
| 4 | 19 | 0.1 | 71 | 0.2 | 5 | 2 | >90 | n.a. |
| 5 | 15 | 0.4 | >90 | n.a. | 8 | 1 | >90 | n.a. |
| Example 154 of WO 2019/243822 | 81 | 0.8 | 17 | 0.2 | 40 | 2 | 35 | 2 |

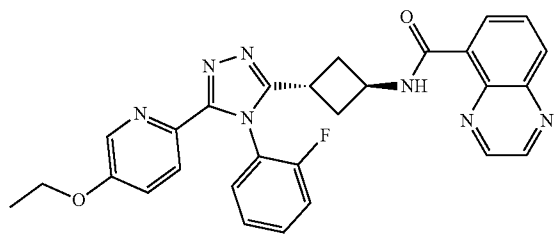 [SMILES: CCOc1ccc(-c2nnc([C@H]3C[C@H](NC(=O)c4cccc5nccnc45)C3)n2-c2ccccc2F)nc1]

The reference compound Example 154 of WO 2019/243822 has a high clearance in MLM and a moderate clearance in HLM Its cLogP value is 3.44. Each of Compounds 1 to 5 according to the invention has a cLogP value below 3. The compound of Example 1 retains a microsomal stability similar to the reference compound. However, the compounds of Examples 2 to 5 have longer MLM and HLM half lives and can thus be considered stable in MLM and HLM.

Example 7—Preparation of N-(trans-3-(5-(5-ethoxypyridin-2-yl)-4-(2-fluorophenyl)-4H-1,2,4-triazol-3-yl)cyclobutyl)pyridine-2,6-dicarboxamide

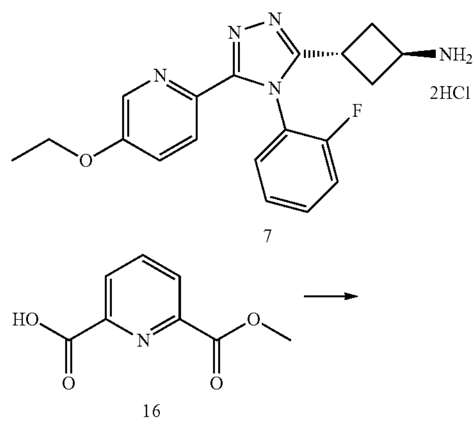

-continued

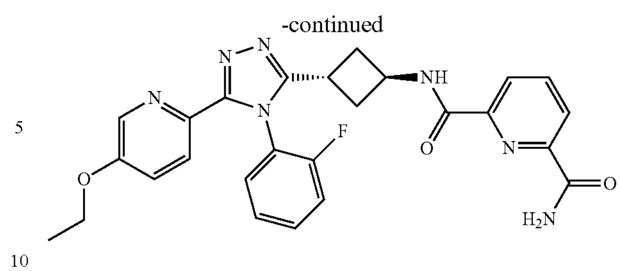

Prepared according to General Procedure A-1 giving the title compound, 43 mg (0.086 mmol), 98.46% pure, 73.1% yield as a white solid.

LCMS (ESI) m/z for C26H24FN7O3 501 (calcd) 502 ([M+H], found).

$^1$H NMR (400 MHz, DMSO) δ 9.38 (d, J=7.6 Hz, 1H), 8.88 (d, J=2.5 Hz, 1H), 8.23-8.09 (m, 3H), 8.06 (d, J=8.7 Hz, 1H), 7.94 (d, J=2.8 Hz, 1H), 7.89-7.79 (m, 1H), 7.61-7.47 (m, 3H), 7.46-7.38 (m, 1H), 7.37-7.28 (m, 1H), 4.82-4.66 (m, 1H), 4.10 (q, J=6.9 Hz, 2H), 3.32-3.29 (m, 1H), 2.86-2.75 (m, 1H), 2.68-2.58 (m, 1H), 2.57-2.51 (m, 1H), 2.49-2.42 (m, 1H), 1.31 (t, J=7.0 Hz, 3H).

Example 8—Preparation of N2-(trans-3-(5-(5-ethoxypyridin-2-yl)-4-((S)-2-fluorophenyl)-4H-1,2,4-triazol-3-yl)cyclobutyl)-N6-methylpyridine-2,6-dicarboxamide

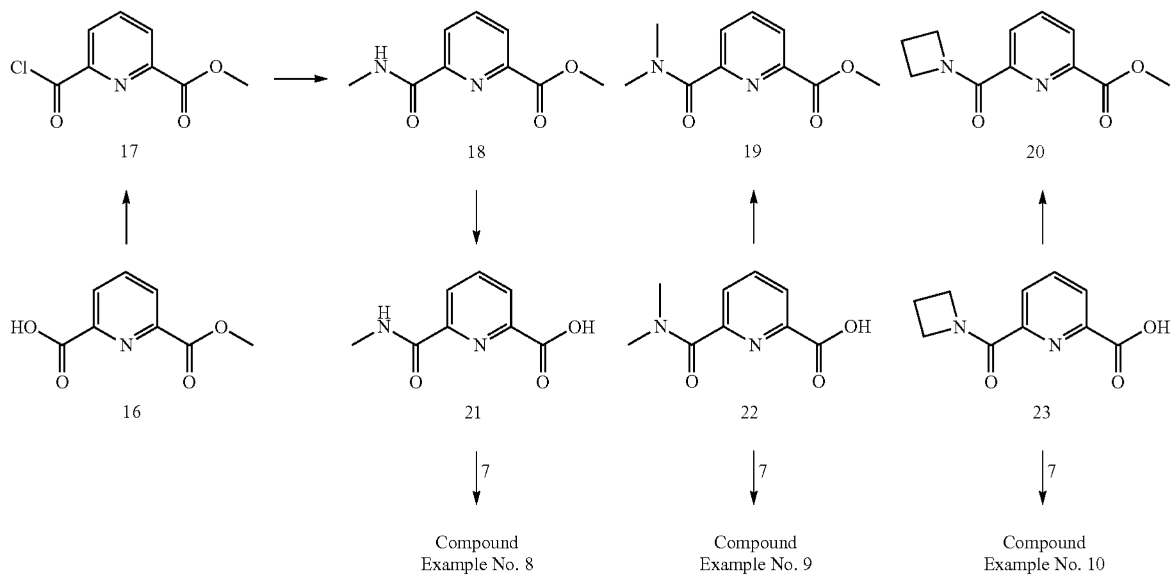

Step 1: Preparation of methyl 6-(chlorocarbonyl)picolinate (17)

Prepared according to Procedure B. 441 mg (2.208 mmol), 100% yield, 99% pure. Obtained crude was used as such in next step.

Step 2: Methyl 6-(chlorocarbonyl)picolinate 17 (1.0 equiv.) and methylamine (hydrochloride salt, 1.1 equiv.) were dissolvend/suspended in DCM (0.28M) and TEA (3.1 equiv.) was added. After overweekend, the mixture was diluted with water, extracted with DCM, dried over $Na_2SO_4$ and evaporated in vacuo giving 18, 109 mg (0.432 mmol), 77% yield, 77% pure.

Step 3: Preparation of 6-(methylcarbamoyl)picolinic Acid (21)

Prepared according to General Procedure B-1. 32 mg (0.178 mmol), 32% yield, 91% pure.

Step 4: Preparation of N2-(trans-3-(5-(5-ethoxypyridin-2-yl)-4-((S)-2-fluorophenyl)-4H-1,2,4-triazol-3-yl)cyclobutyl)-N6-methylpyridine-2,6-dicarboxamide

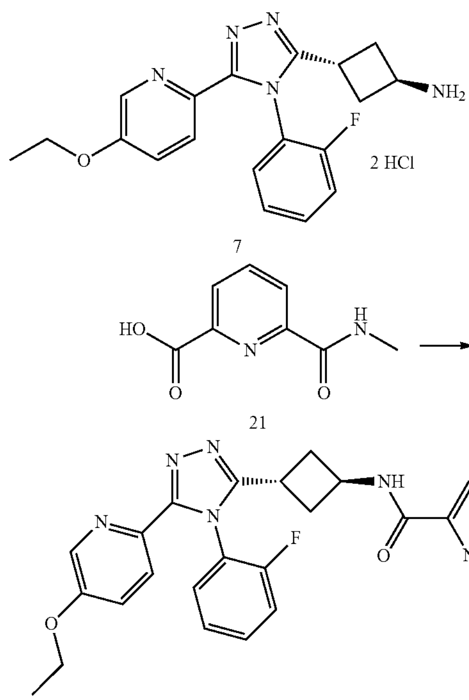

Prepared according to General Procedure A giving the title compound, 11 mg (0.021 mmol), 98.27% pure, 36.4% yield as a white solid.

LCMS (ESI) m/z for C27H26FN7O3 515 (calcd) 516 ($[M+H]^+$, found).

$^1$H NMR (400 MHz, DMSO) δ 9.28 (d, J=7.3 Hz, 1H), 9.22 (q, J=4.9 Hz, 1H), 8.21-8.11 (m, 3H), 8.06 (d, J=8.8 Hz, 1H), 7.94 (d, J=2.8 Hz, 1H), 7.62-7.53 (m, 2H), 7.50 (dd, J=8.8, 2.9 Hz, 1H), 7.47-7.38 (m, 1H), 7.37-7.28 (m, 1H), 4.81-4.64 (m, 1H), 4.10 (q, J=6.9 Hz, 2H), 3.32-3.28 (m, 1H), 2.92 (d, J=4.7 Hz, 3H), 2.87-2.77 (m, 1H), 2.70-2.51 (m, 3H), 1.31 (t, J=6.9 Hz, 3H)

Example 9—Preparation of N-(trans-3-(5-(5-ethoxypyridin-2-yl)-4-(2-fluorophenyl)-4H-1,2,4-triazol-3-yl)cyclobutyl)pyridine-2,6-dicarboxamide Step 1: Preparation of Methyl 6-(chlorocarbonyl)picolinate (17)

Prepared as for Example 8.

Step 2: Methyl 6-(chlorocarbonyl)picolinate 17 (1.0 equiv.) and dimethylamine (hydrochloride salt, 1.2 equiv.) were dissolvend/suspended in DCM (0.28M) and TEA (3.1 equiv.) was added. After overweekend, the mixture was diluted with water, extracted with DCM, dried over $Na_2SO_4$ and evaporated in vacuo giving 19, 102 mg (0.490 mmol), 87% yield, 98% pure.

Step 3: Preparation of 6-(methylcarbamoyl)picolinic Acid (22)

Prepared according to General Procedure B-1. 36 mg (0.185 mmol), 38% yield, 81% pure.

Step 4: Preparation of N-(trans-3-(5-(5-ethoxypyridin-2-yl)-4-(2-fluorophenyl)-4H-1,2,4-triazol-3-yl) cyclobutyl)pyridine-2,6-dicarboxamide

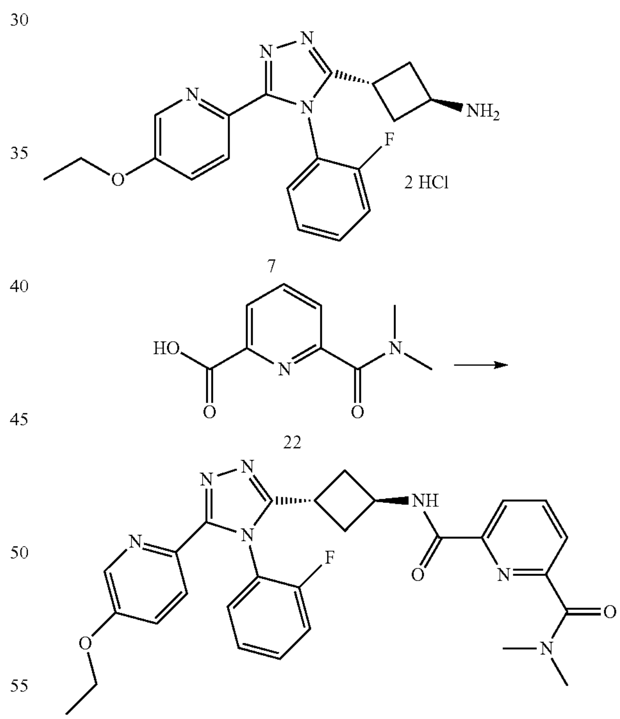

Prepared according to General Procedure A giving the title compound 7 mg (0.013 mmol), 97.36% pure, 22.5% yield as a white solid.

LCMS (ESI) m/z for C28H28FN7O3 529 (calcd) 530 ($[M+H]^+$, found).

$^1$H NMR (400 MHz, DMSO) δ 8.96 (d, J=8.3 Hz, 1H), 8.13-8.01 (m, 3H), 7.93 (d, J=2.9 Hz, 1H), 7.70 (dd, J=7.1, 1.7 Hz, 1H), 7.60-7.46 (m, 3H), 7.46-7.36 (m, 1H), 7.32 (t, J=7.5 Hz, 1H), 4.84-4.67 (m, 1H), 4.10 (q, J=7.0 Hz, 2H), 3.29-3.19 (m, 1H), 3.03 (s, 3H), 2.91 (s, 3H), 2.79-2.63 (m, 1H), 2.59-2.51 (m, 2H), 2.49-2.42 (m, 1H), 1.31 (t, J=7.0 Hz, 3H).

Example 10—Preparation of 6-(azetidine-1-carbonyl)-N-(trans-3-(5-(5-ethoxypyridin-2-yl)-4-((S)-2-fluorophenyl)-4H-1,2,4-triazol-3-yl)cyclobutyl)picolinamide Step 1: Preparation of Methyl 6-(chlorocarbonyl)picolinate (17)

Prepared as for Example 8.

Step 2: Methyl 6-(chlorocarbonyl)picolinate 17 (1.0 equiv.) and azetidine (hydrochloride salt, 1.2 equiv.) were dissolvend/suspended in DCM (0.28M) and TEA (3.1 equiv.) was added. After overweekend, the mixture was diluted with water, extracted with DCM, dried over $Na_2SO_4$ and evaporated in vacuo giving 20, 124 mg (0.563 mmol), 100% yield, 97% pure.

Step 3: Preparation of 6-(methylcarbamoyl)picolinic acid (23)

Prepared according to General Procedure B-1. 55 mg (0.185 mmol), 47% yield, 86% pure.

Step 4: Preparation of 6-(azetidine-1-carbonyl)-N-(trans-3-(5-(5-ethoxypyridin-2-yl)-4-((S)-2-fluorophenyl)-4H-1,2,4-triazol-3-yl)cyclobutyl)picolinamide

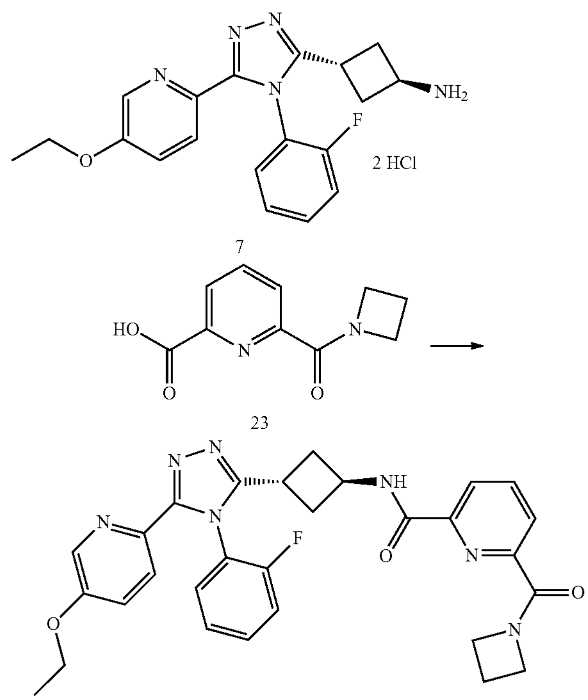

7

23

Prepared according to General Procedure A giving the title compound, 5 mg (0.009 mmol), 91.01% pure, 15.7% yield as a white solid.

LCMS (ESI) m/z for C29H28FN7O3 541 (calcd) 542 ($[M+H]^+$, found).

$^1$H NMR (400 MHz, DMSO) δ 8.63 (d, J=8.2 Hz, 1H), 8.18-8.01 (m, 4H), 7.93 (d, J=3.0 Hz, 1H), 7.61-7.47 (m, 3H), 7.46-7.37 (m, 1H), 7.36-7.27 (m, 1H), 4.83-4.59 (m, 3H), 4.10 (q, J=7.0 Hz, 4H), 3.29-3.21 (m, 1H), 2.81-2.70 (m, 1H), 2.60-2.53 (m, 1H), 2.49-2.38 (m, 2H), 2.35-2.21 (m, 2H), 1.31 (t, J=6.9 Hz, 3H).

Example 11—Preparation of N-(trans-3-(5-(5-ethoxypyridin-2-yl)-4-(2-fluorophenyl)-4H-1,2,4-triazol-3-yl)cyclobutyl)-6-oxo-1,6-dihydropyridine-2-carboxamide

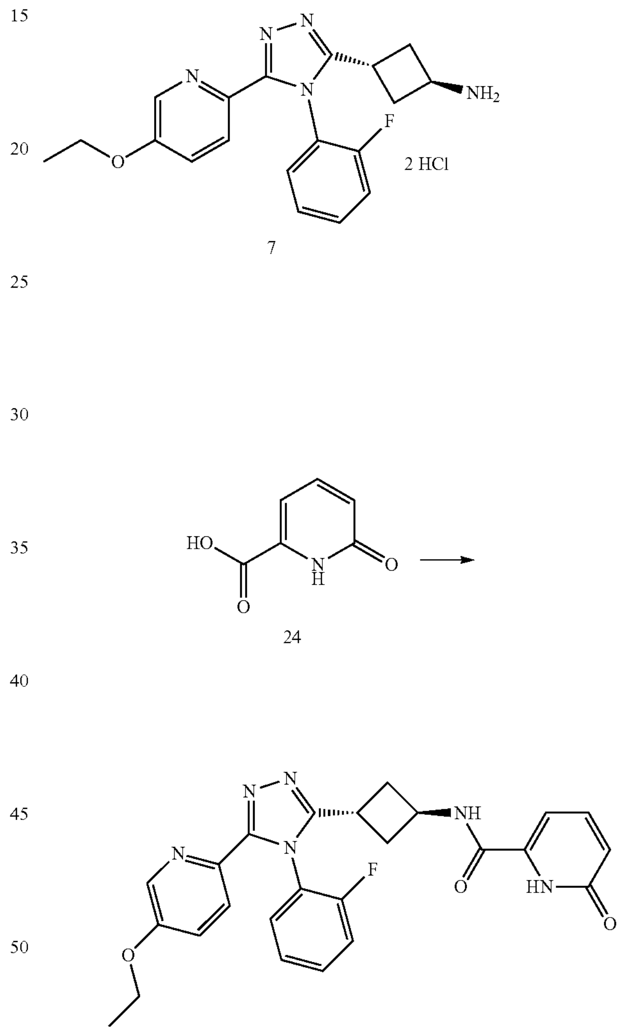

7

24

Prepared according to General Procedure A giving the title compound, 12 mg (0.025 mmol), 99.38% pure, 44.5% yield as a white solid.

LCMS (ESI) m/z for C25H23FN6O3 474 (calcd) 475 ($[M+H]^+$, found).

$^1$H NMR (400 MHz, DMSO) δ 12.24-9.41 (m, 1H), 8.74 (d, J=7.6 Hz, 1H), 8.04 (d, J=8.7 Hz, 1H), 7.93 (d, J=2.9 Hz, 1H), 7.69-7.61 (m, 1H), 7.60-7.46 (m, 3H), 7.45-7.37 (m, 1H), 7.36-7.27 (m, 1H), 7.21-7.08 (m, 1H), 6.68 (d, J=8.6 Hz, 1H), 4.70-4.52 (m, 1H), 4.09 (q, J=7.0 Hz, 2H), 3.28-3.20 (m, 1H), 2.79-2.68 (m, 1H), 2.61-2.52 (m, 1H), 2.42-2.24 (m, 2H), 2.08 (s, 1H), 1.31 (t, J=7.0 Hz, 3H).

Example 12—Preparation of N-(trans-3-(5-(5-ethoxypyridin-2-yl)-4-(2-fluorophenyl)-4H-1,2,4-triazol-3-yl)cyclobutyl)pyridine-2,6-dicarboxamide

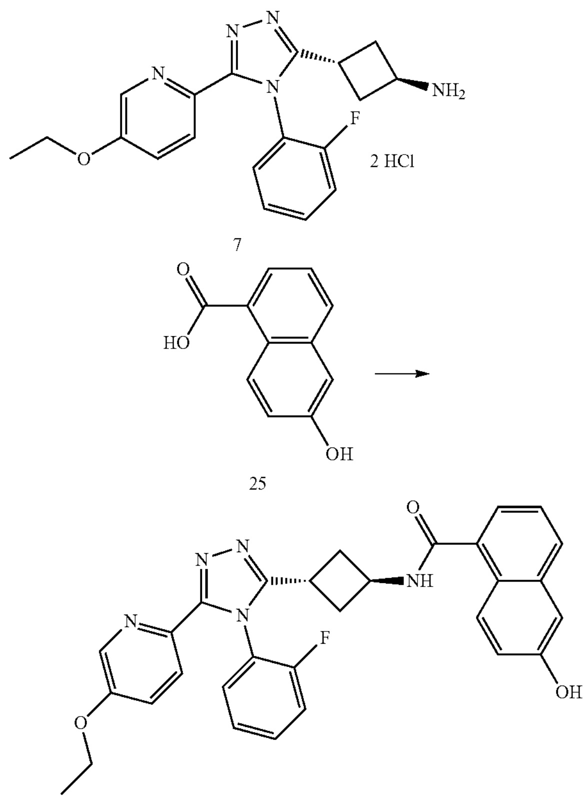

7

25

Prepared according to General Procedure A giving the title compound, 5 mg (9.55 μmol), 97.60% pure, 16.8% yield as a white solid.

LCMS (ESI) m/z for C30H26FN5O3 523 (calcd) 524 ($[M+H]^+$, found).

$^1$H NMR (400 MHz, DMSO) δ 10.52-9.22 (m, 1H), 8.82 (d, J=7.3 Hz, 1H), 8.05 (d, J=8.8 Hz, 1H), 8.00-7.89 (m, 2H), 7.74 (d, J=8.2 Hz, 1H), 7.63-7.46 (m, 3H), 7.46-7.24 (m, 4H), 7.19-7.01 (m, 2H), 4.77-4.58 (m, 1H), 4.10 (q, J=6.9 Hz, 2H), 3.30-3.26 (m, 1H), 2.87-2.72 (m, 1H), 2.66-2.56 (m, 1H), 2.41-2.20 (m, 2H), 1.31 (t, J=7.0 Hz, 3H).

Example 13—Preparation of N-(trans-3-(5-(5-ethoxypyridin-2-yl)-4-(2-fluorophenyl)-4H-1,2,4-triazol-3-yl)cyclobutyl)-2-oxo-1,2-dihydroquinoline-5-carboxamide

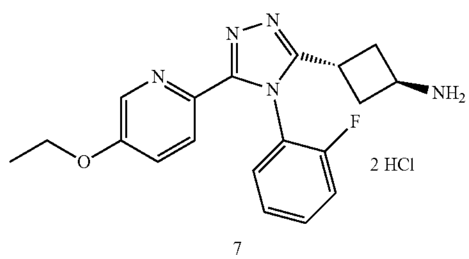

7

-continued

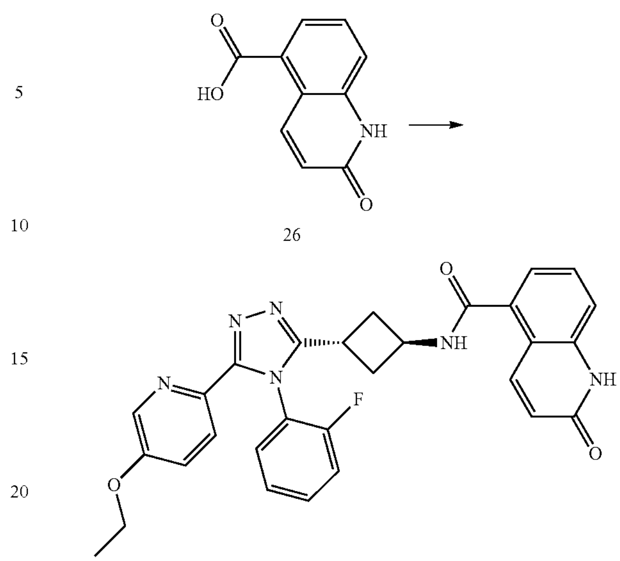

26

Prepared according to General Procedure A giving the title compound, 20 mg (0.038 mmol), 95.05% pure, 67.0% yield as a white solid.

LCMS (ESI) m/z for C29H25FN6O3 524 (calcd) 525 ([M+H]Y, found).

$^1$H NMR (400 MHz, DMSO) δ 11.86 (s, 1H), 8.92 (d, J=7.3 Hz, 1H), 8.06 (t, J=9.1 Hz, 2H), 7.93 (d, J=3.0 Hz, 1H), 7.62-7.46 (m, 4H), 7.45-7.36 (m, 2H), 7.32 (t, J=7.6 Hz, 1H), 7.24 (d, J=7.2 Hz, 1H), 6.54 (d, J=9.9 Hz, 1H), 4.72-4.55 (m, 1H), 4.10 (q, J=7.0 Hz, 2H), 3.31-3.26 (m, 1H), 2.85-2.72 (m, 1H), 2.65-2.56 (m, 1H), 2.38-2.22 (m, 2H), 1.31 (t, J=7.0 Hz, 3H).

Example 14—Preparation of N-(trans-3-(5-(5-ethoxypyridin-2-yl)-4-(2-fluorophenyl)-4H-1,2,4-triazol-3-yl)cyclobutyl)-4-hydroxyquinoline-8-carboxamide

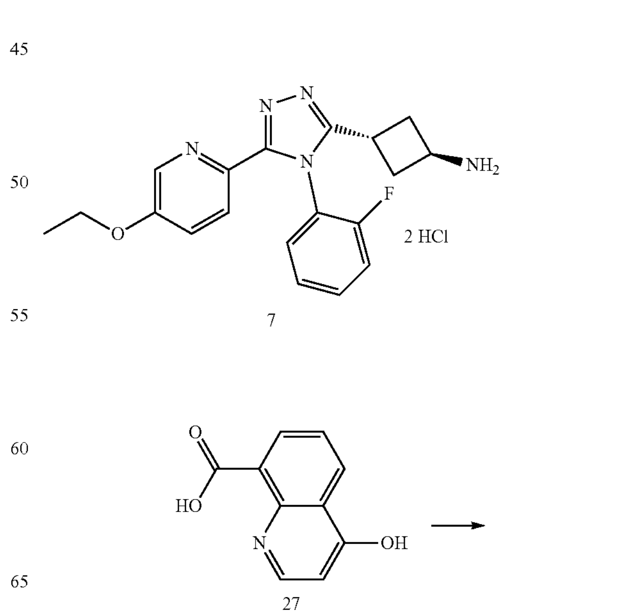

7

27

-continued

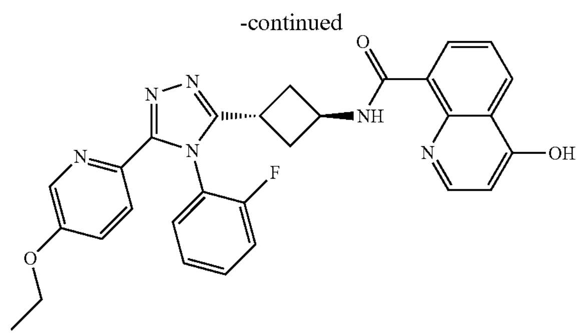

Prepared according to General Procedure A giving the title compound, 19 mg (0.036 mmol), 100% pure, 63.7% yield as an off-white solid.

LCMS (ESI) m/z for C29H25FN6O3 524 (calcd) 525 ($[M+H]^+$, found).

$^1$H NMR (400 MHz, DMSO) δ 12.00 (s, 1H), 9.17 (d, J=6.9 Hz, 1H), 8.28 (dd, J=8.0, 1.4 Hz, 1H), 8.11 (d, J=7.3 Hz, 1H), 8.05 (d, J=8.7 Hz, 1H), 7.96-7.88 (m, 2H), 7.62-7.47 (m, 3H), 7.46-7.28 (m, 3H), 6.08 (d, J=7.4 Hz, 1H), 4.76-4.61 (m, 1H), 4.10 (q, J=6.9 Hz, 2H), 3.41-3.36 (m, 1H), 2.90-2.77 (m, 1H), 2.71-2.57 (m, 1H), 2.48-2.29 (m, 2H), 1.31 (t, J=6.9 Hz, 3H).

Example 15—Preparation of N-(trans-3-(5-(5-ethoxypyridin-2-yl)-4-(2-fluorophenyl)-4H-1,2,4-triazol-3-yl)cyclobutyl)-3-hydroxybenzamide

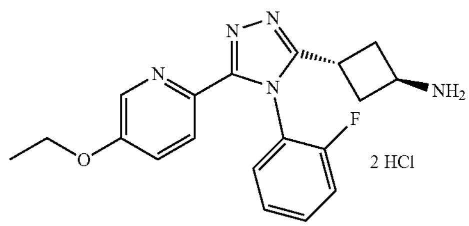

7

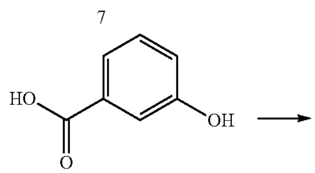

28

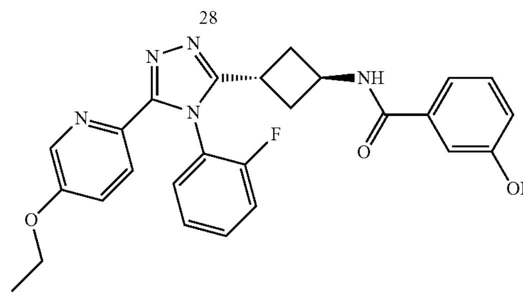

Prepared according to General Procedure A giving the title compound, 5 mg (10.56 μmol), 97.33% pure, 18.6% yield as an off-white solid.

LCMS (ESI) m/z for C26H24FN5O3 473 (calcd) 474 ($[M+H]^+$, found).

$^1$H NMR (400 MHz, DMSO) δ 10.25-8.92 (m, 1H), 8.61 (d, J=7.3 Hz, 1H), 8.04 (d, J=8.8 Hz, 1H), 7.93 (d, J=2.9 Hz, 1H), 7.62-7.45 (m, 3H), 7.42 (t, J=9.1 Hz, 1H), 7.32 (t, J=7.6 Hz, 1H), 7.27-7.16 (m, 3H), 6.92-6.82 (m, 1H), 4.68-4.51 (m, 1H), 4.10 (q, J=7.0 Hz, 2H), 3.29-3.25 (m, 1H), 2.80-2.66 (m, 1H), 2.61-2.53 (m, 1H), 2.38-2.23 (m, 2H), 1.31 (t, J=6.9 Hz, 3H).

Example 16—Preparation of N-(trans-3-(5-(5-ethoxypyridin-2-yl)-4-(2-fluorophenyl)-4H-1,2,4-triazol-3-yl)cyclobutyl)-3-sulfamoylbenzamide

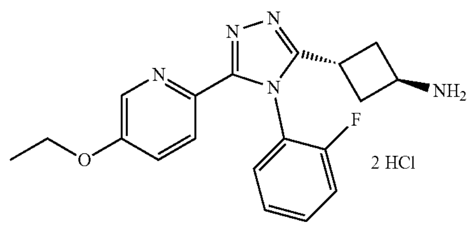

7

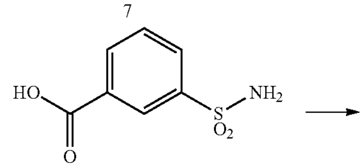

29

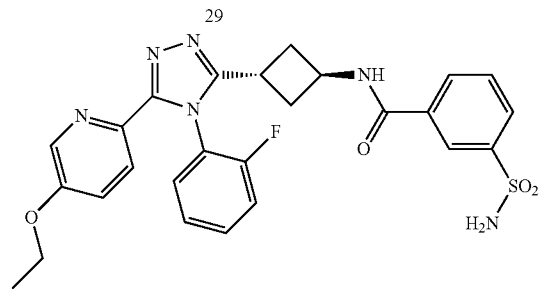

Prepared according to General Procedure A giving the title compound, 20 mg (0.037 mmol), 95.19% pure, 65.5% yield as an off-white solid.

LCMS (ESI) m/z for C26H25FN6O4S 536 (calcd) 537 ($[M+H]^+$, found).

$^1$H NMR (400 MHz, DMSO) δ 8.99 (d, J=7.3 Hz, 1H), 8.31-8.25 (m, 1H), 8.08-8.01 (m, 2H), 7.97-7.90 (m, 2H), 7.66 (t, J=7.8 Hz, 1H), 7.61-7.47 (m, 3H), 7.46-7.37 (m, 3H), 7.36-7.29 (m, 1H), 4.71-4.58 (m, 1H), 4.09 (q, J=7.0 Hz, 2H), 3.33-3.27 (m, 1H), 2.82-2.73 (m, 1H), 2.64-2.54 (m, 1H), 2.43-2.25 (m, 2H), 1.30 (t, J=7.0 Hz, 3H).

Example 17—Preparation of 2-((trans-3-(5-(5-ethoxypyridin-2-yl)-4-(2-fluorophenyl)-4H-1,2,4-triazol-3-yl)cyclobutyl)carbamoyl)pyridine 1-oxide

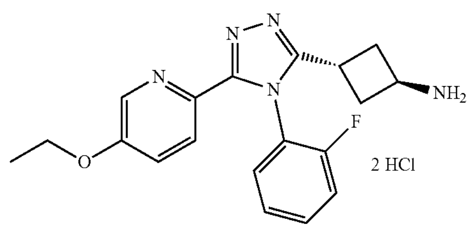

7

-continued

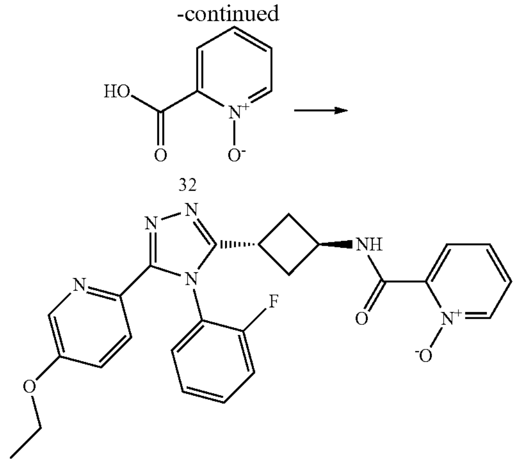

32

Prepared according to General Procedure A giving the title compound, 15 mg (0.032 mmol), 98.03% pure, 55.6% yield as a white solid.

LCMS (ESI) m/z for C25H23FN6O3 474 (caled) 475 ([M+H]$^+$, found).

$^1$H NMR (400 MHz, DMSO) δ 11.41 (d, J=7.1 Hz, 1H), 8.42 (dd, J=5.7, 1.7 Hz, 1H), 8.18 (dd, J=7.5, 2.7 Hz, 1H), 8.04 (d, J=8.7 Hz, 1H), 7.93 (d, J=2.9 Hz, 1H), 7.65-7.45 (m, 5H), 7.45-7.37 (m, 1H), 7.36-7.27 (m, 1H), 4.74-4.60 (m, 1H), 4.10 (q, J=6.9 Hz, 2H), 3.32-3.27 (m, 1H), 2.86-2.76 (m, 1H), 2.66-2.56 (m, 1H), 2.41-2.24 (m, 2H), 1.31 (t, J=6.9 Hz, 3H).

Example 18—Preparation of 3-((trans-3-(5-(5-ethoxypyridin-2-yl)-4-(2-fluorophenyl)-4H-1,2,4-triazol-3-yl)cyclobutyl)carbamoyl)pyridine 1-oxide

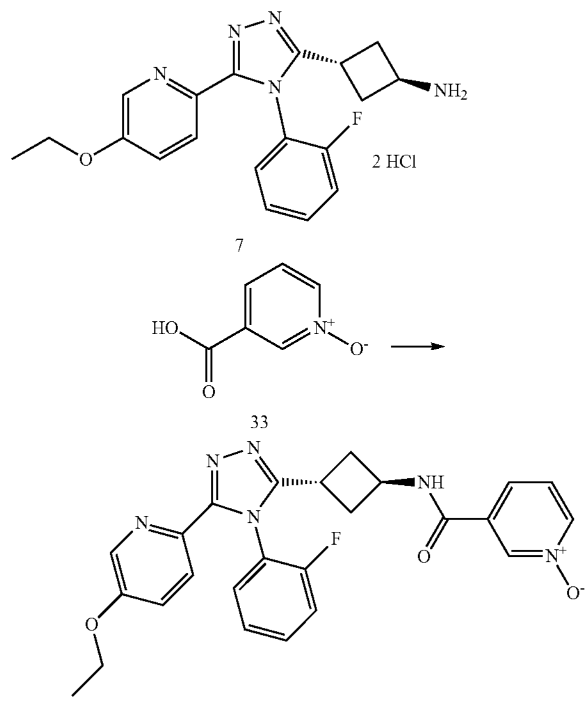

7

33

Prepared according to General Procedure A giving the title compound, 21 mg (0.044 mmol), 100% pure, 78.0% yield as a white solid.

LCMS (ESI) m/z for C25H23FN6O3 474 (calcd) 475 ([M+H]$^+$, found).

$^1$H NMR (400 MHz, DMSO) δ 8.99 (d, J=7.0 Hz, 1H), 8.59 (t, J=1.8 Hz, 1H), 8.37-8.29 (m, 1H), 8.04 (d, J=8.8 Hz, 1H), 7.93 (d, J=2.9 Hz, 1H), 7.74-7.66 (m, 1H), 7.61-7.47 (m, 4H), 7.46-7.38 (m, 1H), 7.35-7.29 (m, 1H), 4.70-4.50 (m, 1H), 4.09 (q, J=7.0 Hz, 2H), 3.32-3.25 (m, 1H), 2.84-2.72 (m, 1H), 2.64-2.54 (m, 1H), 2.41-2.22 (m, 2H), 1.31 (t, J=7.0 Hz, 3H).

Example 19—Preparation of 4-((trans-3-(5-(5-ethoxypyridin-2-yl)-4-(2-fluorophenyl)-4H-1,2,4-triazol-3-yl)cyclobutyl)carbamoyl)pyridine 1-oxide

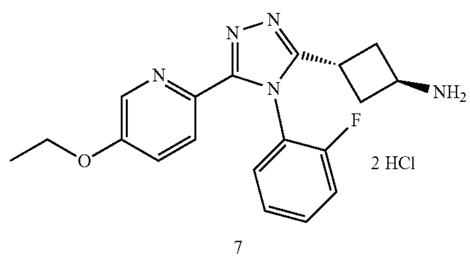

7

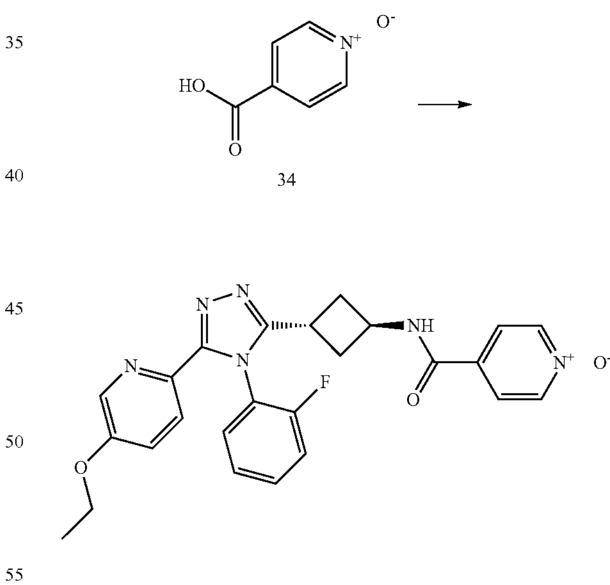

34

Prepared according to General Procedure A giving the title compound, 19 mg (0.040 mmol), 100% pure, 70.4% yield as a white solid.

LCMS (ESI) m/z for C25H23FN6O3 474 (caled) 475 ([M+H]$^+$, found).

$^1$H NMR (400 MHz, DMSO) δ 8.94 (d, J=7.0 Hz, 1H), 8.34-8.26 (m, 2H), 8.04 (d, J=8.8 Hz, 1H), 7.93 (d, J=2.8 Hz, 1H), 7.84-7.78 (m, 2H), 7.62-7.46 (m, 3H), 7.46-7.38 (m, 1H), 7.36-7.28 (m, 1H), 4.67-4.52 (m, 1H), 4.10 (q, J=7.0 Hz, 2H), 3.33-3.28 (m, 1H), 2.84-2.71 (m, 1H), 2.65-2.53 (m, 1H), 2.41-2.22 (m, 2H), 1.31 (t, J=7.0 Hz, 3H).

Example 20—Preparation of 6-amino-N-(trans-3-(5-(5-ethoxypyridin-2-yl)-4-(2-fluorophenyl)-4H-1,2,4-triazol-3-yl)cyclobutyl)picolinamide

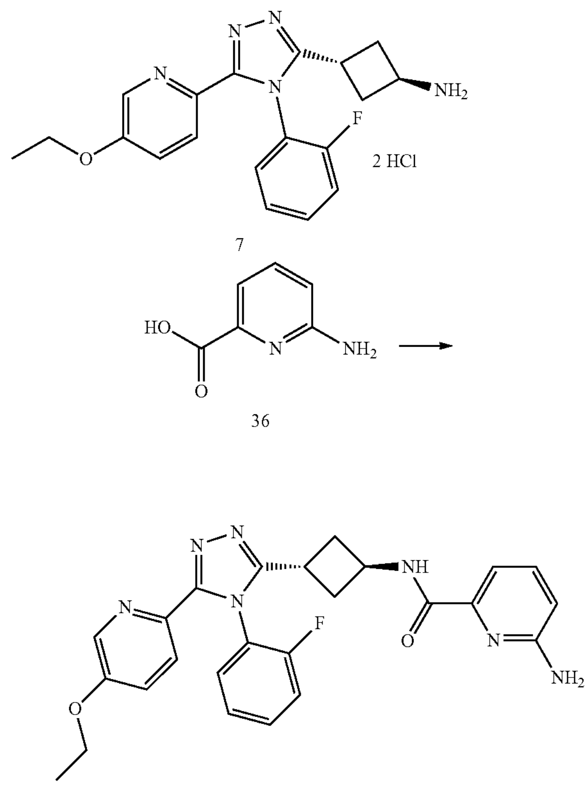

7

36

Prepared according to General Procedure A giving the title compound, 4 mg (0.008 mmol), 99.78% pure, 18.0% yield as a white solid.

LCMS (ESI) m/z for C25H24FN7O2 473 (calcd) 474 ($[M+H]^+$, found).

$^1H$ NMR (400 MHz, DMSO) δ 8.51 (d, J=8.3 Hz, 1H), 8.04 (d, J=8.7 Hz, 1H), 7.92 (d, J=2.8 Hz, 1H), 7.62-7.46 (m, 4H), 7.45-7.37 (m, 1H), 7.32 (t, J=7.8 Hz, 1H), 7.12 (d, J=7.2 Hz, 1H), 6.61 (d, J=8.3 Hz, 1H), 6.09 (s, 2H), 4.74-4.56 (m, 1H), 4.09 (q, J=7.0 Hz, 2H), 3.30-3.19 (m, 1H), 2.78-2.68 (m, 1H), 2.61-2.53 (m, 1H), 2.44-2.25 (m, 2H), 1.30 (t, J=7.0 Hz, 3H).

Example 21—Preparation of N-(trans-3-(5-(5-ethoxypyridin-2-yl)-4-(2-fluorophenyl)-4H-1,2,4-triazol-3-yl)cyclobutyl)-8-hydroxyquinoline-2-carboxamide

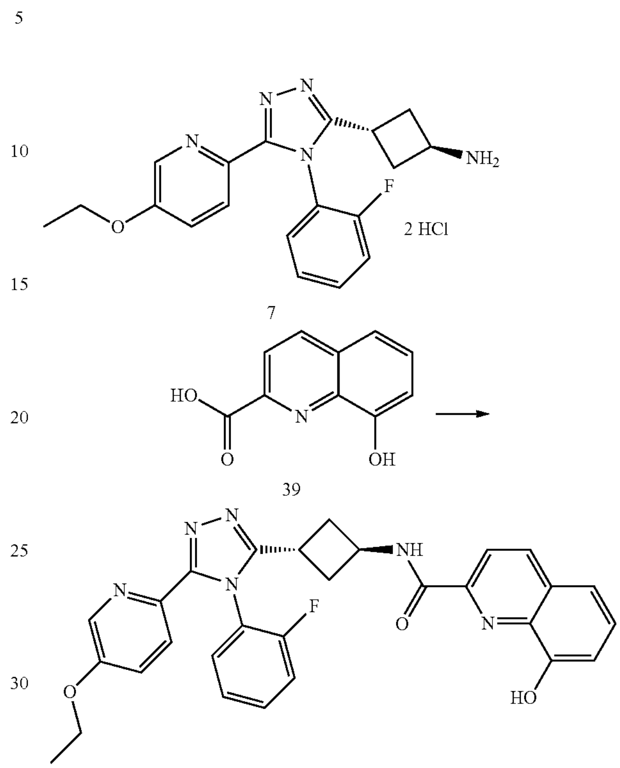

7

39

Prepared according to General Procedure A giving the title compound, 15 mg (0.029 mmol), 99.32% pure, 61.0% yield as a white solid.

LCMS (ESI) m/z for C29H25FN6O3 524 (calcd) 525 ($[M+H]^+$, found).

1H NMR (400 MHz, DMSO) δ 10.11 (s, 1H), 9.72 (d, J=7.6 Hz, 1H), 8.49 (d, J=8.6 Hz, 1H), 8.12 (d, J=8.5 Hz, 1H), 8.06 (d, J=8.8 Hz, 1H), 7.94 (d, J=2.9 Hz, 1H), 7.62-7.39 (m, 6H), 7.33 (t, J=7.7 Hz, 1H), 7.18 (dd, J=7.6, 1.2 Hz, 1H), 4.84-4.66 (m, 1H), 4.10 (q, J=6.9 Hz, 2H), 3.43-3.36 (m, 1H), 2.91-2.81 (m, 1H), 2.77-2.60 (m, 1H), 2.48-2.38 (m, 2H), 1.31 (t, J=7.0 Hz, 3H).

Example 22—Preparation of N-(trans-3-(5-(5-ethoxypyridin-2-yl)-4-(2-fluorophenyl)-4H-1,2,4-triazol-3-yl)cyclobutyl)phenazine-1-carboxamide

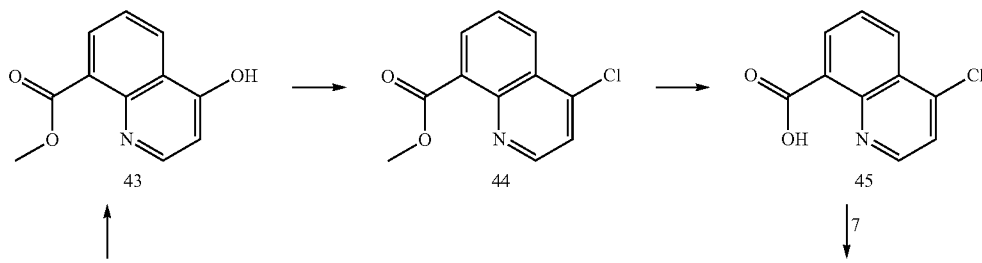

43

44

45

-continued

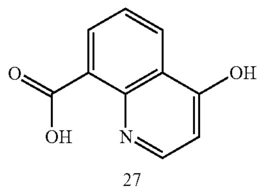

27

Compound
Example No. 22

Step 1: Preparation of Methyl 4-hydroxyquinoline-8-carboxylate (43)

Prepared according to Procedure C. 35 mg (0.172 mmol), 33% yield, 84% pure. Obtained oil was used as such in next step.

Step 2: Methyl 4-hydroxyquinoline-8-carboxylate 43 (1.0 equiv.) was added to $POCl_3$ (62.3 equiv.). After 2 h stirring at 100° C., the mixture was reduced in vacuo and purified on a silica column eluted with heptane/ethyl acetate 0-100%. Product fractions were reduced in vacuo giving 44. 42 mg (0.142 mmol), 83% yield, 75% pure.

Step 3: Preparation of 4-chloroquinoline-8-carboxylic Acid (45)

Prepared according to General Procedure B-1. The residue was purified on a ReproSil-Pur C18 reversed phase column eluted with water/acetonitrile 30-70% containing 0.1% formic acid to afford 45. 17 mg (0.082 mmol), 43% yield, 100% pure.

Step 4: Preparation of N-(trans-3-(5-(5-ethoxypyridin-2-yl)-4-(2-fluorophenyl)-4H-1,2,4-triazol-3-yl)cyclobutyl)phenazine-1-carboxamide

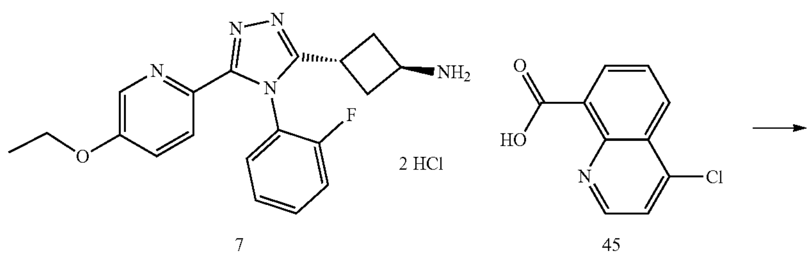

7

45

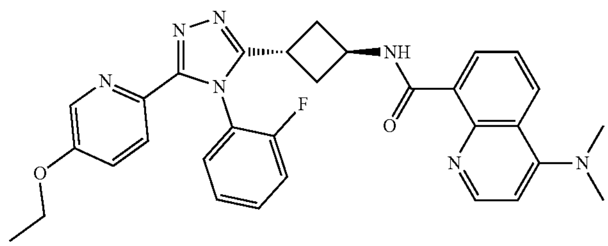

45 (1.1 equiv.) and HATU (1.1 equiv.) were dissolved in anhydrous DMF (dry) (0.02 M) and DIPEA (2.0 equiv.) was added. After 1 h, amine 7 (1.0 equiv.) and DIPEA (2.0 equiv.) in DMF (dry) (0.02M) was added. After 1 h, 7 M ammonia in methanol (10 equiv.) was added. After overnight, the crude reaction mixture was purified on a ReproSil-Pur C18 reversed phase column eluted with water/acetonitrile 30-70% containing 0.1% formic acid. Product fractions were lyophilized to afford the title compound, 9 mg (0.016 mmol), 99.72% pure, 21.7% yield as a white solid.

LCMS (ESI) m/z for C31H30FN7O2 551 (calcd) 552 ($[M+H]^+$, found).

$^1H$ NMR (400 MHz, DMSO) δ 13.71 (s, 1H), 8.53 (s, 1H), 8.39 (d, J=7.4 Hz, 2H), 8.05 (d, J=8.8 Hz, 1H), 7.93 (d, J=2.9 Hz, 1H), 7.68-7.59 (m, 1H), 7.58-7.46 (m, 3H), 7.46-7.38 (m, 1H), 7.37-7.28 (m, 1H), 7.00 (d, J=6.4 Hz, 1H), 4.81-4.64 (m, 1H), 4.10 (q, J=6.9 Hz, 2H), 3.41-3.36 (m, 1H), 3.25 (s, 6H), 2.92-2.78 (m, 1H), 2.72-2.60 (m, 1H), 2.47-2.28 (m, 2H), 1.31 (t, J=7.0 Hz, 3H).

Example 23—Preparation of N-(trans-3-(5-(5-ethoxypyridin-2-yl)-4-(2-fluorophenyl)-4H-1,2,4-triazol-3-yl)cyclobutyl)-3-hydroxyquinoline-8-carboxamide

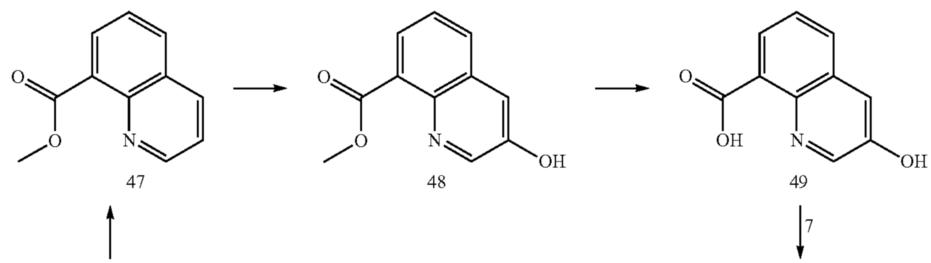

47

48

49

Compound Example No. 23

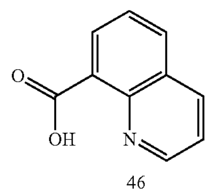

46

Step 1: Preparation of Methyl Quinoline-8-carboxylate (47)

Prepared according to Procedure C. 195 mg (1.042 mmol), 93% yield, 93% pure. Obtained oil was used as such in next step.

Step 2: Hydrogen peroxide (30%, 2 equiv.) was added to 47 (1.0 equiv.) in acetic acid (25 equiv.). After overnight at 70° C., the mixture was reduced in vacuo and purified on a silica column eluted with DCM/MeOH 0-10%. Product fractions were reduced in vacuo giving 48. 43 mg (0.212 mmol), 40% yield, 80% pure. Product identity assigned by NMR.

Step 3: Preparation of 3-hydroxyquinoline-8-carboxylic Acid (49)

Prepared according to General Procedure B-1. The residue was purified on a ReproSil-Pur C18 reversed phase column eluted with water/acetonitrile 30-70% containing 0.1% formic acid to afford 49. 17 mg (0.082 mmol), 44% yield, 100% pure.

Step 4: Preparation of N-(trans-3-(5-(5-ethoxypyridin-2-yl)-4-(2-fluorophenyl)-4H-1,2,4-triazol-3-yl)cyclobutyl)-3-hydroxyquinoline-8-carboxamide

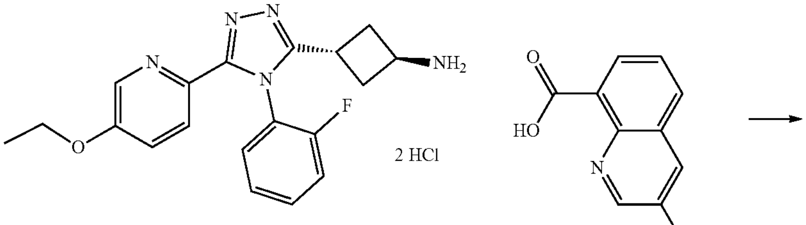

7

49

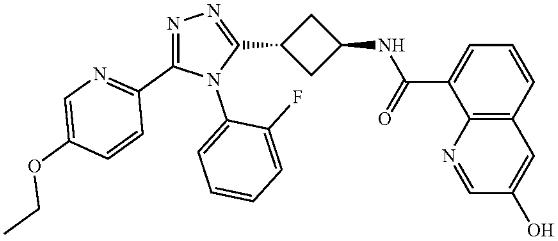

Prepared according to General Procedure A giving the title compound, 16 mg (0.031 mmol), 100% pure, 35.3% yield a white solid.

LCMS (ESI) m/z for C29H25FN6O3 524 (calcd) 525 ($[M+H]^+$, found).

$^1$H NMR (400 MHz, DMSO) δ 11.34-9.84 (m, 2H), 8.68 (d, J=2.9 Hz, 1H), 8.20 (dd, J=7.4, 1.5 Hz, 1H), 8.06 (d, J=8.7 Hz, 1H), 8.01-7.88 (m, 2H), 7.66 (d, J=2.9 Hz, 1H), 7.63-7.47 (m, 4H), 7.47-7.37 (m, 1H), 7.37-7.26 (m, 1H), 4.81-4.66 (m, 1H), 4.10 (q, J=7.0 Hz, 2H), 3.39-3.37 (m, 1H), 2.92-2.77 (m, 1H), 2.70-2.58 (m, 1H), 2.46-2.26 (m, 2H), 1.31 (t, J=7.0 Hz, 3H).

Example 24—Preparation of 5-((trans-3-(5-(5-ethoxypyridin-2-yl)-4-(2-fluorophenyl)-4H-1,2,4-triazol-3-yl)cyclobutyl)carbamoyl)-2,3-dimethylquinoxaline 1-oxide

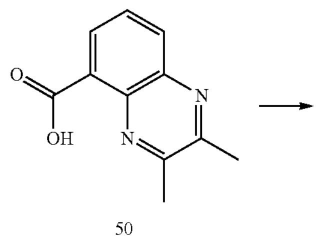

50

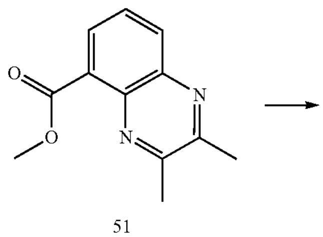

51

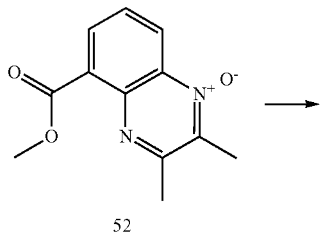

52

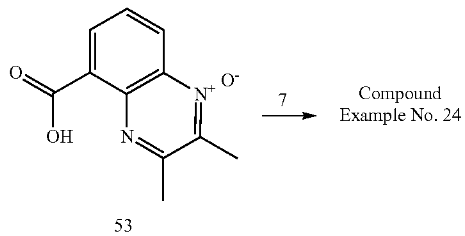

53

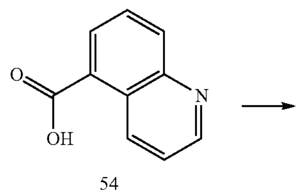

54

-continued

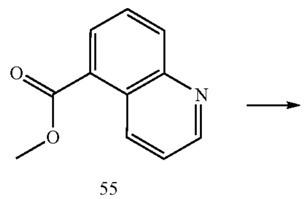

55

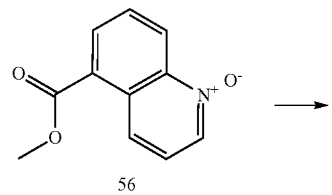

56

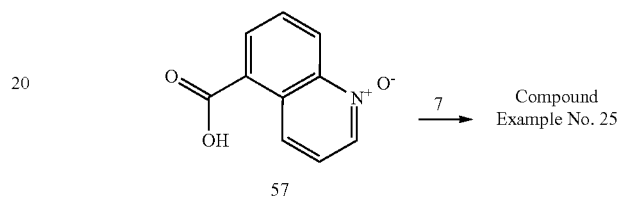

57

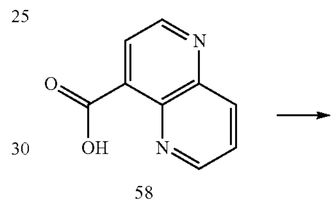

58

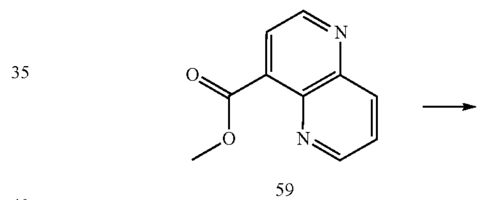

59

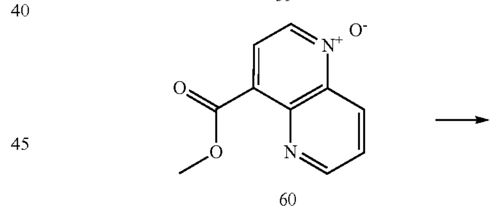

60

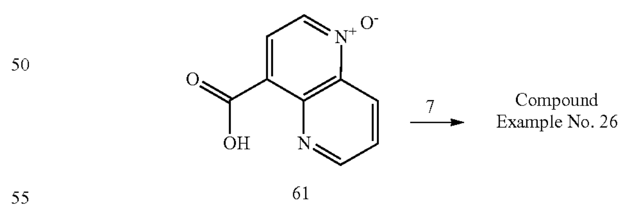

61

Step 1: Preparation of Methyl 2,3-dimethylquinoxaline-5-carboxylate (51)

Prepared according to Procedure C. 118 mg (0.546 mmol), 55% yield, 50% pure. Obtained crude was used as such in next step.

Step 2: Preparation of 5-(methoxycarbonyl)-2,3-dimethylquinoxaline 1-oxide (52)

Prepared according to Procedure D. 8 mg (0.034 mmol), 6% yield, 99% pure.

Step 3: Preparation of 5-carboxy-2,3-dimethylquinoxaline 1-oxide (53)

Prepared according to General Procedure B-1. 7.5 mg (0.034 mmol), 100% yield, 99% pure.

Step 4: Preparation of 5-((trans-3-(5-(5-ethoxypyridin-2-yl)-4-(2-fluorophenyl)-4H-1,2,4-triazol-3-yl)cyclobutyl)carbamoyl)-2,3-dimethylquinoxaline 1-oxide

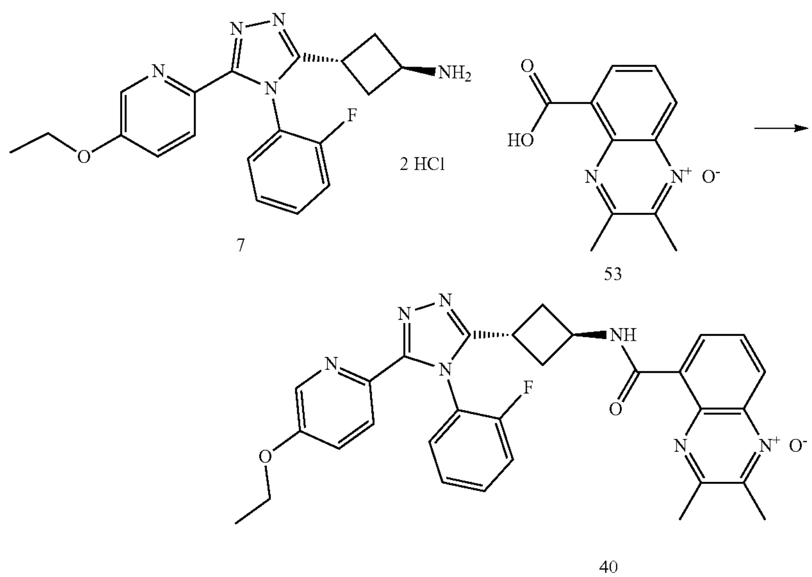

7

53

Prepared according to General Procedure A giving the title compound, 4 mg (0.007 mmol), 98.26% pure, 22.0% yield a white solid. Product identity assigned by NMR.

LCMS (ESI) m/z for C30H28FN7O3 553 (calcd) 554 ($[M+H]^+$, found).

$^1$H NMR (400 MHz, DMSO) δ 10.54 (d, J=7.2 Hz, 1H), 8.57 (dd, J=8.6, 1.6 Hz, 1H), 8.42 (dd, J=7.4, 1.5 Hz, 1H), 8.06 (d, J=8.7 Hz, 1H), 7.93 (d, J=2.9 Hz, 1H), 7.83 (t, 1H), 7.56 (t, J=8.0 Hz, 2H), 7.50 (dd, J=8.8, 2.9 Hz, 1H), 7.43 (t, J=9.2 Hz, 1H), 7.33 (t, J=7.7 Hz, 1H), 4.79-4.67 (m, 1H), 4.10 (q, J=6.9 Hz, 2H), 2.93-2.79 (m, 1H), 2.72 (s, 4H), 2.61-2.55 (m, 3H), 2.44-2.27 (m, 2H), 1.31 (t, J=7.0 Hz, 3H).

Example 25—Preparation of 5-((trans-3-(5-(5-ethoxypyridin-2-yl)-4-(2-fluorophenyl)-4H-1,2,4-triazol-3-yl)cyclobutyl)carbamoyl)quinoline 1-oxide Step 1: Preparation of Methyl Quinoline-5-carboxylate (55)

Prepared according to Procedure C. 29 mg (0.155 mmol), 67% yield, 88% pure. Obtained crude was used as such in next step.

Step 2: Preparation of 5-(methoxycarbonyl)quinoline 1-oxide (56)

Prepared according to Procedure D. 9 mg (0.044 mmol), 29% yield, 58% pure.

Step 3: Preparation of 5-carboxyquinoline 1-oxide (57)

Prepared according to General Procedure B-1. 8.4 mg (0.044 mmol), 100% yield, 84% pure.

Step 4: Preparation of 5-((trans-3-(5-(5-ethoxypyridin-2-yl)-4-(2-fluorophenyl)-4H-1,2,4-triazol-3-yl) cyclobutyl)carbamoyl)quinoline 1-oxide

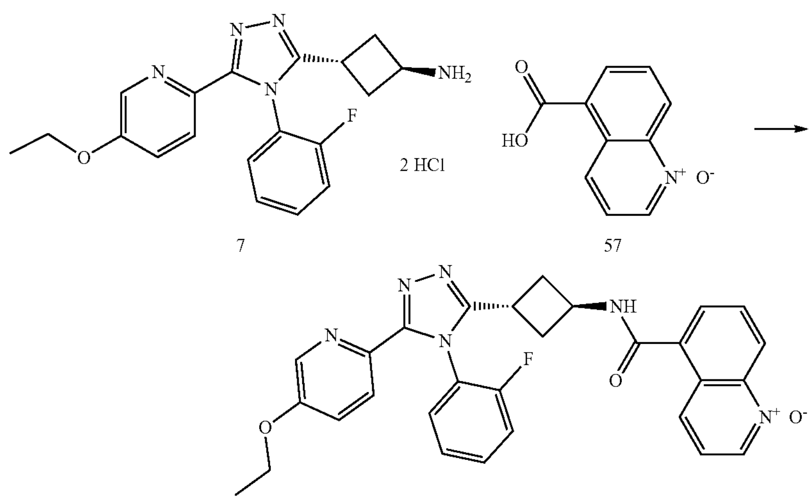

7

57

Prepared according to General Procedure A giving the title compound, 9 mg (0.017 mmol), 97.66% pure, 43.0% yield a white solid. Product identity assigned by NMR.

LCMS (ESI) m/z for C29H25FN6O3 524 (calcd) 525 ($[M+H]^+$, found).

$^1$H NMR (400 MHz, DMSO) δ 9.09 (d, J=7.2 Hz, 1H), 8.69-8.58 (m, 2H), 8.06 (t, J=9.1 Hz, 2H), 7.93 (d, J=2.9 Hz, 1H), 7.88-7.77 (m, 2H), 7.60-7.47 (m, 4H), 7.42 (t, J=9.2 Hz, 1H), 7.32 (t, J=7.7 Hz, 1H), 4.77-4.60 (m, 1H), 4.10 (q, J=7.0 Hz, 2H), 3.32-3.21 (m, 1H), 2.89-2.75 (m, 1H), 2.71-2.58 (m, 1H), 2.41-2.22 (m, 2H), 1.31 (t, J=7.0 Hz, 3H).

Example 26—Preparation of 4-((trans-3-(5-(5-ethoxypyridin-2-yl)-4-(2-fluorophenyl)-4H-1,2,4-triazol-3-yl)cyclobutyl)carbamoyl)-1,5-naphthyridine 1-oxide Step 1: Preparation of Methyl 1,5-naphthyridine-4-carboxylate (59)

Prepared according to Procedure C. 181 mg (0.962 mmol), 84% yield, 87% pure. Obtained crude was used as such in next step.

Step 2: Preparation of 4-(methoxycarbonyl)-1,5-naphthyridine 1-oxide (60)

Prepared according to Procedure D. 90 mg (0.441 mmol), 46% yield, 78% pure.

Step 3: Preparation of 4-carboxy-1,5-naphthyridine 1-oxide (61)

Prepared according to General Procedure B-1. 60 mg (0.316 mmol), 72% yield, 90% pure.

Step 4: Preparation of 4-((trans-3-(5-(5-ethoxypyridin-2-yl)-4-(2-fluorophenyl)-4H-1,2,4-triazol-3-yl)cyclobutyl)carbamoyl)-1,5-naphthyridine 1-oxide

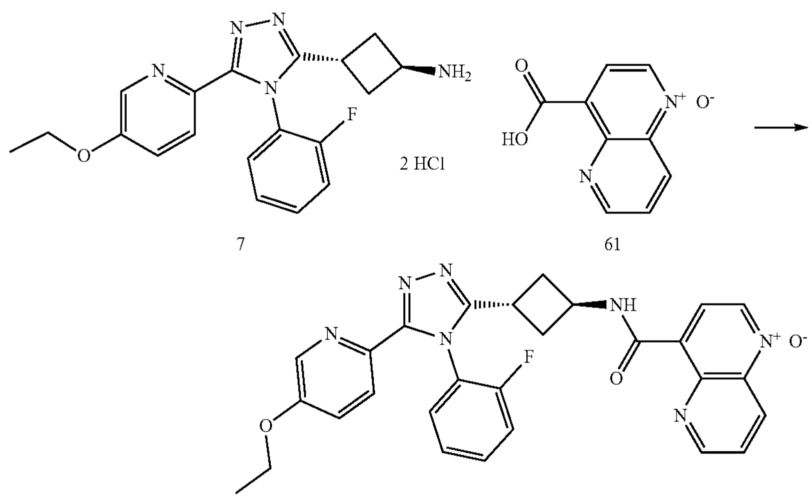

7

61

Prepared according to General Procedure A giving the title compound, 13 mg (0.025 mmol), 98.78% pure, 35.2% yield an off-white solid. Product identity assigned by NMR.

LCMS (ESI) m/z for C28H24FN7O3 525 (calcd) 526 ($[M+H]^+$, found).

$^1$H NMR (400 MHz, DMSO) δ 10.59 (d, J=7.0 Hz, 1H), 9.17 (dd, J=4.3, 1.5 Hz, 1H), 8.97 (dd, J=8.9, 1.6 Hz, 1H), 8.74 (d, J=6.5 Hz, 1H), 8.24 (d, J=6.5 Hz, 1H), 8.05 (d, J=8.8 Hz, 1H), 7.98-7.89 (m, 2H), 7.60-7.53 (m, 2H), 7.50 (dd, J=8.7, 2.9 Hz, 1H), 7.42 (t, J=9.2 Hz, 1H), 7.33 (t, J=7.7 Hz, 1H), 4.84-4.68 (m, 1H), 4.10 (q, J=6.9 Hz, 2H), 3.40-3.36 (m, 1H), 2.92-2.78 (m, 1H), 2.74-2.61 (m, 1H), 2.47-2.29 (m, 2H), 1.31 (t, J=6.9 Hz, 3H).

Examples 27 and 28—Preparation of 4-((trans-3-(5-(5-ethoxypyridin-2-yl)-4-(2-fluorophenyl)-4H-1,2,4-triazol-3-yl)cyclobutyl)carbamoyl)-7-hydroxy-1,5-naphthyridine 1-oxide and 4-((trans-3-(5-(5-ethoxypyridin-2-yl)-4-(2-fluorophenyl)-4H-1,2,4-triazol-3-yl)cyclobutyl)carbamoyl)-7-methoxy-1,5-naphthyridine 1-oxide

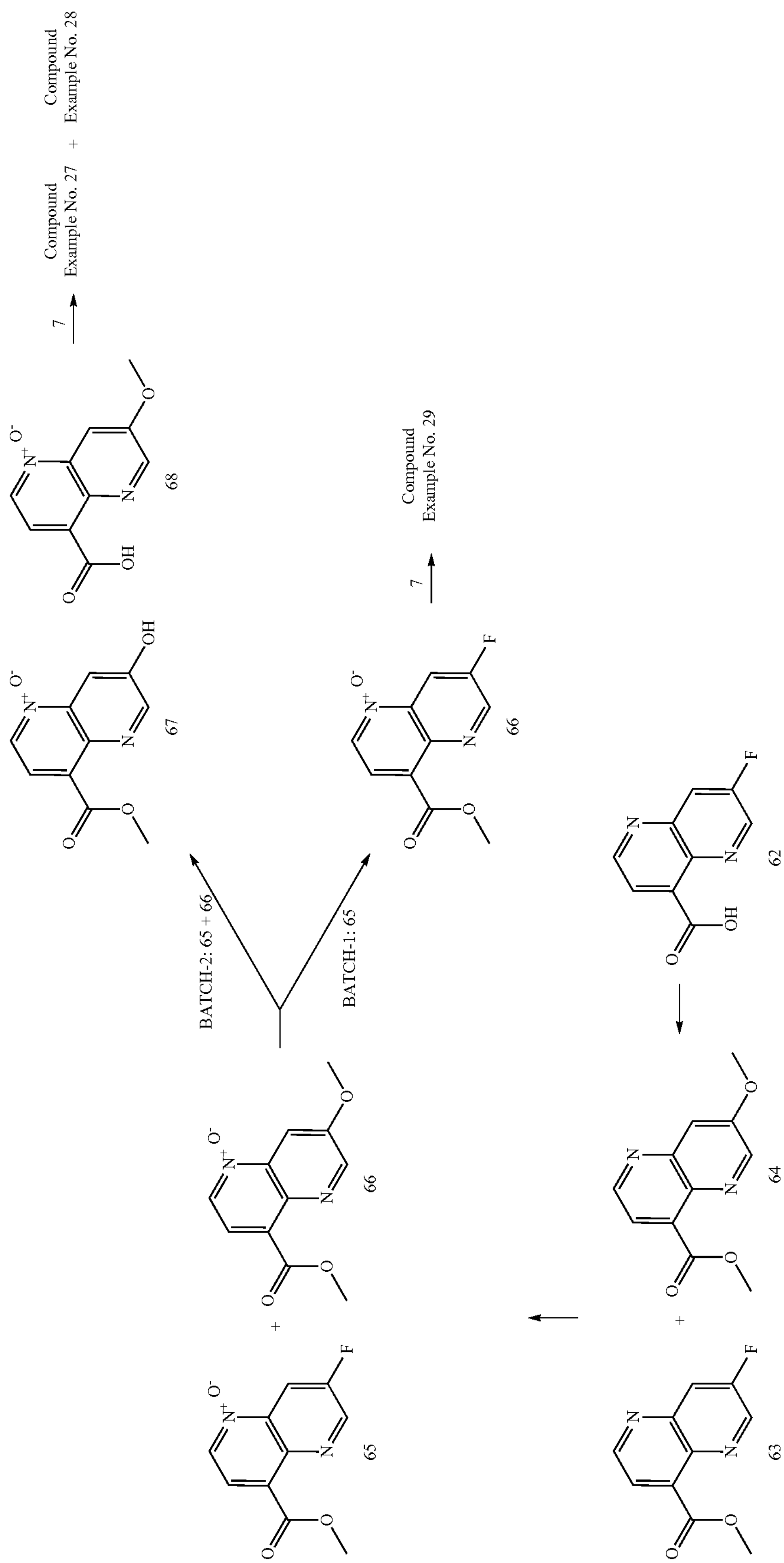
62
63
64
65
66
BATCH-1: 65
BATCH-2: 65 + 66
66
67
7
Compound Example No. 29
68
7
Compound Example No. 27
+
Compound Example No. 28

Step 1: Preparation of Methyl 7-fluoro-1,5-naphthyridine-4-carboxylate (63) and methyl 7-methoxy-, 5-naphthyridine-4-carboxylate (64)

Prepared according to Procedure C. 63 and 64 were obtained as a crude mixture 143 mg (0.694 mmol), 67% yield, 82% pure.

Step 2: Preparation of 7-fluoro-4-(methoxycarbonyl)-1,5-naphthyridine 1-oxide (65) and 7-methoxy-4-(methoxycarbonyl)-1,5-naphthyridine 1-oxide (66)

Prepared according to Procedure D. 65 and 66 were obtained as a crude mixture (BATCH-2). BATCH-2: 28 mg (0.110 mmol, purity included in calculation), 16% combined yield based on 65 and 66, 20% pure (65) and 71% pure (66).

Step 3: Preparation of 4-carboxy-7-hydroxy-1,5-naphthyridine 1-oxide (67) and 4-carboxy-7-methoxy-1,5-naphthyridine 1-oxide (68)

Prepared according to General Procedure B-1. 67 and 68 were obtained as a crude mixture 18 mg (0.084 mmol, purity included in calculation), 93% combined yield based on 67 and 68, 37.6% pure (67) and 62.2% pure (68).

Step 4: Preparation of 4-((trans-3-(5-(5-ethoxypyridin-2-yl)-4-(2-fluorophenyl)-4H-1,2,4-triazol-3-yl)cyclobutyl)carbamoyl)-7-hydroxy-1,5-naphthyridine 1-oxide and 4-((trans-3-(5-(5-ethoxypyridin-2-yl)-4-(2-fluorophenyl)-4H-1,2,4-triazol-3-yl)cyclobutyl)carbamoyl)-7-methoxy-1,5-naphthyridine 1-oxide

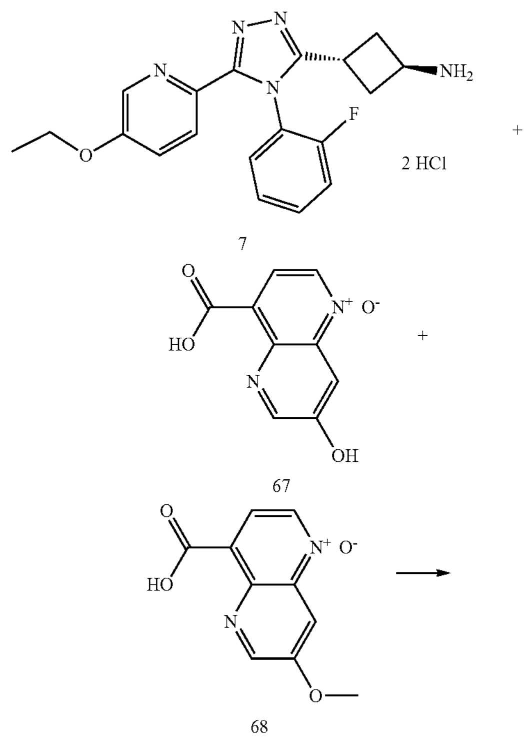

7

67

68

-continued

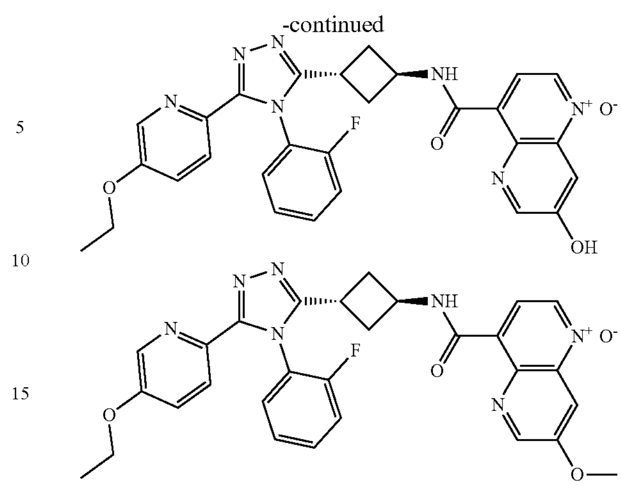

Prepared according to General Procedure A giving after purification described in General Procedure A (identity of obtained products assigned by NMR): Compound Example No. 27: 7 mg (0.013 mmol), 99.61% pure, 17.2% yield an off-white solid.

LCMS (ESI) m/z for C28H24FN7O4 541 (calcd) 542 ($[M+H]^+$, found).

$^1$H NMR (400 MHz, DMSO) δ 10.49 (d, J=7.1 Hz, 1H), 8.75 (d, J=2.8 Hz, 1H), 8.58 (d, J=6.5 Hz, 1H), 8.05 (d, J=8.8 Hz, 1H), 7.99 (d, J=2.8 Hz, 1H), 7.93 (d, J=2.9 Hz, 1H), 7.91 (d, J=6.5 Hz, 1H), 7.61-7.52 (m, 2H), 7.50 (dd, J=8.8, 2.9 Hz, 1H), 7.42 (t, J=9.1 Hz, 1H), 7.32 (t, J=7.7 Hz, 1H), 4.80-4.64 (m, 1H), 4.10 (q, J=7.0 Hz, 2H), 2.89-2.78 (m, 1H), 2.70-2.59 (m, 1H), 2.46-2.27 (m, 2H), 1.31 (t, J=6.9 Hz, 3H), one signal (1H) coincides with $H_2O$ signal.

Compound Example No. 28: 12 mg (0.022 mmol), 95.40% pure, 28.8% yield an off-white solid.

LCMS (ESI) m/z for C29H26FN7O4 555 (caled) 556 ($[M+H]^+$, found).

$^1$H NMR (400 MHz, DMSO) δ 10.29 (d, J=6.9 Hz, 1H), 8.94 (d, J=2.9 Hz, 1H), 8.72 (d, J=6.5 Hz, 1H), 8.26 (d, J=2.9 Hz, 1H), 8.07-8.01 (m, 2H), 7.93 (d, J=2.9 Hz, 1H), 7.60-7.46 (m, 3H), 7.42 (dd, J=10.0, 8.3 Hz, 1H), 7.32 (t, J=7.7 Hz, 1H), 4.82-4.64 (m, 1H), 4.13-4.06 (m, 2H), 4.05 (s, 3H), 2.91-2.73 (m, 2H), 2.71-2.59 (m, 1H), 2.47-2.27 (m, 2H), 1.31 (t, J=6.9 Hz, 3H).

Example 29—Preparation of 4-((trans-3-(5-(5-ethoxypyridin-2-yl)-4-(2-fluorophenyl)-4H-1,2,4-triazol-3-yl)cyclobutyl)carbamoyl)-7-fluoro-1,5-naphthyridine 1-oxide Step 1: Preparation of Methyl 7-fluoro-1,5-naphthyridine-4-carboxylate (63) and methyl 7-methoxy-1, 5-naphthyridine-4-carboxylate (64)

Prepared according to Procedure C. 63 and 64 were obtained as a crude mixture 143 mg (0.694 mmol), 67% yield, 82% pure.

Step 2: Preparation of 7-fluoro-4-(methoxycarbonyl)-1,5-naphthyridine 1-oxide (65)

Prepared according to Procedure D. BATCH-1: 30 mg (0.133 mmol), 19% yield, 98% pure

Step 3: Preparation of 4-carboxy-7-fluoro-1,5-naphthyridine 1-oxide (69)

$BBr_3$ (3 equiv.) was added dropwise to a cooled solution of 65 in DCM (0.09M). After overweekend at room temperature, $BBr_3$ (3 equiv.) was added to the reaction mixture. After overnight at room temperature, the reaction mixture was added slowly to ice and extracted with DCM (+5% MeCN). The organic layer was dried over sodium sulfate and reduced in vacuo. The crude was purified on a ReproSil-Pur C18 reversed phase column eluted with water/acetonitrile 30-70% containing 0.1% formic acid. Product fractions were reduced in vacuo to afford 69 as an off-white solid. 7 mg (0.034 mmol), 37% yield, 100% pure.

Step 4: Preparation of 4-((trans-3-(5-(5-ethoxypyridin-2-yl)-4-(2-fluorophenyl)-4H-1,2,4-triazol-3-yl)cyclobutyl)carbamoyl)-7-fluoro-1,5-naphthyridine

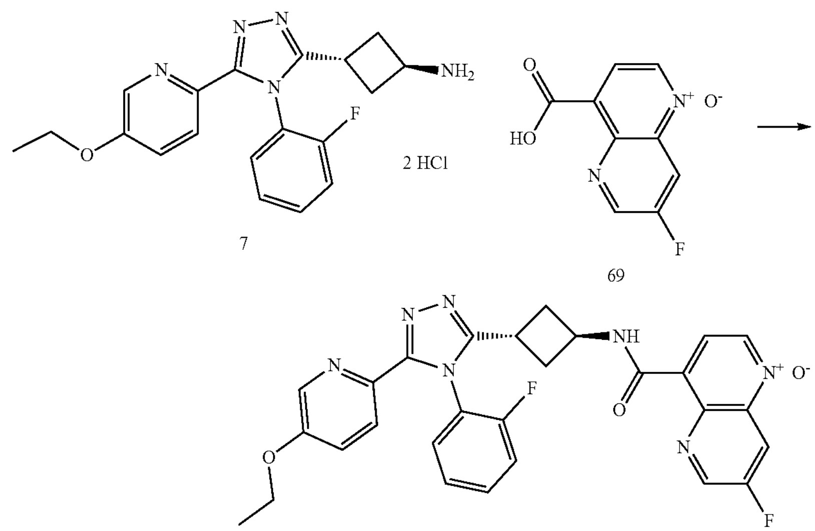

7

2 HCl

69

4-carboxy-7-fluoro-1,5-naphthyridine 1-oxide 69 (1 equiv.), DIPEA (2 equiv.) and TFFH (1.1 equiv.) were added to DMF(dry) (0.14M). After 1 h, 7 and DIPEA (2 equiv.) were added to the mixture. After 2 h, The crude reaction mixture was purified on a ReproSil-Pur C18 reversed phase column eluted with water/acetonitrile 30-70% containing 0.1% formic acid. Product fractions were lyophilized giving the title compound as a white solid, 9 mg (0.017 mmol), 98.96% pure, 57.4%. Product identity assigned by NMR.

LCMS (ESI) m/z for C28H23F2N7O3 543 (calcd) 544 ($[M+H]^+$, found).

$^1H$ NMR (400 MHz, DMSO) δ 10.09 (d, J=7.0 Hz, 1H), 9.25 (d, J=2.8 Hz, 1H), 8.80-8.75 (m, 2H), 8.16 (d, J=6.5 Hz, 1H), 8.05 (d, J=8.8 Hz, 1H), 7.93 (d, J=2.9 Hz, 1H), 7.62-7.52 (m, 2H), 7.50 (dd, J=8.8, 2.9 Hz, 1H), 7.46-7.38 (m, 1H), 7.37-7.26 (m, 1H), 4.81-4.67 (m, 1H), 4.10 (q, J=6.9 Hz, 2H), 3.39-3.35 (m, 1H), 2.91-2.75 (m, 1H), 2.72-2.60 (m, 1H), 2.48-2.29 (m, 2H), 1.31 (t, J=6.9 Hz, 3H).

Example 30—ADME Properties

Cellular $IC_{50}$ and biochemical $IC_{50}$ values for the compounds of Examples 7 to 29 were determined as described in Example 6. The results are provided in table 3:

TABLE 3

| Compound Example No. | Cellular $IC_{50}$ HEK 293 (μM) | Cellular $IC_{50}$ HEK 293 (nM) | Biochemical $IC_{50}$ TNKS2 (nM) |
|---|---|---|---|
| 7 | 0.070 | 70 | — |
| 8 | 0.021 | 21 | — |
| 9 | 0.19 | 187 | — |
| 10 | 0.041 | 41 | — |
| 11 | 2.8 | 2769 | — |
| 12 | >10 | >10000 | — |
| 13 | >10 | >10000 | — |
| 14 | 0.0085 | 8.5 | — |
| 15 | 0.130 | 130 | — |
| 16 | 2.3 | 2263 | — |
| 17 | 0.060 | 60 | — |
| 18 | >10 | >10000 | — |
| 19 | 0.034 | 34 | — |
| 20 | 0.027 | 27 | 7.2 |
| 21 | 0.072 | 72 | 12.5 |
| 22 | 0.015 | 15 | 2.1 |
| 23 | 0.0036 | 3.6 | 1.3 |

TABLE 3-continued

| Compound Example No. | Cellular $IC_{50}$ HEK 293 (μM) | Cellular $IC_{50}$ HEK 293 (nM) | Biochemical $IC_{50}$ TNKS2 (nM) |
|---|---|---|---|
| 24 | 0.0037 | 3.7 | 1.8 |
| 25 | 10 | 9959 | 978 |
| 26 | 0.0014 | 1.4 | 2.6 |
| 27 | 0.022 | 22 | 1.7 |
| 28 | 0.0012 | 1.2 | 3.5 |
| 29 | 0.0028 | 2.8 | 1.8 |

The invention claimed is:

1. A compound of general formula (I), or a tautomer, stereoisomer, N-oxide, pharmaceutically acceptable salt or pro-drug thereof:

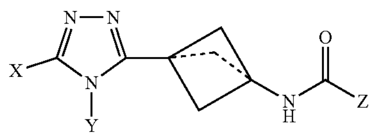

(I)

wherein:

a dashed line indicates an optional bond;

X represents:

a 5- or 6-membered, unsaturated heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$, where each R is independently H or $C_{1-6}$ alkyl;

a $C_{3-5}$ cycloalkyl group optionally substituted by one or more substituents independently selected from $C_{1-6}$ alkyl, $C_{1-6}$ haloalkyl, and $C_{1-6}$ alkoxy; or an aryl group optionally substituted by one or more substituents independently selected from halogen, $C_{1-6}$ alkyl, $C_{1-6}$ haloalkyl, and $C_{1-6}$ alkoxy;

Y represents:

an aryl or heteroaryl group optionally substituted by one or more substituents independently selected from halogen, $C_{1-6}$ alkyl, $C_{1-6}$ haloalkyl, and $C_{1-6}$ alkoxy;

a 5- or 6-membered, saturated heterocyclic group optionally substituted by one or more substituents independently selected from $C_{1-6}$ alkyl, $C_{1-6}$ haloalkyl, and $C_{1-6}$ alkoxy; or a $C_{3-6}$ cycloalkyl group optionally substituted by one or more substituents independently selected from $C_{1-6}$ alkyl, $C_{1-6}$ haloalkyl, and $C_{1-6}$ alkoxy; and Z represents:

an aryl group optionally substituted by one or more substituents independently selected from halogen, $C_{1-6}$ alkyl, $C_{1-6}$ haloalkyl, $C_{1-6}$ alkoxy, —CN, —$NO_2$, —OH, —$N(R^1)_2$, where each $R^1$ is independently H or $C_{1-6}$ alkyl, —$SO_2R^2$, where $R^2$ is H or $C_{1-6}$ alkyl, —$SO_2N(R^3)_2$, where each $R^3$ is independently H or $C_{1-6}$ alkyl, and —$C(O)N(R^4)_2$, where each $R^4$ is independently H or $C_{1-6}$ alkyl, or wherein both $R^4$ groups, together with the intervening nitrogen atom, form a 3 to 6 membered saturated heterocyclic ring; or an unsaturated, 5- to 10-membered mono- or bicyclic heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —OH, —$N(R^1)_2$, where each $R^1$ is independently H or $C_{1-6}$ alkyl, —$SO_2R^2$, where $R^2$ is H or $C_{1-6}$ alkyl, —$SO_2N(R^3)_2$, where each $R^3$ is independently H or $C_{1-6}$ alkyl, and —$C(O)N(R^4)_2$, where each $R^4$ is independently H or $C_{1-6}$ alkyl, or wherein both $R^4$ groups, together with the intervening nitrogen atom, form a 3 to 6 membered saturated heterocyclic ring;

with the proviso:

that when the compound is other than an N-oxide of formula (I), Z must be substituted by at least one substituent selected from —OH, —$N(R^1)_2$, —$SO_2N(R^3)_2$ and —$C(O)N(R^4)_2$.

2. The compound as claimed in claim 1, wherein said compound is provided in the form of an N-oxide.

3. The compound as claimed in claim 1, wherein Z is substituted by at least one substituent selected from —OH, —$N(R^1)_2$, —$SO_2N(R^3)_2$ and —$C(O)N(R^4)_2$.

4. The compound as claimed in claim 1, wherein X represents:

a 5- or 6-membered, unsaturated heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$, where each R is independently H or $C_{1-6}$ alkyl; or a $C_{3-5}$ cycloalkyl group optionally substituted by one or more substituents independently selected from $C_{1-6}$ alkyl, $C_{1-6}$ haloalkyl, and $C_{1-6}$ alkoxy.

5. The compound as claimed in claim 1, wherein X is an optionally substituted, 5- or 6-membered, unsaturated heterocyclic group, wherein said unsaturated heterocyclic group is selected from any of the following: pyridinyl, pyrimidinyl, pyrrolyl, pyrazinyl, thiazolyl, pyrazolyl, imidazolyl and thiophenyl.

6. The compound as claimed in claim 1, wherein X is selected from any of the following groups:

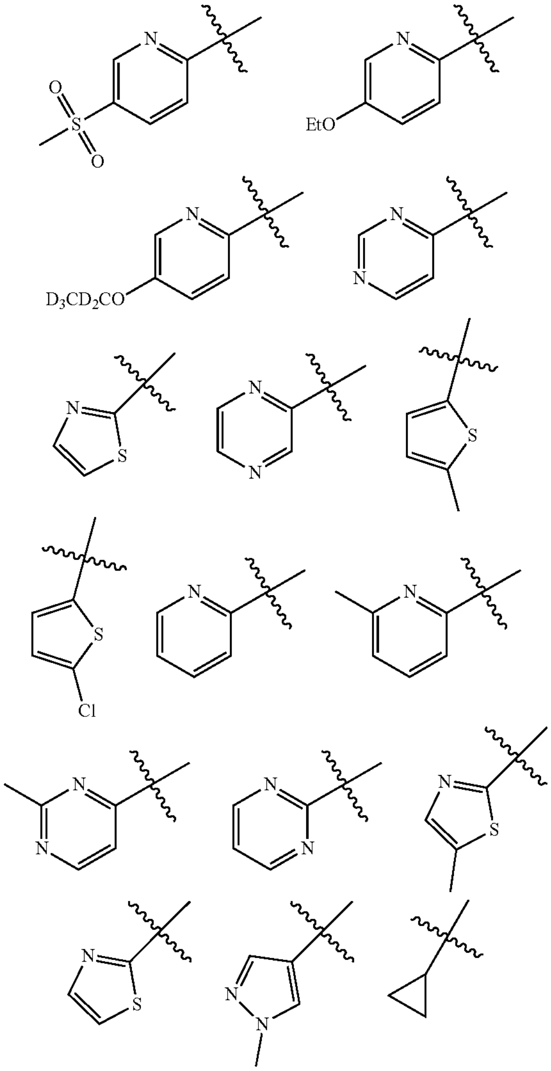

-continued

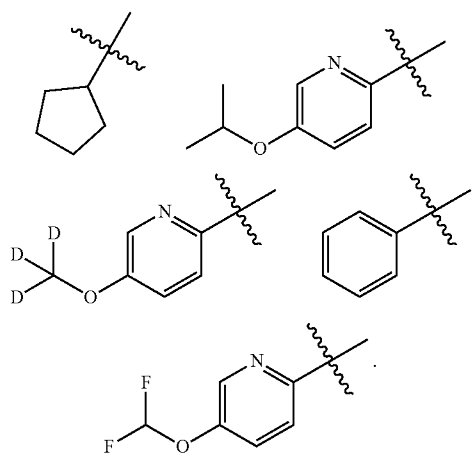

7. The compound as claimed in claim 1, wherein Y is an optionally substituted, aryl or heteroaryl group.

8. The compound as claimed in claim 7, wherein Y is a phenyl group optionally substituted by one or two substituents selected from the group consisting of: $C_{1-3}$ alkyl, $C_{1-3}$ alkoxy, $C_{1-3}$ haloalkyl, and halogen.

9. The compound as claimed in claim 7, wherein Y is a pyridinyl or thiophenyl ring, optionally substituted by one or two substituents selected from the group consisting of: $C_{1-3}$ alkyl, $C_{1-3}$ alkoxy, $C_{1-3}$ haloalkyl, and halogen.

10. The compound as claimed in claim 1, wherein Y is selected from any of the following groups:

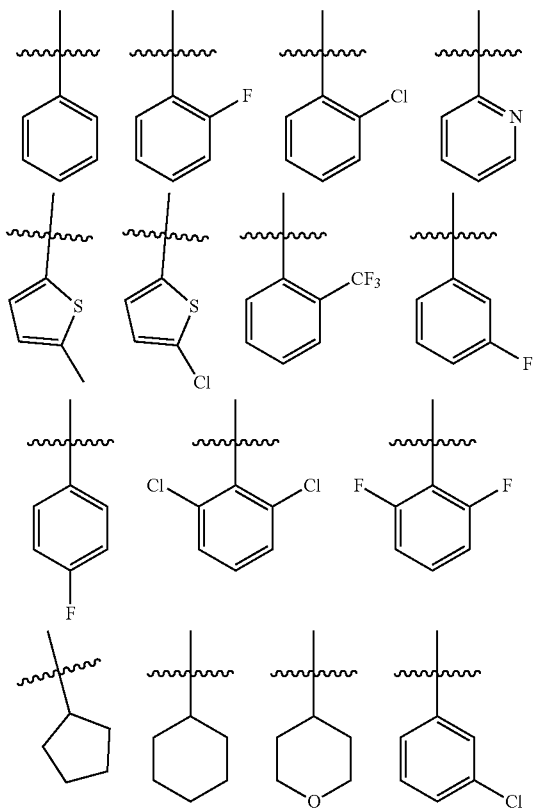

-continued

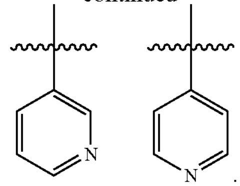

11. The compound as claimed in claim 1, wherein Z represents an optionally substituted aryl group.

12. The compound as claimed in claim 11, wherein Z is a phenyl or naphthyl group optionally substituted by one or two substituents independently selected from —OH, —$NH_2$, —NH($C_{1-3}$ alkyl), —N($C_{1-3}$ alkyl)$_2$, —$SO_2NH_2$, —$SO_2$NH($C_{1-3}$ alkyl), —$SO_2$N($C_{1-3}$ alkyl)$_2$, —C(O)$NH_2$, —C(O)NH($C_{1-3}$ alkyl), —C(O)N($C_{1-3}$ alkyl)$_2$, and —C(O)N($R^4$)$_2$ wherein both $R^4$ groups, together with the intervening nitrogen atom, form a 3 to 6 membered saturated heterocyclic ring.

13. The compound as claimed in claim 1, wherein Z is an optionally substituted, unsaturated, 5- to 10-membered mono- or bicyclic heterocyclic group.

14. The compound as claimed in claim 13, wherein said heterocyclic group is substituted by one or more substituents independently selected from $C_{1-3}$ alkyl, $C_{1-3}$ alkoxy, $C_{1-3}$ haloalkyl, halogen, —OH, —$NH_2$, —NH($C_{1-3}$ alkyl), —N($C_{1-3}$ alkyl)$_2$, —$SO_2NH_2$, —$SO_2$NH($C_{1-3}$ alkyl), —$SO_2$N($C_{1-3}$ alkyl)$_2$, —C(O)$NH_2$, —C(O)NH($C_{1-3}$ alkyl), —C(O)N($C_{1-3}$ alkyl)$_2$, or —C(O)N($R^4$)$_2$ wherein both $R^4$ groups, together with the intervening nitrogen atom, form a 3 to 6 membered saturated heterocyclic ring.

15. The compound as claimed in claim 11, wherein Z is selected from any of the following groups:

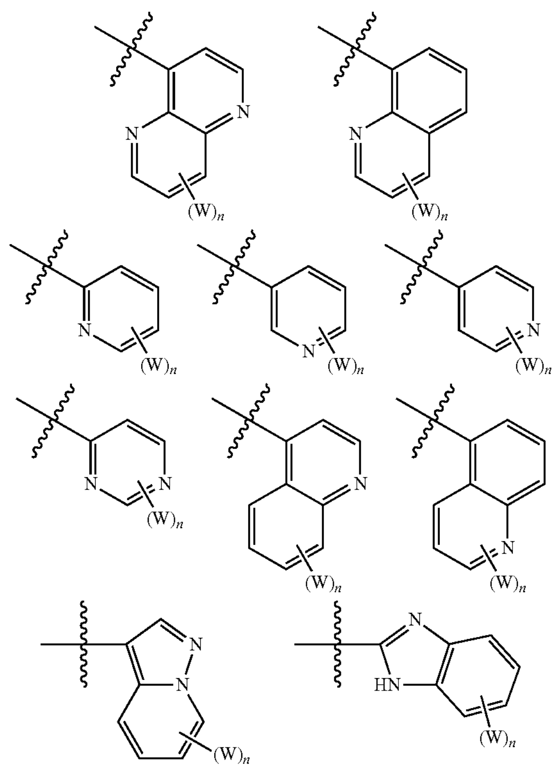

-continued

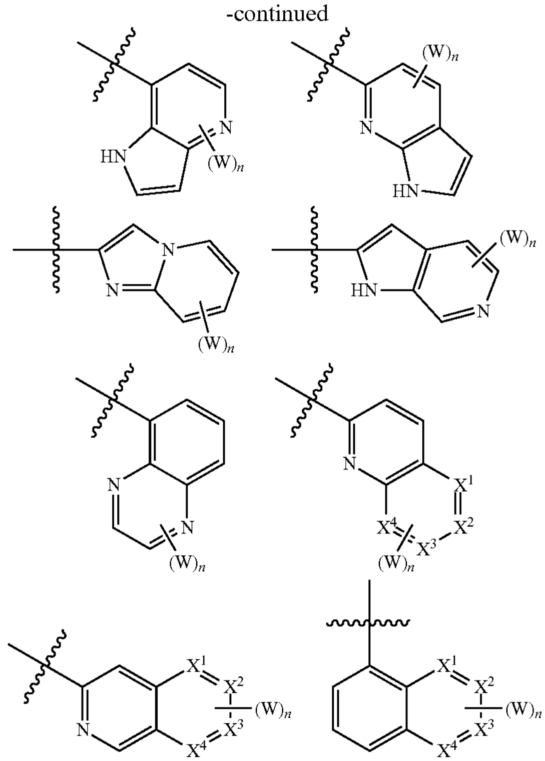

wherein n is 0, 1 or 2;

W is a substituent group selected from halogen, $C_{1-6}$ alkyl, $C_{1-6}$ haloalkyl, $C_{1-6}$ alkoxy, —CN, —$NO_2$, —OH, —$N(R^1)_2$, where each $R^1$ is independently H or $C_{1-6}$ alkyl, —$SO_2R^2$, where $R^2$ is H or $C_{1-6}$ alkyl, —$SO_2N(R^3)_2$, where each $R^3$ is independently H or $C_{1-6}$ alkyl, and —$C(O)N(R^4)_2$, where each $R^4$ is independently H or $C_{1-6}$ alkyl, or wherein both $R^4$ groups, together with the intervening nitrogen atom, form a 3 to 6 membered saturated heterocyclic ring); and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH; or two of $X^1$, $X^2$, $X^3$ and $X^4$ are N and the remaining two of $X^1$, $X^2$, $X^3$ and $X^4$ are CH.

16. The compound as claimed in claim 15, wherein n is 1 or 2, and each W is independently selected from halogen, $C_{1-3}$ alkyl, $C_{1-3}$ alkoxy, —CN, —OH, —$NH_2$, —$NH(C_{1-3}$ alkyl), —$N(C_{1-3}$ alkyl$)_2$, —$SO_2NH_2$, —$SO_2NH(C_{1-3}$ alkyl), —$SO_2N(C_{1-3}$ alkyl$)_2$, —$C(O)NH_2$, —$C(O)NH(C_{1-3}$ alkyl), —$C(O)N(C_{1-3}$ alkyl$)_2$, or —$C(O)N(R^4)_2$ wherein both $R^4$ groups, together with the intervening nitrogen atom, form a 3 to 6 membered saturated heterocyclic ring.

17. The compound as claimed in claim 1, wherein Z is selected from optionally substituted phenyl, naphthyl, pyridinyl, pyrimidinyl, quinolinyl, 1,5-naphthyridinyl, benzimidazolyl, pyrazolo[1,5-a]pyridinyl and quinoxalinyl.

18. The compound as claimed in claim 1, wherein Z is substituted by one or more groups selected from —OH, —$NH_2$, —$SO_2NH_2$, —$C(O)NH_2$, —$C(O)NHCH_3$, —$C(O)N(CH_3)_2$, and

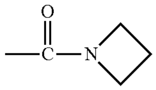

19. The compound as claimed in claim 1, wherein Z is selected from any of the following groups:

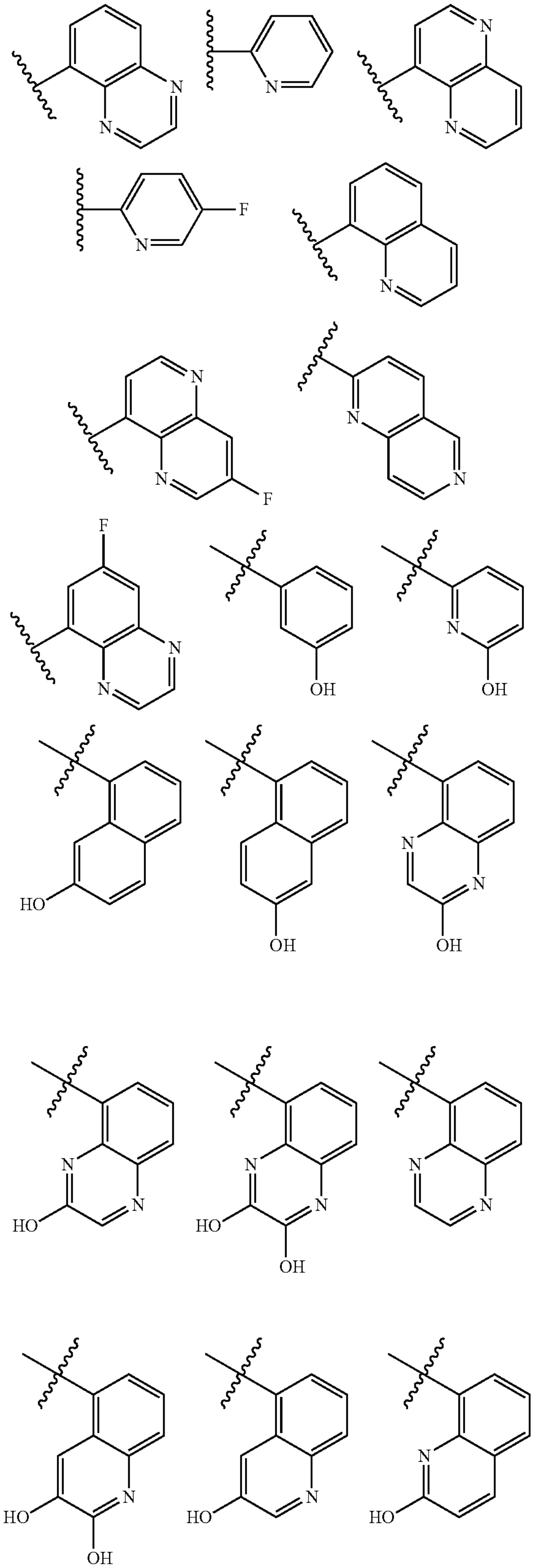

-continued

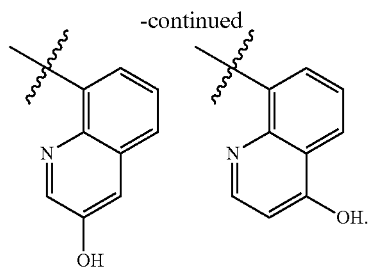

20. The compound as claimed in claim 1 having the general formula (I'), or a tautomer, stereoisomer, N-oxide, pharmaceutically acceptable salt or pro-drug thereof:

(I')

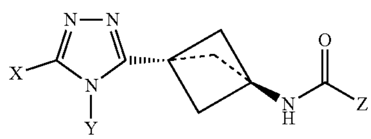

wherein:

X represents:

- a 5- or 6-membered, unsaturated heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$, where each R is independently H or $C_{1-6}$ alkyl;
- a $C_{3-5}$ cycloalkyl group optionally substituted by one or more substituents independently selected from $C_{1-6}$ alkyl, $C_{1-6}$ haloalkyl, and $C_{1-6}$ alkoxy; or
- an aryl group optionally substituted by one or more substituents independently selected from halogen, $C_{1-6}$ alkyl, $C_{1-6}$ haloalkyl, and $C_{1-6}$ alkoxy;

Y represents:

- an aryl or heteroaryl group optionally substituted by one or more substituents independently selected from halogen, $C_{1-6}$ alkyl, $C_{1-6}$ haloalkyl, and $C_{1-6}$ alkoxy;
- a 5- or 6-membered, saturated heterocyclic group optionally substituted by one or more substituents independently selected from $C_{1-6}$ alkyl, $C_{1-6}$ haloalkyl, and $C_{1-6}$ alkoxy; or
- a $C_{3-6}$ cycloalkyl group optionally substituted by one or more substituents independently selected from $C_{1-6}$ alkyl, $C_{1-6}$ haloalkyl, and $C_{1-6}$ alkoxy; and Z represents:

- an aryl group optionally substituted by one or more substituents independently selected from halogen, $C_{1-6}$ alkyl, $C_{1-6}$ haloalkyl, $C_{1-6}$ alkoxy, —CN, —$NO_2$, —OH, —$N(R^1)_2$, where each $R^1$ is independently H or $C_{1-6}$ alkyl, —$SO_2R^2$, where $R^2$ is H or $C_{1-6}$ alkyl, $SO_2N(R^3)_2$, where each $R^3$ is independently H or $C_{1-6}$ alkyl, and —$C(O)N(R^4)_2$, where each $R^4$ is independently H or $C_{1-6}$ alkyl, or wherein both $R^4$ groups, together with the intervening nitrogen atom, form a 3 to 6 membered saturated heterocyclic ring; or
- an unsaturated, 5- to 10-membered mono- or bicyclic heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —OH, —$N(R^1)_2$, where each $R^1$ is independently H or $C_{1-6}$ alkyl, —$SO_2R^2$, where $R^2$ is H or $C_{1-6}$ alkyl, $SO_2N(R^3)_2$, where each $R^3$ is independently H or $C_{1-6}$ alkyl, and —$C(O)N(R^4)_2$, where each $R^4$ is independently H or $C_{1-6}$ alkyl, or wherein both $R^4$ groups, together with the intervening nitrogen atom, form a 3 to 6 membered saturated heterocyclic ring;

with the proviso:

that when the compound is other than an N-oxide of formula (I'), Z must be substituted by at least one substituent selected from —OH, —$N(R^1)_2$, —$SO_2N(R^3)_2$ and —$C(O)N(R^4)_2$.

21. The compound as claimed in claim 1 selected from any of the following compounds, or a tautomer, a stereoisomer, an N-oxide, a pharmaceutically acceptable salt or a pro-drug thereof:

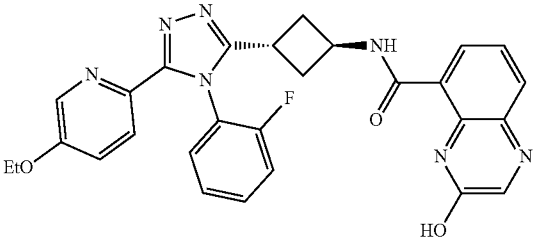

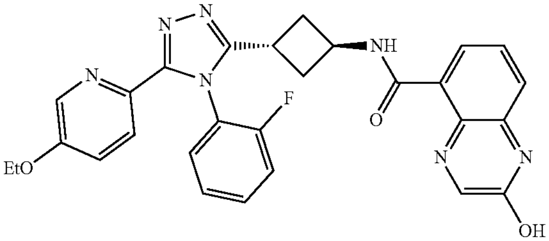

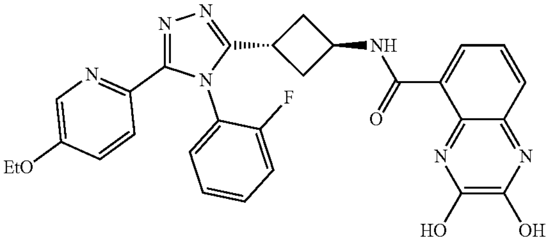

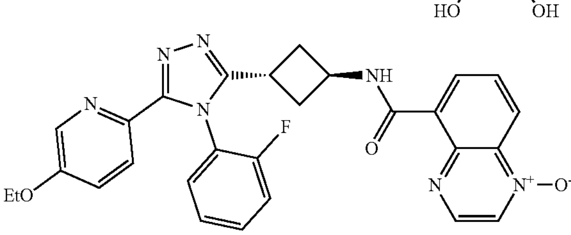

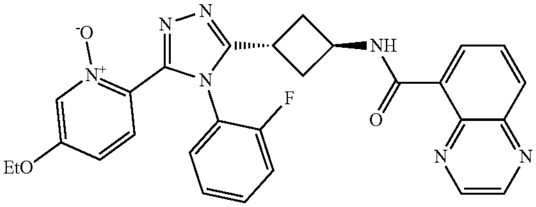

-continued
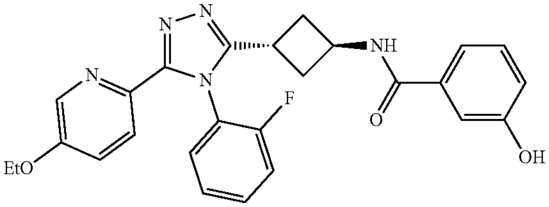
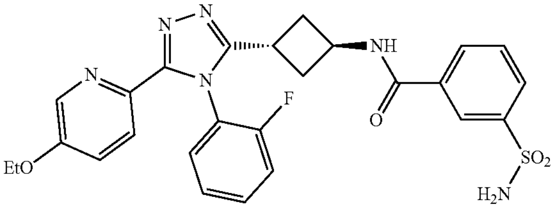
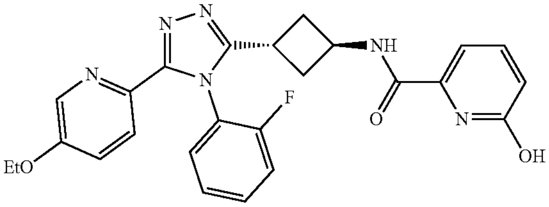
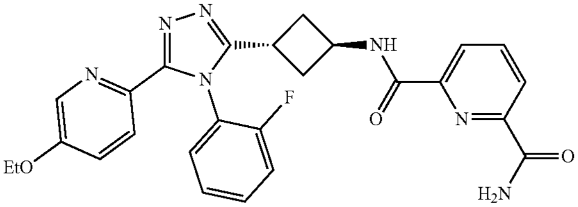
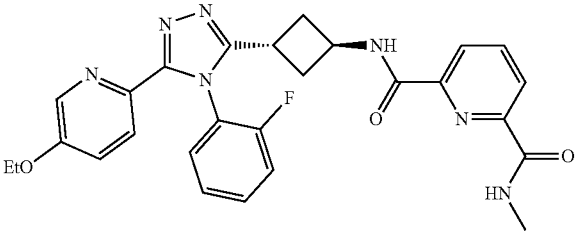
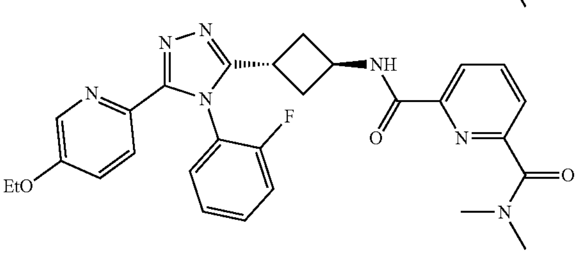
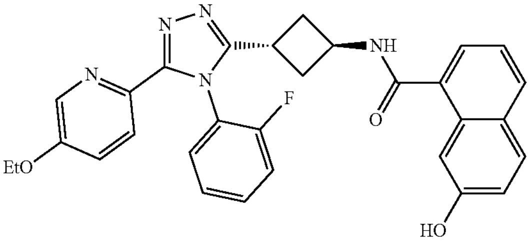
-continued
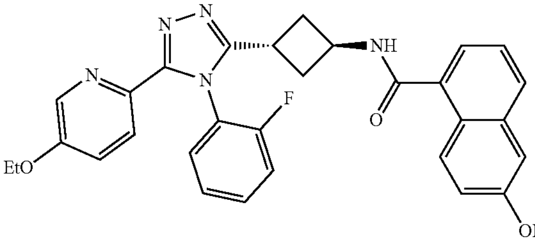
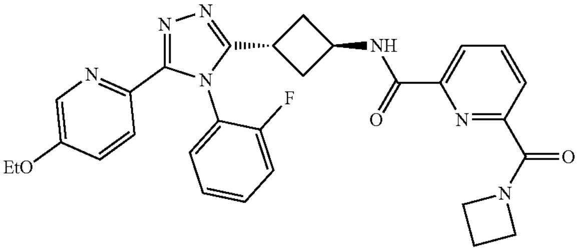
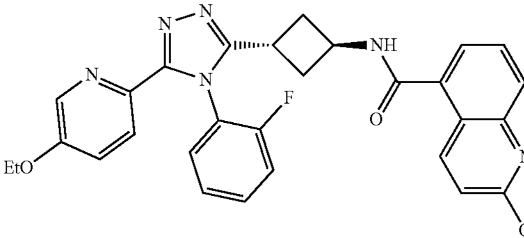
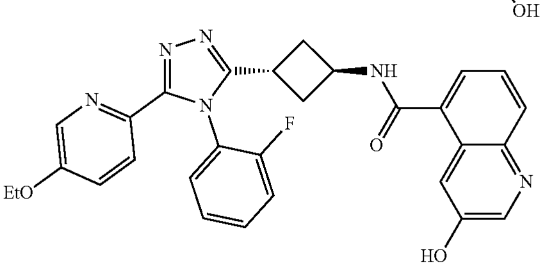
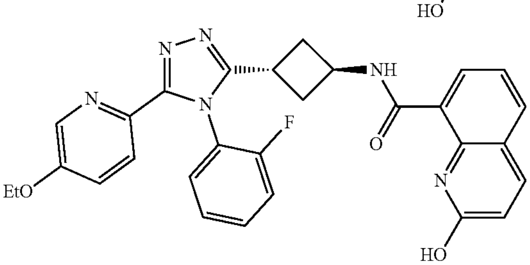
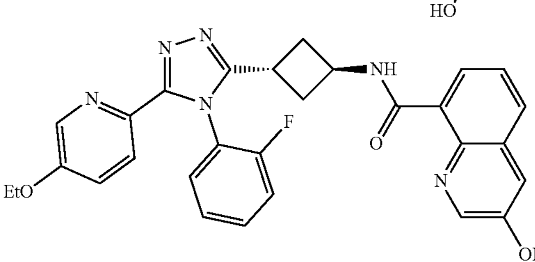
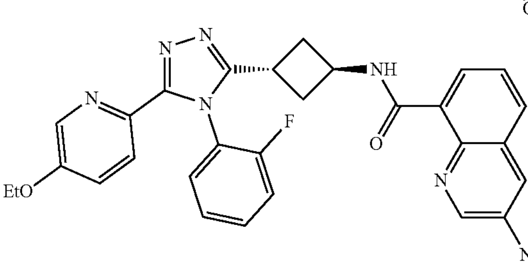

-continued
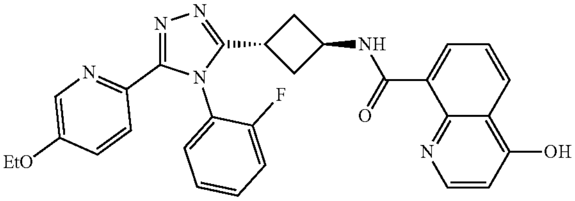
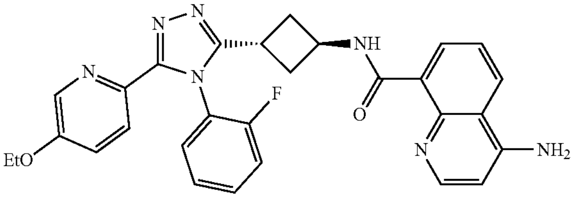
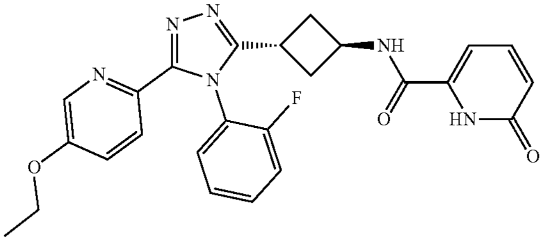
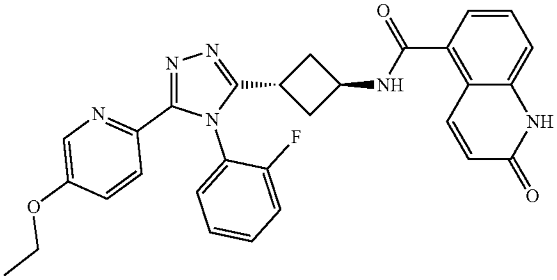
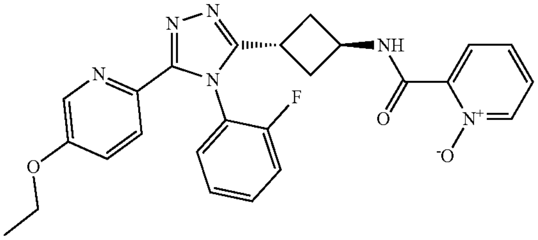
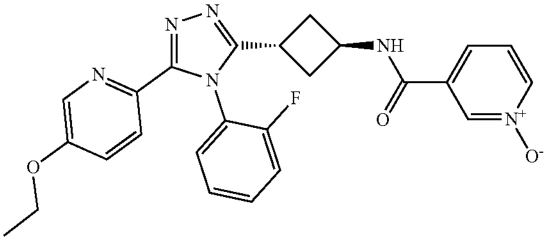
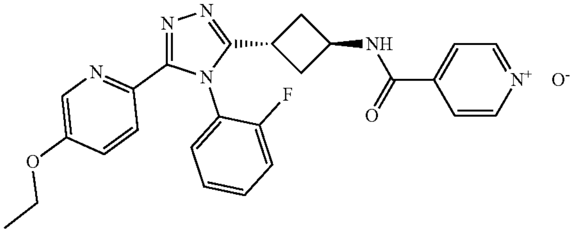
-continued
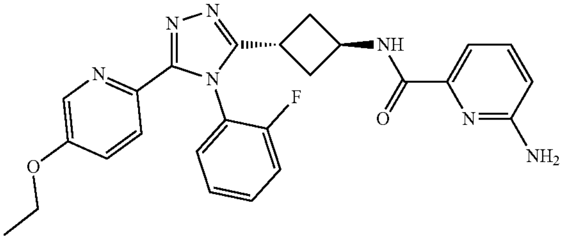
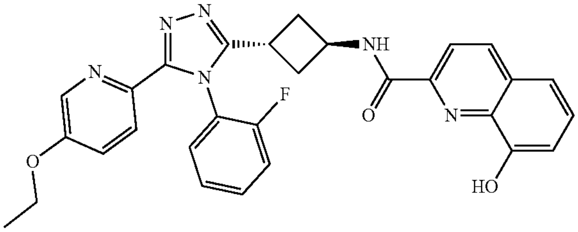
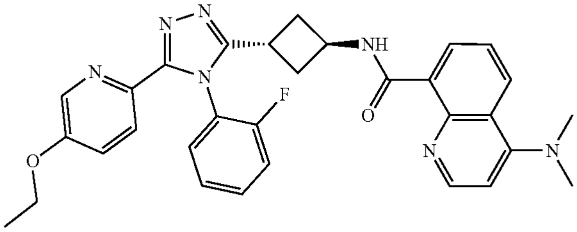
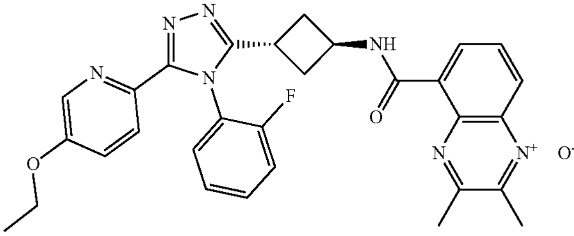
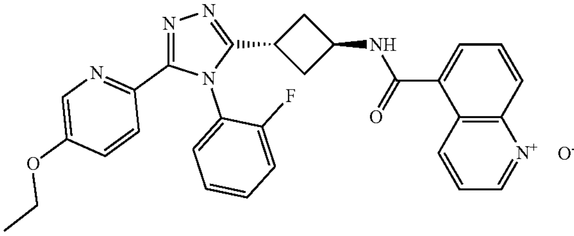
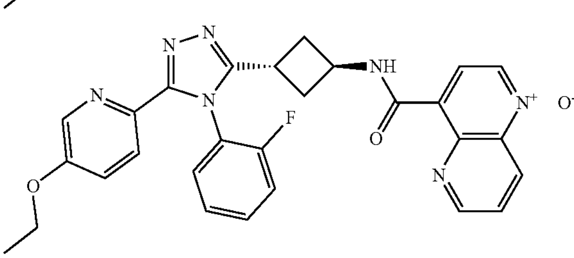
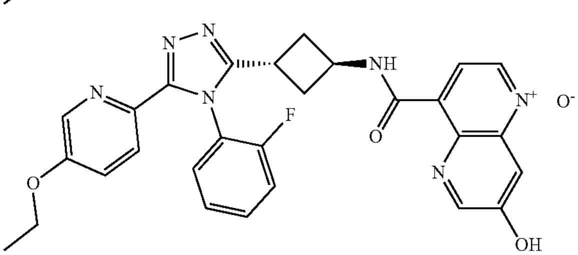

-continued

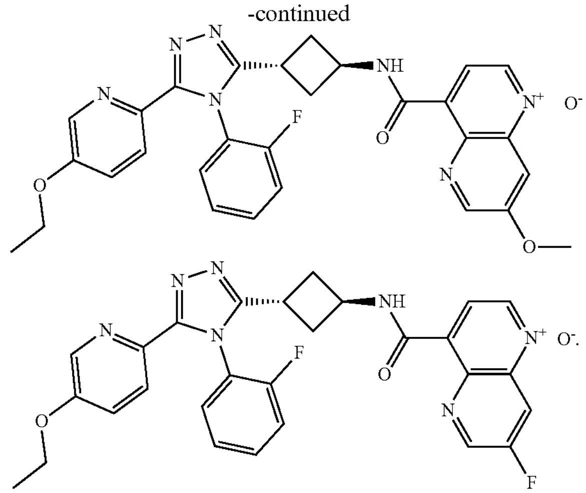

22. A pharmaceutical composition comprising a compound as claimed in claim 1, or a tautomer, a stereoisomer, an N-oxide, a pharmaceutically acceptable salt, or a prodrug thereof, together with one or more pharmaceutically acceptable carriers, excipients or diluents.

23. A method of treatment of an existing disease or disorder responsive to inhibition of tankyrase 2, said method comprising the step of administering to a patient in need thereof a pharmaceutically effective amount of a compound as claimed in claim 1, or a tautomer, a stereoisomer, an N-oxide, a pharmaceutically acceptable salt, or a pro-drug thereof.

24. The method of treatment as claimed in claim 23, wherein said disease or disorder is cancer, non-regenerative wound healing, a viral infection, fibrosis, osteoarthritis or a metabolic condition.

* * * * *